(12) United States Patent
Hutmacher et al.

(10) Patent No.: US 7,604,987 B2
(45) Date of Patent: Oct. 20, 2009

(54) BIOREACTOR FOR GROWING CELL OR TISSUE CULTURES

(75) Inventors: Dietmar W. Hutmacher, Sunset Lodge (SG); Swee Hin Teoh, Singapore (SG); Manoja Ranawake, Hurstville (AU); Woon Shin Chong, Singapore (SG); Keng Soon Ting, Singapore (SG); Kay Chiang Chua, Singapore (SG); Than Myint, Singapore (SG); Chum Mok Puah, Singapore (SG); Toon Tien Foo, Singapore (SG); Jan-Thorsten Schantz, Singapore (SG)

(73) Assignee: National University of Singapore, Singapore (SG)

( * ) Notice: Subject to any disclaimer, the term of this patent is extended or adjusted under 35 U.S.C. 154(b) by 554 days.

(21) Appl. No.: 11/124,618

(22) Filed: May 6, 2005

(65) Prior Publication Data
US 2006/0019388 A1   Jan. 26, 2006

Related U.S. Application Data

(63) Continuation-in-part of application No. 10/774,360, filed on Feb. 6, 2004, now abandoned.

(60) Provisional application No. 60/569,484, filed on May 7, 2004, provisional application No. 60/455,252, filed on Feb. 6, 2003.

(51) Int. Cl.
*C12M 1/00* (2006.01)
(52) U.S. Cl. ............... 435/298.1; 435/289.1; 435/291.8; 435/298.2; 435/394; 422/209; 366/206; 366/217

(58) Field of Classification Search ............... 435/291.8, 435/298.2, 394; 366/200, 217, 218
See application file for complete search history.

(56) References Cited

U.S. PATENT DOCUMENTS

| 4,146,335 | A | * | 3/1979 | Hutchings et al. ............ 366/217 |
| 4,169,010 | A | * | 9/1979 | Marwil ....................... 435/247 |
| 4,606,560 | A | | 8/1986 | McCracken |
| 4,758,026 | A | | 7/1988 | Timm |
| 4,874,358 | A | | 10/1989 | Brimhall et al. |
| 5,044,673 | A | | 9/1991 | Jones, Jr. |
| 5,071,760 | A | * | 12/1991 | Watanabe et al. ........... 435/394 |
| 5,148,090 | A | | 9/1992 | Oku et al. |
| 5,151,368 | A | | 9/1992 | Brimhall et al. |
| 5,348,352 | A | | 9/1994 | Ciez et al. |

(Continued)

FOREIGN PATENT DOCUMENTS

CA           2242539          2/2000

(Continued)

*Primary Examiner*—William H Beisner
*Assistant Examiner*—Michael Hobbs
(74) *Attorney, Agent, or Firm*—Dinsmore & Shohl LLP

(57) ABSTRACT

The invention relates to a bioreactor comprising a chamber for containing cells or tissue cultures within a culture medium. The bioreactor also comprises a detector capable of detecting a change in one or more metabolites associated with growth of the cell or tissue cultures within the chamber and a chamber drive capable of rotating the chamber at a first speed about a first axis and a second speed about a second axis, the second axis being disposed at an angle relative to the first axis. In use, the magnitude of the first speed and the second speed are independently variable of each other.

25 Claims, 48 Drawing Sheets

U.S. PATENT DOCUMENTS

| | | | |
|---|---|---|---|
| 5,501,522 A | 3/1996 | Tung | |
| 5,523,228 A | 6/1996 | Ingram et al. | |
| 5,665,594 A * | 9/1997 | Schwarz et al. | 435/394 |
| 6,001,643 A * | 12/1999 | Spaulding | 435/298.2 |
| 6,490,880 B1 * | 12/2002 | Walsh | 62/457.9 |
| 6,642,019 B1 * | 11/2003 | Anderson et al. | 435/41 |
| 7,112,441 B2 * | 9/2006 | Uemura et al. | 435/394 |
| 7,163,821 B2 * | 1/2007 | Uemura et al. | 435/286.2 |

FOREIGN PATENT DOCUMENTS

WO    WO 99/32270 A1    7/1999

\* cited by examiner

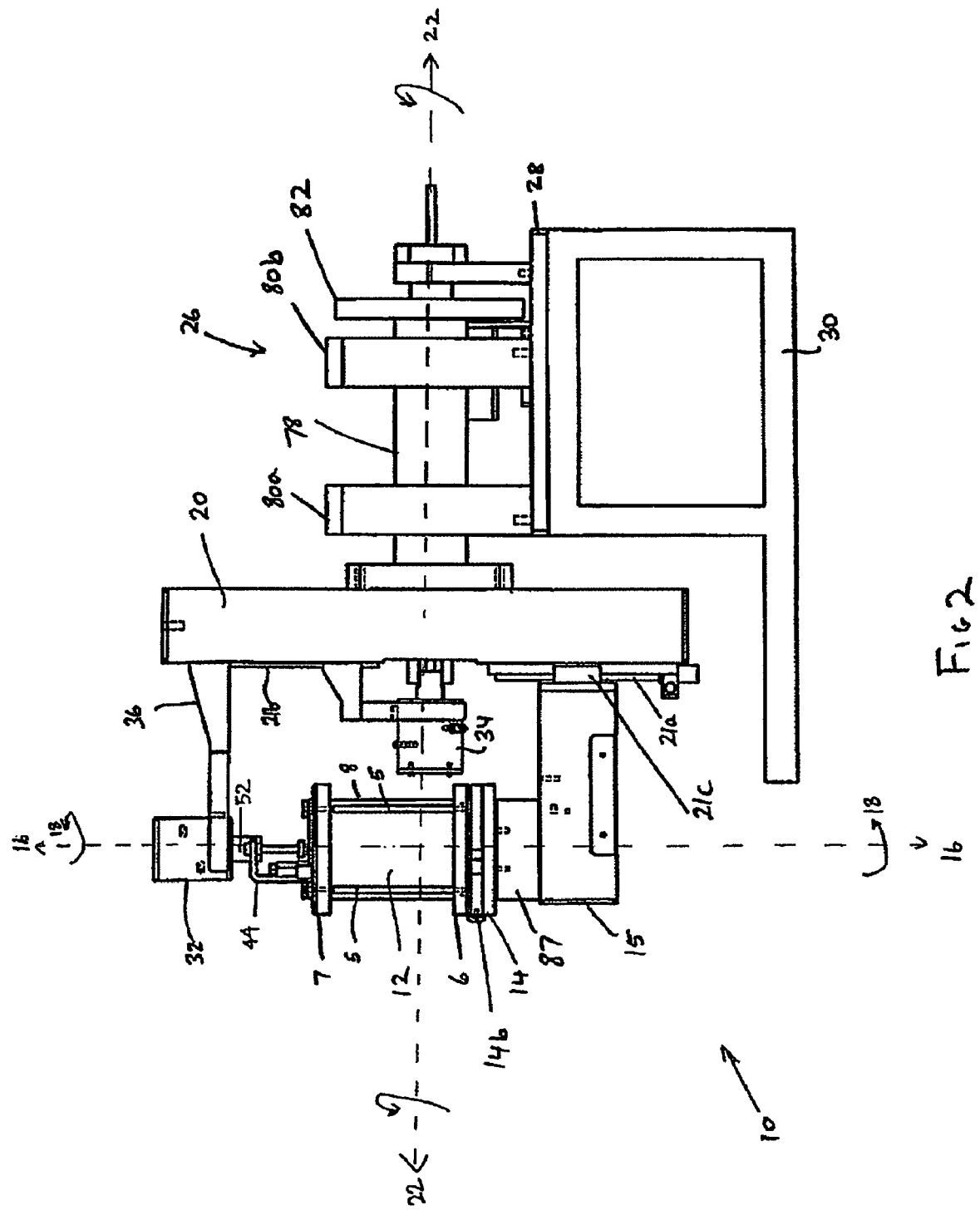

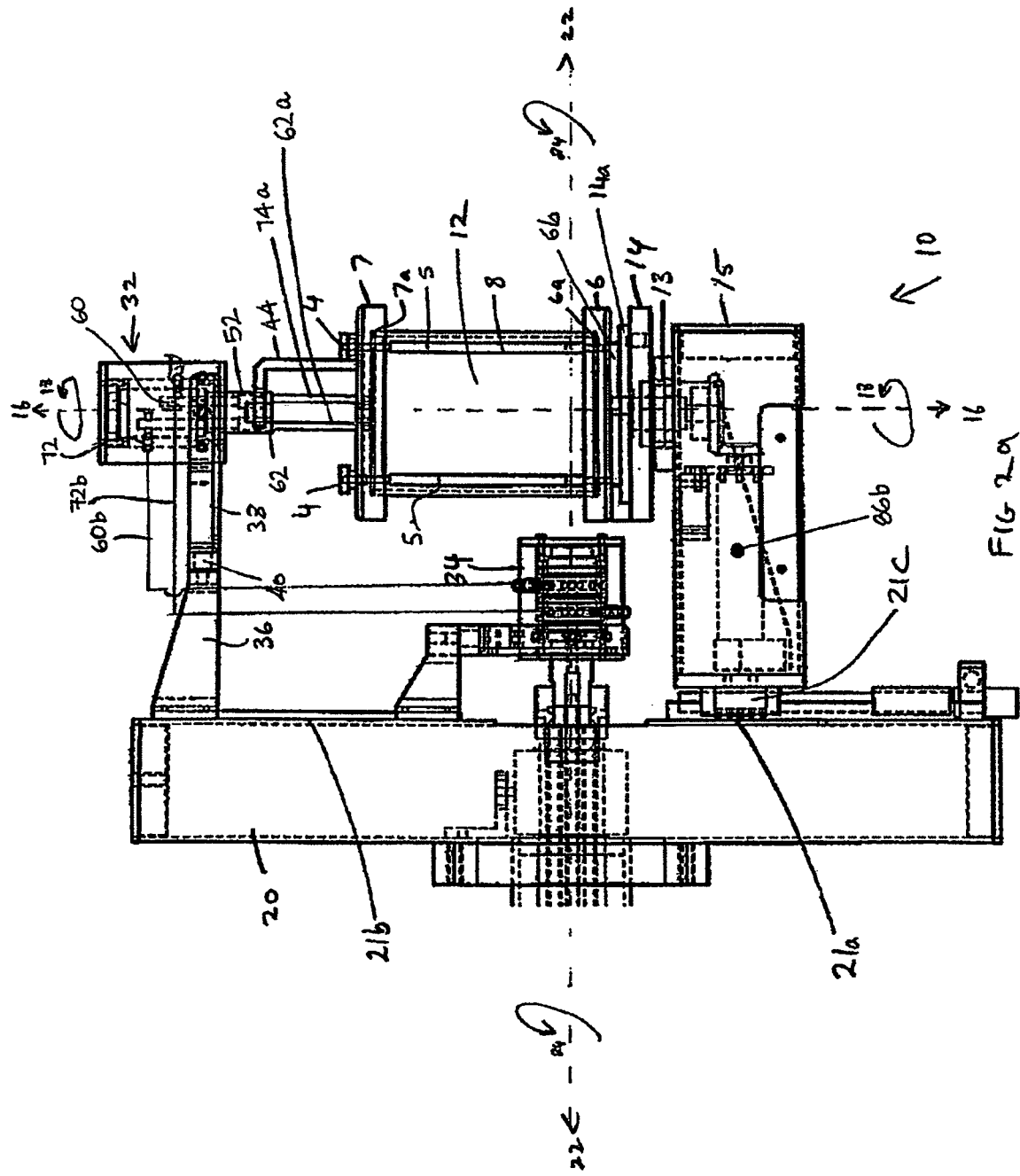

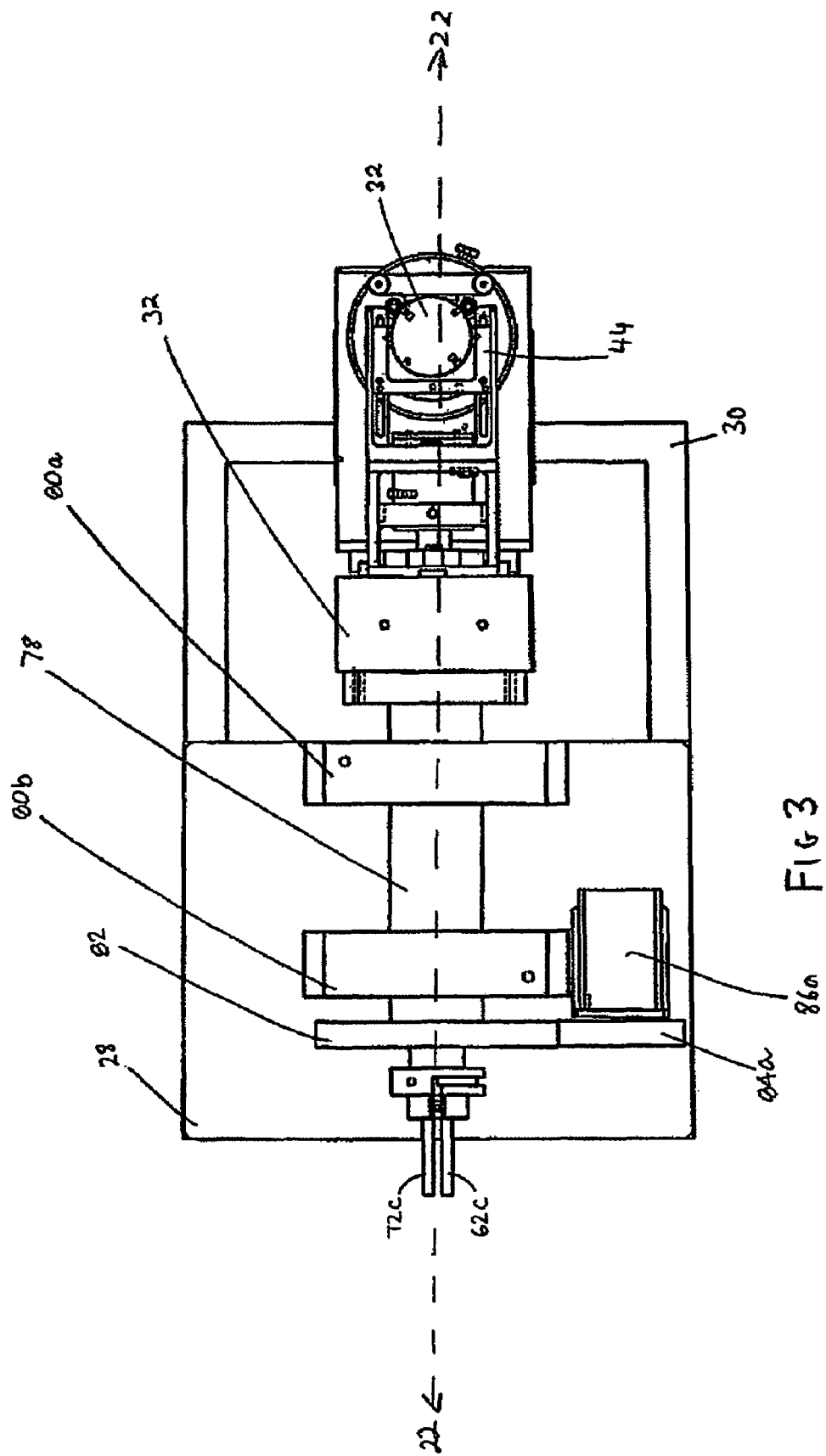

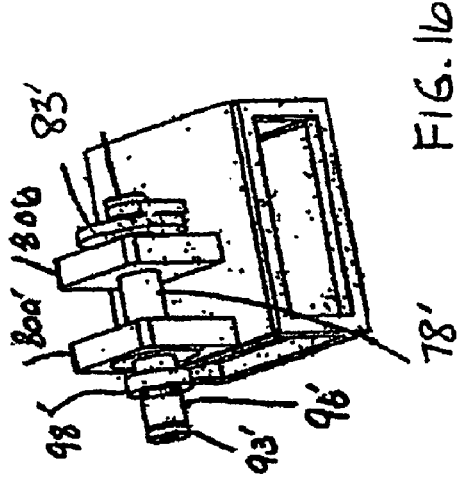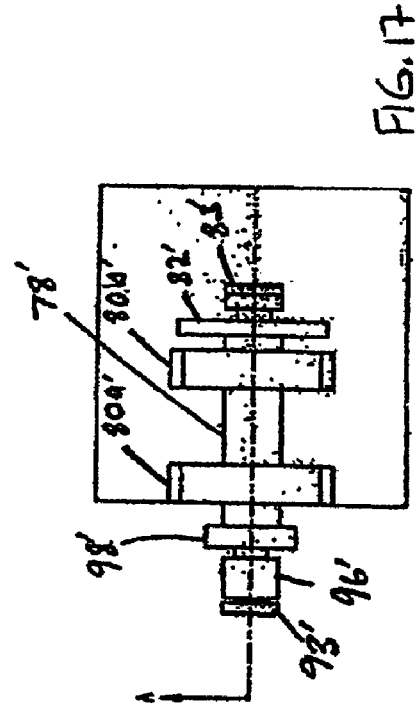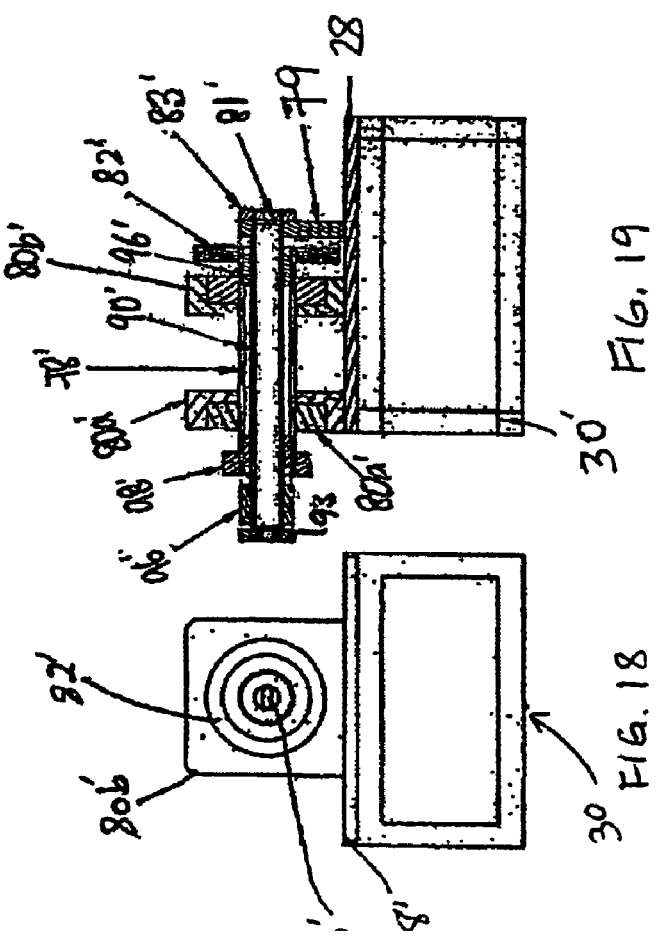

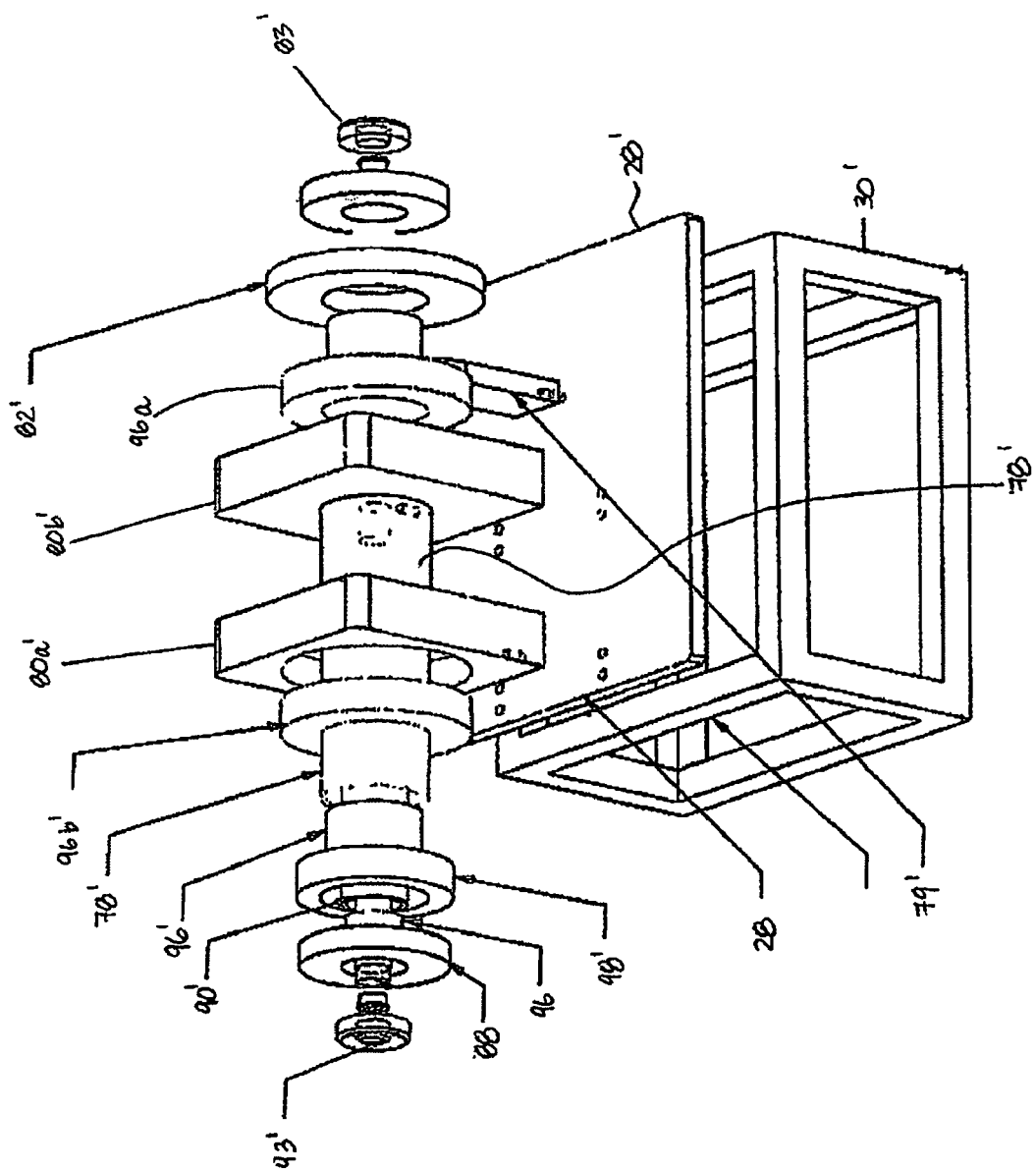

Fig. 37a TOP VIEW
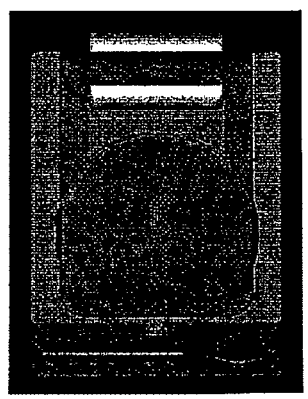
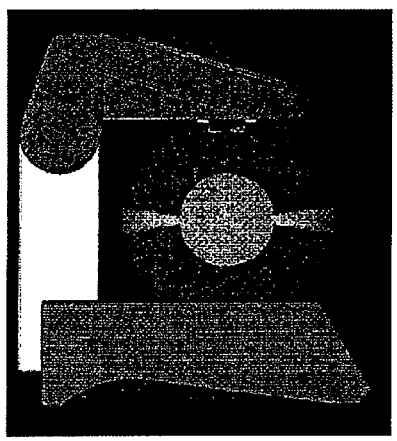
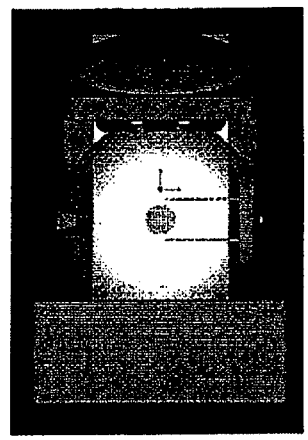
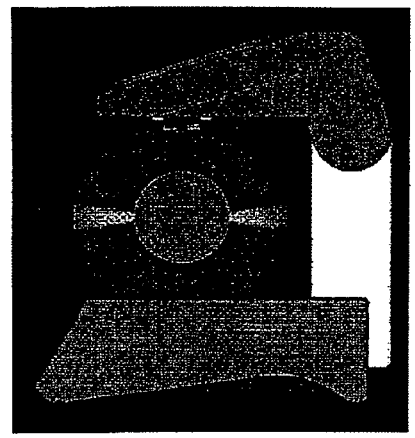
Fig. 37c LEFT VIEW
Fig. 37b FRONT VIEW
Fig. 37d RIGHT VIEW

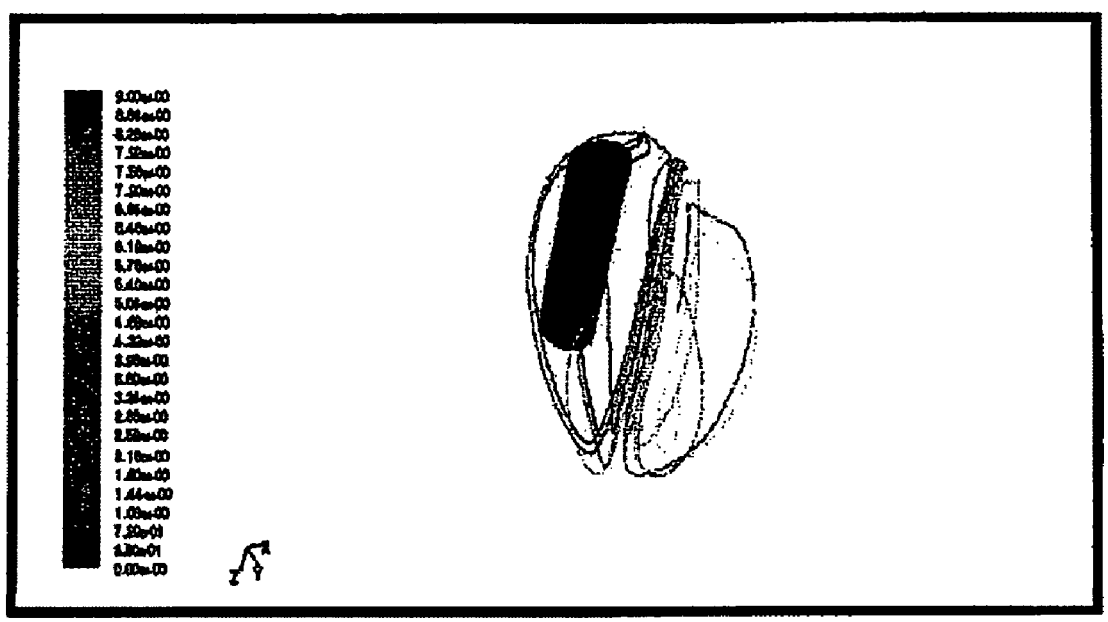
Figure 42 Path-line plot for spherical-shaped culture chamber 512.

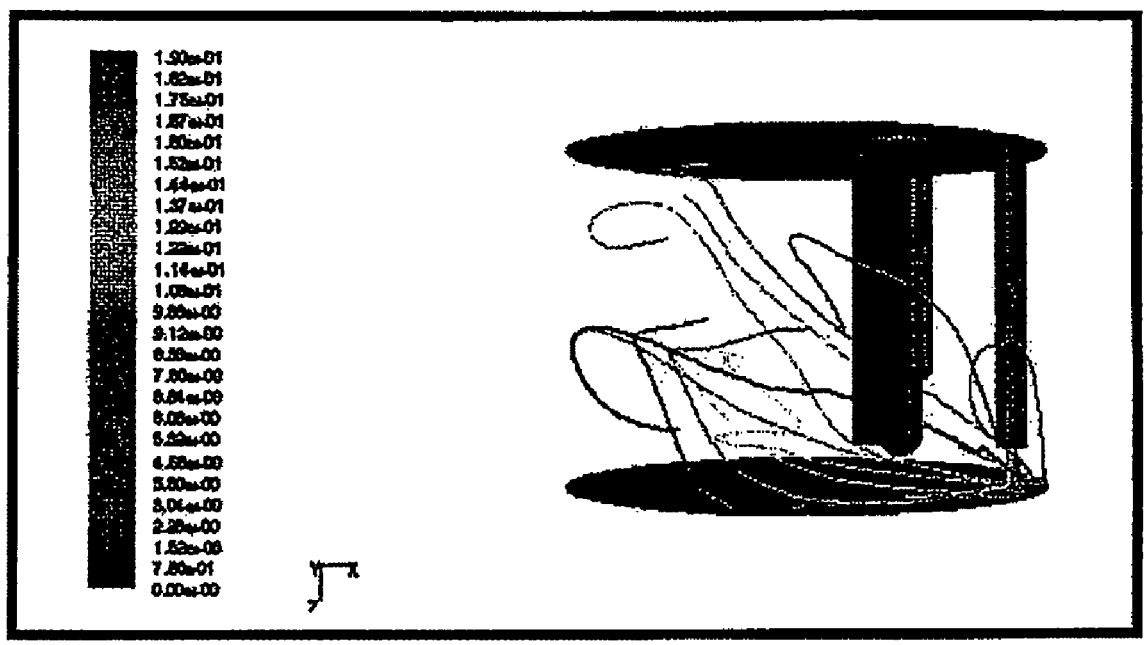
Figure 43. Path-line plot for cylindrical-shaped culture chamber 12.

BIOREACTOR FOR GROWING CELL OR TISSUE CULTURES

CROSS REFERENCE TO RELATED APPLICATIONS

This application is a continuation-in-part of application Ser. No. 10/774,360, filed Feb. 6, 2004, which claims the benefit of U.S. Provisional Application No. 60/445,252, filed Feb. 6, 2003. This application also claims the benefit of U.S. Provisional Application No. 60/569,484, filed May 7, 2004. All of these applications are incorporated by reference hereinto.

TECHNICAL FIELD

The present invention generally relates to a bioreactor for growing cell or tissue cultures.

BACKGROUND OF THE INVENTION

Defects in tissues resulting from disease or trauma have previously been healed through the regenerative process of wound healing. However, incomplete repair of the tissue may result when the defect is large, thereby resulting in fibrous scarring of the tissue. The fibrous scarring often possesses physical and mechanical properties that are inferior to that of non-scarred tissue.

Dramatic advances in the fields of biochemistry, cell and molecular biology, genetics, medicine, biomedical engineering and materials science have given rise to the cross-disciplinary field of tissue engineering, which uses synthetic or naturally derived, engineered scaffold/cell or scaffold/neotissue constructs for tissue regeneration. Ideally, tissue engineering aims to develop biological substitutes to solve the problem of organ and tissue deficiencies and provide medical implants. Bioreactors have been used to engineer cells and tissues.

In order to achieve optimal results in cell and tissue culture, the bioreactors should ideally operate under conditions that are as close as possible to in vivo conditions. Difficulties have arisen with known bioreactors in that they have not provided a constant and regulatory supply of nutrition and removal of metabolic byproducts. Accordingly, it is desirable that bioreactor systems maintain an organotypic environment to maintain cellular differentiation and optimal function.

The multiplication of cells is most commonly performed in culture dishes with a static medium supplemented with growth serum. Although cells grown in culture dishes multiply quite well, they tend to loose their differentiation status and are therefore functionally different from naturally grown cells. This has been found to be the case with chondrocytes from cartilage. Isolated chondrocytes flatten and look more like fibroblastic mesenchymal/stromal cells. No basic cartilage extracellular matrix results.

Known cell and tissue cultures for cell and tissue repair have utilized mono-layers of cell and tissue. For example, in a skin defect reaching a lower layer of the dermis has been treated by debriding a slough or an abnormal granulation tissue, reconstructing a normal granulation tissue by covering the defect with an allogenic skin, wound dressings or the like, and then reconstructing skin by autologous split-thickness skin grafting. A disadvantage with this procedure is that skin is taken from non-defect area of the patient's skin and some scarring may remain at the graft site. Furthermore, in circumstances where a wound extends over a wide area, it is difficult to carry out autologous split-thickness skin grafting. To prevent or diminish scarring and to increase the healing time of damaged tissues, a regenerative process has been carried out in vitro by growing cell or tissue cultures on monolayers (ie two-dimensional cell or tissue cultures) on an artificial substrate that is bathed in nutrient medium. The nature of the substrate on which the monolayers grow may be solid, such as plastic, or semisolid gels, such as collagen or agar. Disposable plastics substrates are presently used in cell or tissue culture.

Although the growth of cells in two dimensions is suitable for studying cells in culture, it lacks the cell-cell and cell-matrix interactions that are characteristic of whole tissue in vivo. To grow cells that have the cell-cell and cell-matrix interactions that are characteristic of whole tissue in vivo, the cells should preferably be grown in three-dimensions. However, the growth of three-dimensional cells requires both physical and chemical signaling. Chemical signaling is generally realized through the constituents of the culture media. Physical signaling to grow cell or tissue cultures requires the use of bioreactors to grow the cell or tissue cultures in the substrates.

Current bioreactors for growing cell tissues are designed with only a single axis of rotation. These single axis rotating bioreactors subject the growing cells on a porous substrate to only a single force vector, thereby providing physical signaling only in the direction of that single force vector. Accordingly, the cells tend not to penetrate throughout the structure of the porous substrate and growth of three-dimensional cell or tissue cultures is inhibited.

Another disadvantage with some bioreactors for growing cell tissues is that they are designed to operate in batch or semi-batch mode.

It is an object of the invention to provide a bioreactor, a system or a method for growing cell or tissue cultures that overcomes or ameliorates at least one of the disadvantages mentioned above.

A further object of the invention is to provide a bioreactor, a system or a method for growing cell or tissue cultures in vitro, that at least partially provide physical signaling in more than one force vector or flow vector or both.

A further object of the invention is to provide a bioreactor, a system or a method for growing three-dimensional cell or tissue cultures in vitro.

SUMMARY

According to a first aspect, there is provided a bioreactor comprising:

a chamber for containing cells or tissue cultures within a culture medium;

a detector capable of detecting a change in one or more metabolites associated with growth of the cell or tissue cultures within the chamber; and a chamber drive capable of rotating the chamber at a first speed about a first axis and a second speed about a second axis, the second axis being disposed at an angle relative to the first axis, wherein in use, the magnitude of the first speed and the second speed are independently variable of each other.

In one embodiment, the angle between the first axis and the second axis is about 90 degrees. In another embodiment, the angle between the first and second axes is in the range selected from the group consisting of: 60° to 120°; 70° to 110°; 80° to 100°; 85° to 95°; and 88° to 92°.

The or more metabolites may be selected from the group consisting of: dissolved oxygen, dissolved carbon dioxide, glucose, lactate, glutamine, amino acids, lipids, carbohydrates, pyruvate, soluble proteins, cytokines and free radicals.

The bioreactor may comprise a sensor capable of detecting at least one of pH, temperature and forces applied to the chamber as it rotates about the first and second axes.

The chamber drive may be capable of rotating the chamber at a third speed about a third axis, the third axis being disposed at a second angle relative to the first axis. The magnitude of the third speed may be independently variable of the first and second speeds. The angle between the first and third axes may be in the range selected from the group consisting of: 60° to 120°; 70° to 110°; 80° to 100°; 85° to 95°; and 88° to 92°.

The bioreactor may comprise a fluidly sealed inlet passage extending into the chamber for passage of feed material into the chamber; and a fluidly sealed outlet passage extending into the chamber for passage of feed material out of the chamber.

The bioreactor may comprise a controller for controlling one or more variables selected from the group consisting of: temperature, dissolved oxygen, glucose, pH, lactate, glutamine, amino acids, lipids, carbohydrates, pyruvate and combinations thereof. The bioreactor may also comprise an adjustment mechanism capable of adjusting the angle between the second axis and the first axis.

The chamber may be substantially spherical or substantially elliptical in shape. The chamber drive may comprise one or more servo motors capable of rotating the spherical or elliptical shaped chamber about at least one of the first axis, the second axis and the third axis.

In one embodiment, the chamber drive may be capable of rotating the chamber about an arc of rotation. The arc of rotation of the chamber may be selected from the group consisting of: 20° to 180°, 30° to 150°, 45° to 120°, and 45° to 90°. Accordingly, the chamber rotates about at least one of the first and second axes in a first direction before rotating in an opposite direction about one of the first and second axes.

In another embodiment, the chamber drive is capable of rotating the chamber continuously about at least one of the first axis and the second axis.

The bioreactor may further comprise a compressor in fluid communication with said chamber, wherein in use, said compressor modulates the pressure within the chamber. The pressure may be selected from the group consisting of 0 KPa to 3000 KPa, 50 KPa to 1500 KPa, 50 KPa to 1000 KPa, and 50 KPa to 500 KPa.

According to a second aspect, there is provided a method for growing cell or tissue cultures in vitro comprising the steps of:

(a) providing a chamber having a cell or tissue culture within a culture medium;

(b) rotating the chamber about a first axis at a first speed; and (c) rotating the chamber about a second axis at a second speed, wherein the second axis is disposed at an angle relative to the first axis and wherein the magnitude of the first speed and the second speed are independently variable of each other.

The method may further comprise the step of:

(d) detecting a change in one or more metabolites associated with growth of the cell or tissue culture within the chamber. The detecting step (d) may comprise the step of:

(d1) detecting said one or more metabolites from the group consisting of: dissolved oxygen, glucose, lactate, glutamine, amino acids, lipids, carbohydrates, pyruvate, soluble proteins, cytokines and free radicals.

The rotating step (c) may further comprise the step of:

(c1) rotating the chamber at a third speed about a third axis, the third axis being disposed at a second angle relative to the first axis.

The method may further comprise the step of:

(e) maintaining the chamber at a pressure higher than ambient pressure during cell or tissue growth.

The maintaining step (e) may comprise the step of:

(e1) maintaining the pressure within chamber selected from the group consisting of:

The rotating step (c) may further comprise the step of:

(c1) rotating the chamber about an arc selected from the group consisting of: 20° to 180°, 30° to 150°, 45° to 120°, and 45° to 90°.

The rotating step (c) may further comprise the step of:

(c2) rotating the chamber continuously about at least one of the first axis and the second axis.

According to a third aspect, there is provided the use of a bioreactor for growing cells and tissue cultures, the bioreactor comprising:

a chamber for containing cell or tissue culture within a culture medium; and a chamber drive capable of rotating the chamber at a first speed about a first axis and a second speed about a second axis, the first axis being disposed at an angle relative to the second axis, wherein in use, the magnitude of the first speed and the second speed are independently variable of each other. In the use aspect, the chamber drive may be capable of rotating the chamber at a third speed about a third axis, the third axis being disposed at a second angle relative to the first axis.

According to a fourth aspect, there is provided a bioreactor comprising:

a substantially spherical or substantially elliptical shaped chamber capable of containing cell or tissue culture within a culture medium;

a chamber support to support the chamber and comprising rollers to allow the chamber to rotate about at least a first axis and a second axis, the first axis being disposed at an angle relative to the second axis; and a chamber drive capable of rotating the chamber at a first speed about the first axis and a second speed about the second axis, wherein in use, the magnitude of the first speed and the second speed are independently variable of each other.

In one embodiment of the third aspect, the chamber drive is capable of rotating the chamber at a third speed about a third axis, the third axis being disposed at a second angle relative to the first axis, and wherein in use, the magnitude of the third speed is independently variable of the first and second speeds.

According to a fifth aspect, the invention provides a dual axis bioreactor for growing cell or tissue cultures comprising:

a chamber for containing a cell or tissue culture and a culture medium for growing cell or tissue cultures;

a drive mechanism for rotating the chamber at a first speed about a first axis and at a second speed about a second axis, the second axis being substantially normal relative to the first axis, wherein the magnitude of the first speed and the second speed are independently variable of each other to thereby grow a cell or tissue culture within the chamber.

Suitably, the dual axis bioreactor further comprises:

a first rotatable member rotatable about the first axis and coupled to the chamber for rotating the chamber about the first axis; and a second rotatable member rotatable about the second axis, the second rotatable member coupled to the chamber for rotating the chamber about the second axis.

Suitably, the dual axis bioreactor further comprises at least one fluid connector comprising:

a stationary casing;

a rotatable shaft mounted to the stationary casing, the shaft rotatable about a shaft axis in axial alignment with, or axially offset from, either the first or second axes; and at least one fluidly sealed passage defined between the juncture of the stationary casing and the rotatable shaft and extending through the casing and the rotatable shaft, wherein the fluidly sealed passage allows passage of fluid from or to the chamber, or both, as the shaft rotates about the shaft axis.

Suitably, the dual axis bioreactor further comprises a heater element that is thermally coupled to the chamber for heating material within the chamber. The heater element may be disposed adjacent to an outer surface of the chamber.

In one embodiment, the dual axis bioreactor further comprises one or more detector elements for detecting a variable of the material within the chamber. The variable of the material within the chamber may be selected from the group consisting of: pH; temperature; dissolved oxygen content; and one or more combinations thereof.

In another embodiment the dual axis bioreactor further comprises a force detector for detecting the force applied to the chamber as it rotates about the first axis or the second axis, or both.

Suitably, one fluidly sealed passage is provided in the fluid connector for passage of feed material to the chamber, and another fluidly sealed passage is provided in the fluid connector for passage of product material from the chamber.

Suitably, the dual axis bioreactor further comprises an adjustment mechanism provided on the first rotatable member or the second rotatable member for respectively adjusting the position of the chamber relative to the second axis or the first axis.

In a preferred embodiment, the drive mechanism includes at least one motor that is coupled to the first or second rotatable members, or both, by at least one drive shaft.

In a preferred embodiment, the drive mechanism includes:

a first motor coupled to the first rotatable member by an outer drive shaft having a hollow passage extending through its axis; and a second motor coupled to the second rotatable member by an inner drive shaft disposed at least partly within the hollow passage of the outer drive shaft.

In a preferred embodiment, the drive mechanism includes:

a first motor coupled to the first rotatable member by a first drive shaft; and a second motor disposed within, or on, the second rotatable member and coupled to the second rotatable member by a second drive shaft.

Suitably, the first and second motors are servo motors.

In a preferred embodiment, the drive shaft is coupled to the motor by a gear train for controlling the speed of rotation of the shaft.

In a preferred embodiment, the chamber further comprises a feed conduit for passage of feed media into the chamber and an outlet conduit for passage of product material from the chamber.

According to a sixth aspect, there is provided a method for growing cell or tissue cultures in vitro comprising the steps of:

(a) providing a chamber having a cell or tissue culture and a culture medium;

(b) rotating the chamber about a first axis at a first speed; and (c) rotating the chamber about a second axis at a second speed, the second axis being substantially normal to the first axis and wherein the magnitude of the first speed and the second speed are independently variable of each other to thereby grow a cell or tissue culture.

According to a seventh aspect, there is provided a system for growing cell or tissue cultures in vitro comprising:

a bioreactor comprising a chamber for containing a cell or tissue culture and a culture medium for growing cell or tissue cultures;

a drive mechanism for rotating the chamber at a first speed about a first axis and at a second speed about a second axis, the second axis being substantially normal relative to the first axis; and a controller for controlling the operation of the drive mechanism, wherein the magnitude of the first speed and the second speed are independently variable of each other to thereby grow a cell or tissue culture within the chamber.

According to a eighth aspect, there is provided a continuous flow dual axis bioreactor for growing cell or tissue cultures comprising:

a chamber for containing a cell or tissue culture and a culture medium;

a first rotatable member rotatable about a first axis, the first rotatable member coupled to the chamber for rotating the chamber about the first axis in use;

a second rotatable member rotatable about a second axis, the second axis being substantially normal relative to the first axis, the second rotatable member coupled to the chamber for rotating the chamber about the second axis;

a drive mechanism for rotating the first rotatable member at a first speed about the first axis and the second rotatable member at a second speed about the second axis, wherein the magnitude of the first speed and the second speed are independently variable of each other to thereby grow a cell or tissue culture within the chamber; and a fluid connector for providing fluid material passage to and from the chamber.

According to a ninth aspect, there is provided a cell or tissue culture when grown in vitro by the method of the second aspect. According to a tenth aspect, there is provided a three-dimensional cell or tissue culture when grown in vitro by the method of the second aspect.

DEFINITIONS

The following words and terms used herein shall have the meaning indicated:

The word "metabolite" and grammatical variations thereof as used herein, refers to any substance produced by, or used in, metabolism or a metabolic process. Exemplary metabolites include dissolved oxygen, dissolved carbon dioxide, glucose, lactate, glutamine, amino acids, lipids, carbohydrates, pyruvate, soluble proteins, cytokines, free radicals, and combinations thereof.

The word "fluid" and the term "fluid material" are to be interpreted broadly to include not only liquid and gas phase materials but also slurries that comprise solid or semi-solid material suspended in a liquid phase.

The term "feed material" is to be interpreted broadly to include a liquid phase or a gas phase material or a slurry that comprises solids or semi-solids suspended in a liquid phase, and combinations of one or more phases thereof, which is used to facilitate the growth of cell or tissue cultures.

The words "culture medium" or "culture media": are to be interpreted broadly to include any medium that facilitates the growth of cell and tissues.

The term "product material" is to be interpreted broadly to include a liquid phase or a gas phase material or a slurry that comprises solids suspended in a liquid phase, and combinations of one or more phases thereof, which includes one or more reactant products, by-products or intermediate products produced as a result of the growth of cell or tissue cultures.

The terms "three-dimensional matrix" or "three-dimensional matrices": are to be interpreted broadly to include any (a) any material and/or shape, including gels, beads, porous meshes, scaffolds, that have three dimensions and which allow cells to attach to it (or can be modified to allow cells to attach to it); and (b) allows cells to grow in more than one layer.

The words "matrix" or "matrices": are to be interpreted broadly to include any (a) any material and/or shape, including gels, beads, porous meshes, scaffolds, which allow cells to attach to it (or can be modified to allow cells to attach to it).

BRIEF DESCRIPTION OF THE DRAWINGS

Preferred embodiments of the invention will now be described with reference to the following drawings.

FIG. 2 shows a side view of the dual axis bioreactor apparatus of FIG. 1.

FIG. 2a shows a partial cross-sectional view of the dual axis bioreactor shown in FIG. 1 in the plane shown by the direction of arrows AA.

FIG. 3 shows a top view of the dual axis bioreactor apparatus of FIG. 1.

FIG. 16 shows a perspective view of the drive assembly of FIG. 15.

FIG. 17 shows a top view of the drive assembly of FIG. 16.

FIG. 18 shows an end view of the drive assembly of FIG. 16.

FIG. 19 shows a cross sectional view of the drive assembly taken along the arrow lines A-A of FIG. 17.

FIG. 20 shows an exploded perspective view of the drive assembly of the dual axis bioreactor shown in FIG. 15.

FIG. 37a shows a top view of the omni-directional rotary bioreactor apparatus shown in FIG. 35

FIG. 37b shows a front view of the omni-directional rotary bioreactor apparatus of FIG. 35.

FIG. 37c shows a left view of the omni-directional rotary bioreactor apparatus shown in FIG. 35

FIG. 37d shows a right view of the omni-directional rotary bioreactor apparatus of FIG. 35

FIG. 42 is a path-line plot showing the flow regime within the spherical chamber of FIG. 40.

FIG. 43 is a path-line plot showing the flow regime within the cylindrical chamber of FIG. 1

DETAILED DESCRIPTION OF PREFERRED EMBODIMENTS OF THE INVENTION

Embodiment 1

Dual Axis Bioreactor

Figure 1:
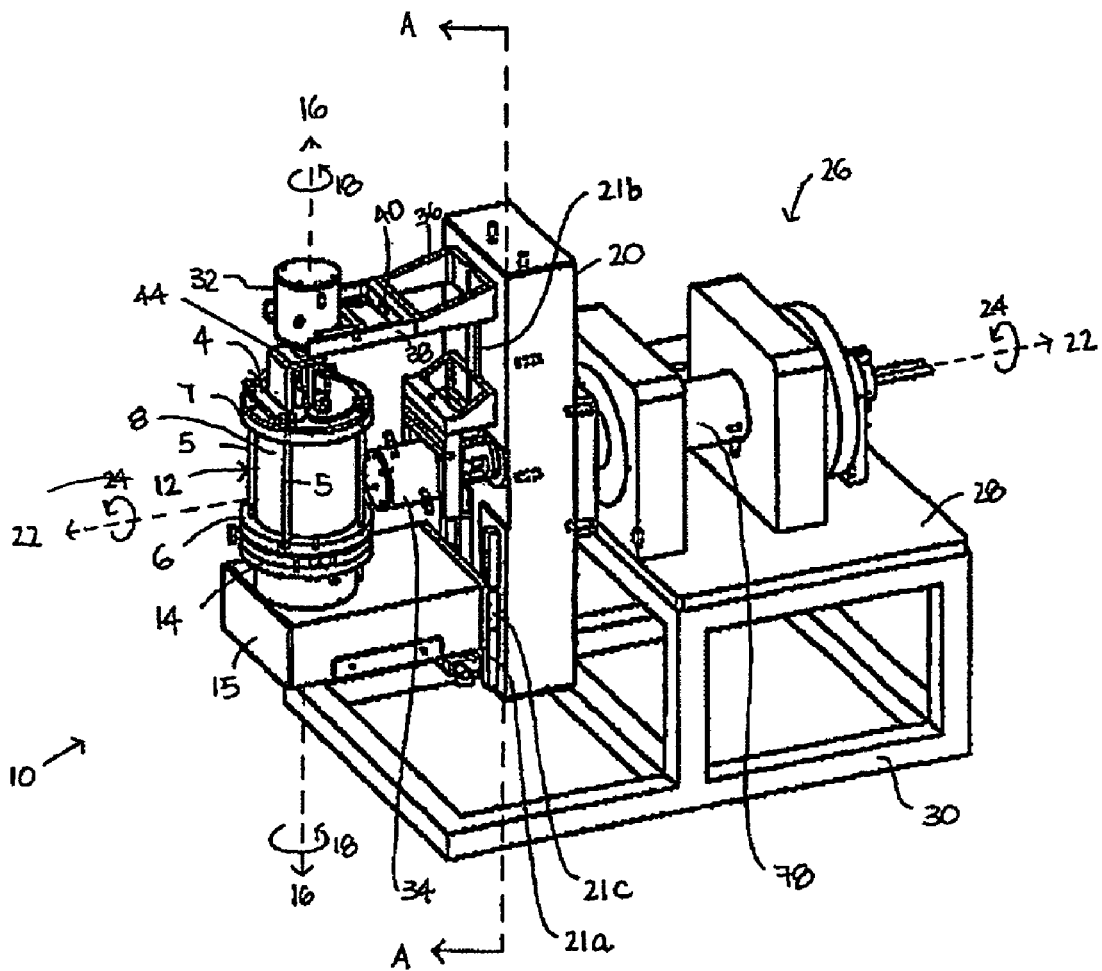
FIG. 1 shows a perspective view of a dual axis bioreactor apparatus in accordance with one embodiment.

FIG. 1 shows a perspective view of a first preferred embodiment of a dual axis bioreactor 10 that is used to grow cell or tissue cultures. The bioreactor 10 includes a chamber 12 for containing a cell or tissue culture and a culture medium for growing cell or tissue cultures in use. The bioreactor 10 also includes a drive mechanism 26 for rotating the chamber 12 at a first speed about a first vertical axis 16 and at a second speed about a second horizontal axis 22. The horizontal axis is normal relative to the vertical axis. As will be described further below, in use, the magnitude of the first speed and the second speed are independently variable of each other to thereby grow a cell or tissue culture within the chamber.

Referring to FIGS. 1, 2, 2a, 3, the chamber 12 may be provided with a three-dimensional matrix (not shown) when growing three-dimensional cell or tissue cultures as will be described further below. The chamber 12 includes a glass tube 8 having two open ends that are respectively clamped between a top flange 7 and a bottom flange 6 by four evenly spaced rods 5 fixed by a knurled locking nut and bolt arrangement 4.

In this embodiment, the top flange 7 and the bottom flange 6 are manufactured from stainless steel. Referring to FIG. 2a, it can be seen that the chamber 12 further includes seals 6a and 7a respectively provided between the ends of the glass tube 8 and between the bottom flange 6 and top flange 7.

Figure 5:
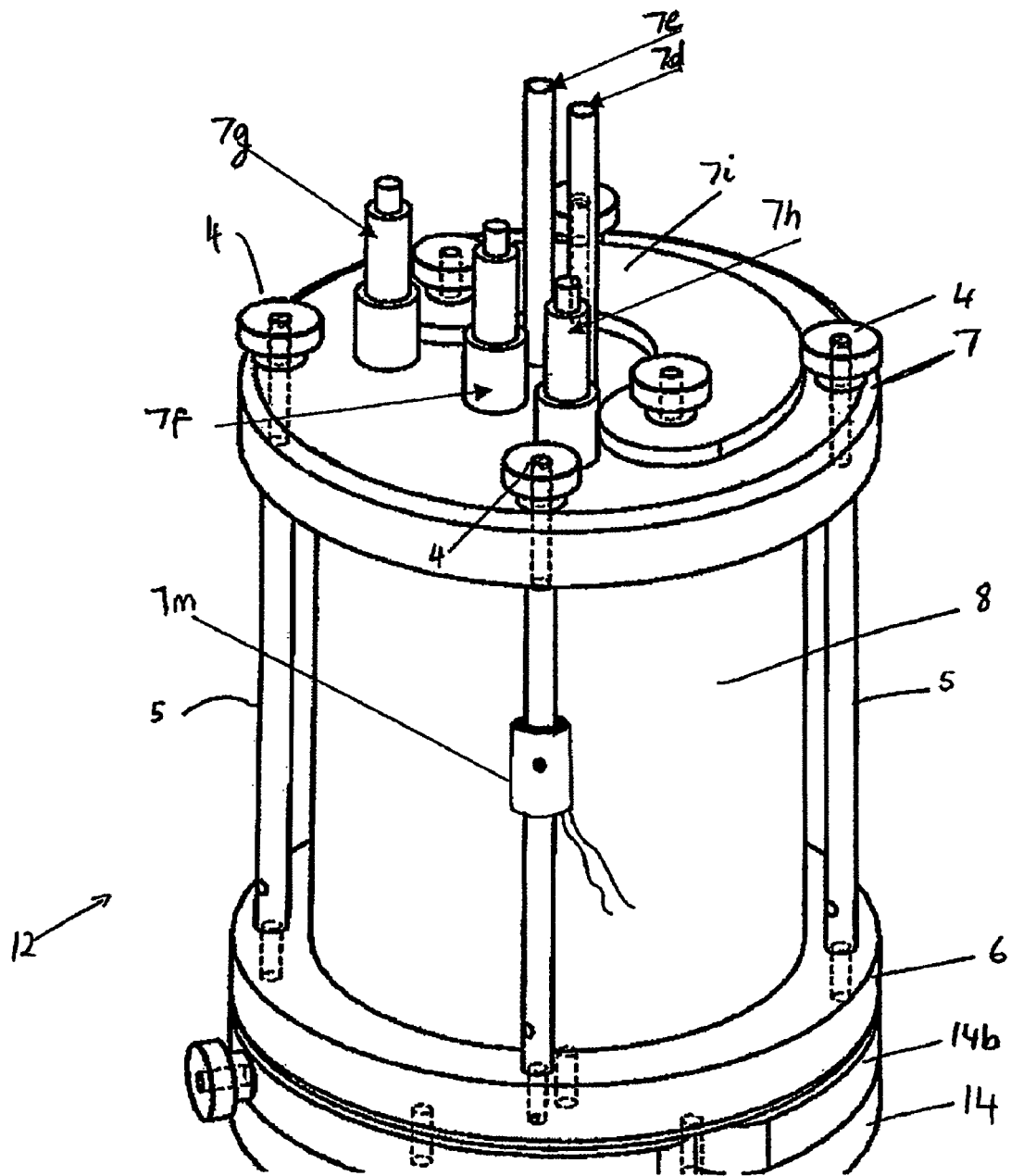
FIG. 5 shows a more detailed perspective view of the chamber of to the dual axis bioreactor apparatus of FIG. 1.

Referring to FIG. 5, which shows a detailed view of the chamber 12, removal plugs (not shown) are provided in the top flange 7 (refer to FIG. 15) for insertion and retrieval of fluid material within the chamber 10 that is used to grow the cell tissue cultures. The holes into which the removal plugs are inserted are used as conduits for respectively allowing passage of fluid material into and out of the chamber 12.

In this embodiment, two stainless steel tubes 7d,7e are provided to extend through the conduits of the flange 7 and thereby respectively provide a conduit for passage of fluid material into and out of the chamber 12. The flange 7 is also provided with detectors for detecting process variables associated with the fluid material within chamber 12. The detectors in this embodiment include a temperature sensor 7f for measuring the temperature of the fluid material, dissolved oxygen sensor 7g for measuring the dissolved oxygen content of the fluid material, and a pH sensor 7h for measuring the pH of the fluid material.

Figure 6:
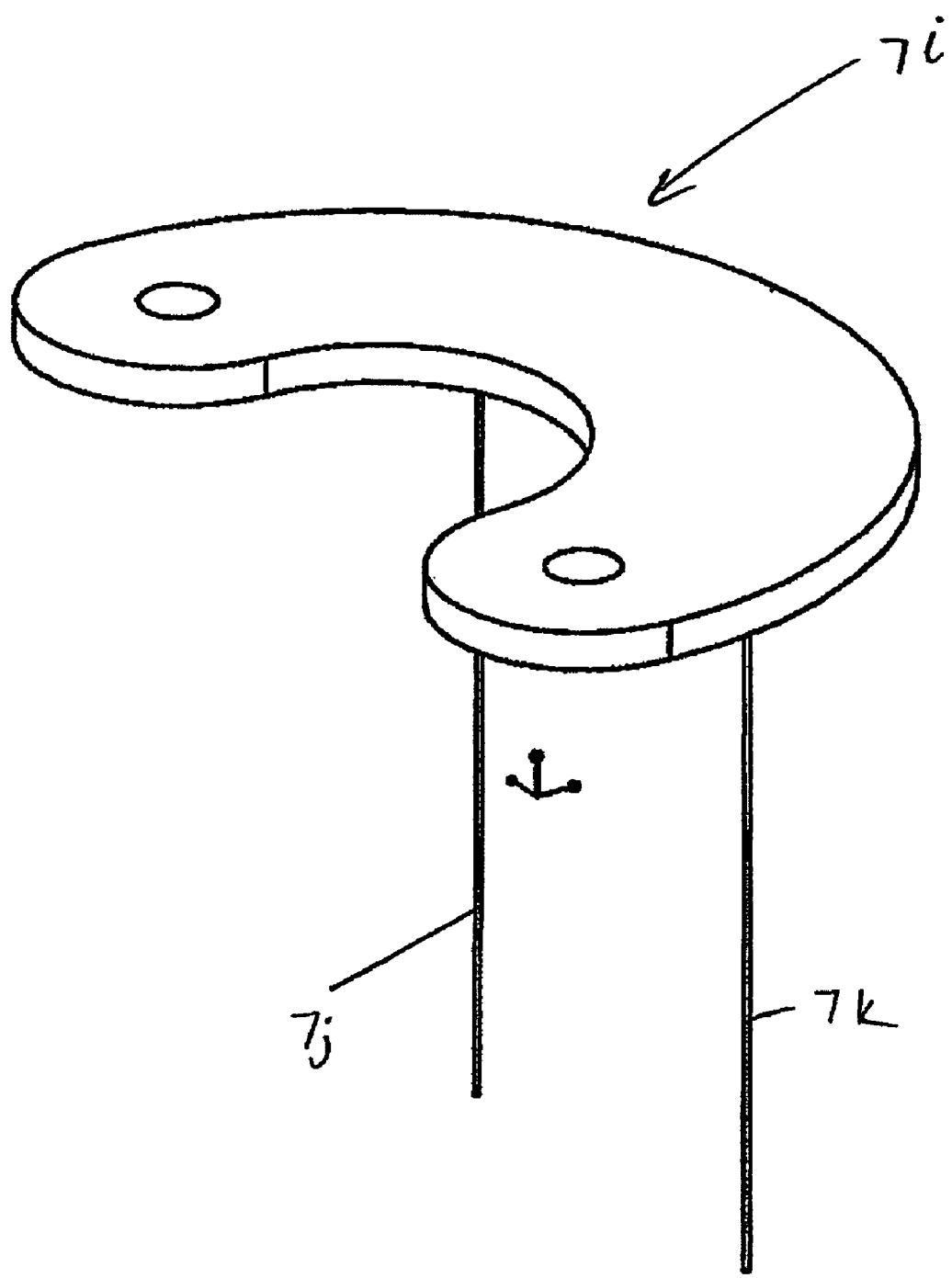
FIG. 6 shows a perspective view of a pair of surgical needles mounted to the clamp cover of the chamber of the dual axis bioreactor apparatus of FIG. 1.
Figure 7:
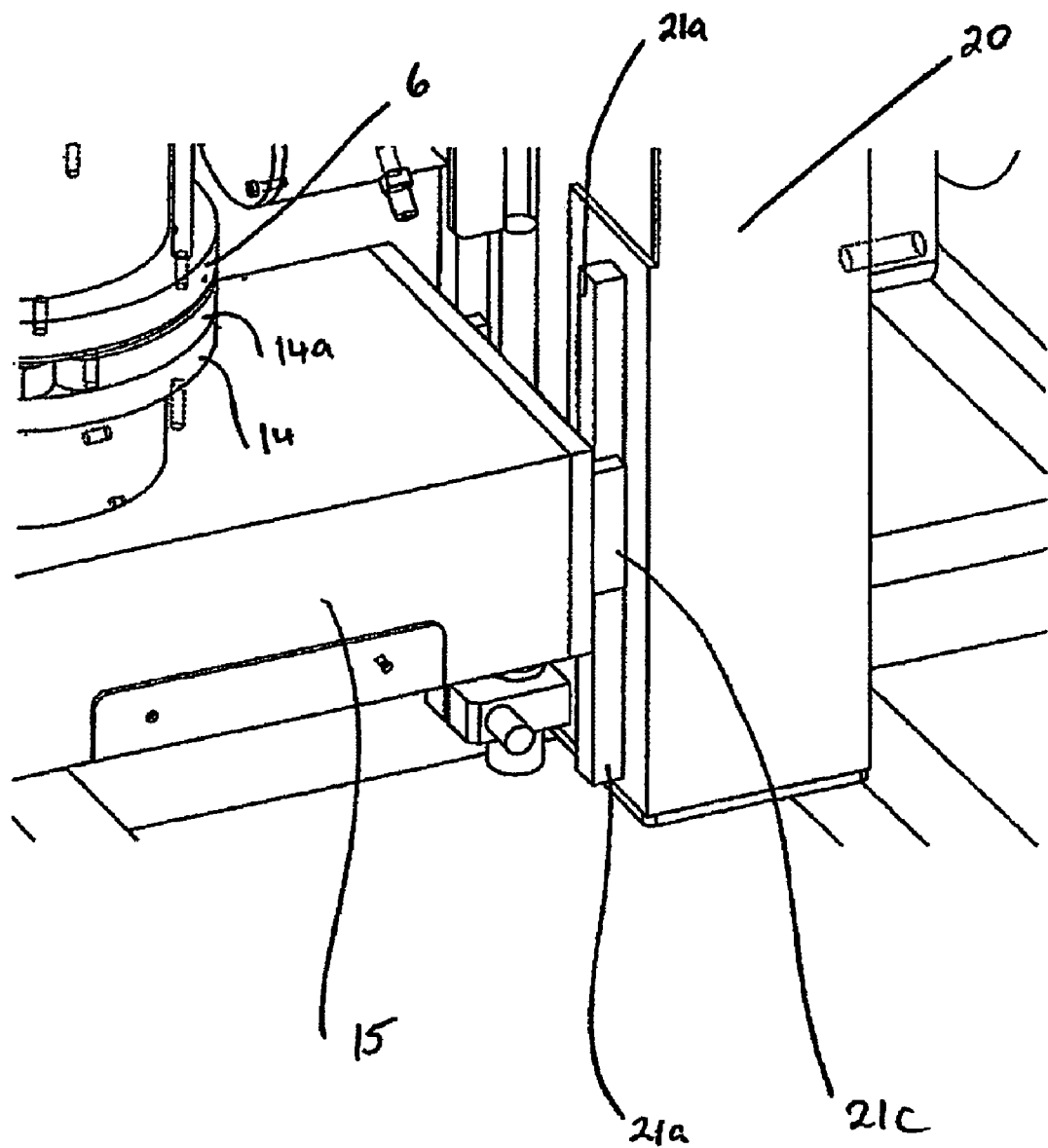
FIG. 7 shows a detailed perspective view of an adjustment mechanism mounted to the dual axis bioreactor apparatus of FIG. 1.

The flange 7 is also provided with a chamber cover 7i for introducing a three dimensional matrix or a scaffold into the chamber 12. A more detailed view of the chamber cover 7i can be seen in FIG. 6, which shows a perspective view of the chamber cover 7i when disassembled from the chamber 12. The chamber cover 7i includes a mount for retaining a scaffold in the form of a pair of surgical needles 7j,7k, which are used to impale a three-dimensional matrix onto in use. The three-dimensional matrix can be any kind of porous scaffold and is used to provide an attachment structure for the grows of three-dimensional cell cultures and tissues thereon in use.

Referring to FIG. 5, the flange 7 also has a force detector 7m, which attached to its surface for detecting centripetal and centrifugal forces applied to the chamber 12 as it rotated about vertical axis 16 and horizontal axis 22.

Referring now again to FIGS. 1-2,2a and 3, the bioreactor 10 also includes a first rotatable member in the form of rotary plate 14 that is mounted on a rotor 13 of (refer to FIG. 2a) a servo-motor 86b. The rotary plate 14 is rotatable about a vertical axis as shown generally by dashed arrow 16, in the direction of arrow 18. It should be realized that in other embodiments, the rotary plate 14 may rotate about the vertical axis in an opposite direction to the direction of arrow 18. The rotary plate 14 is clamped by the bottom flange 6 of the chamber 12 so that when in use, the rotary plate 14 rotates the chamber 12 about the vertical axis 16.

Referring now to FIG. 2a, the bioreactor also includes a heater element in the form of two heating cartridges 6b mounted within rotary plate 14. Bracket 14a of flange 6 sits on rotary plate 14 and is locked thereto by brace 14b (refer to FIGS. 4-5). The heating cartridges 6b are thermostatically controlled by a controller for maintaining the temperature within the chamber 12 during use. The heating cartridges 6b within heater plate 14a is provided adjacent to the bottom of the chamber 12 to effect efficient heating of the fluid material within the chamber 12.

Figure 53:
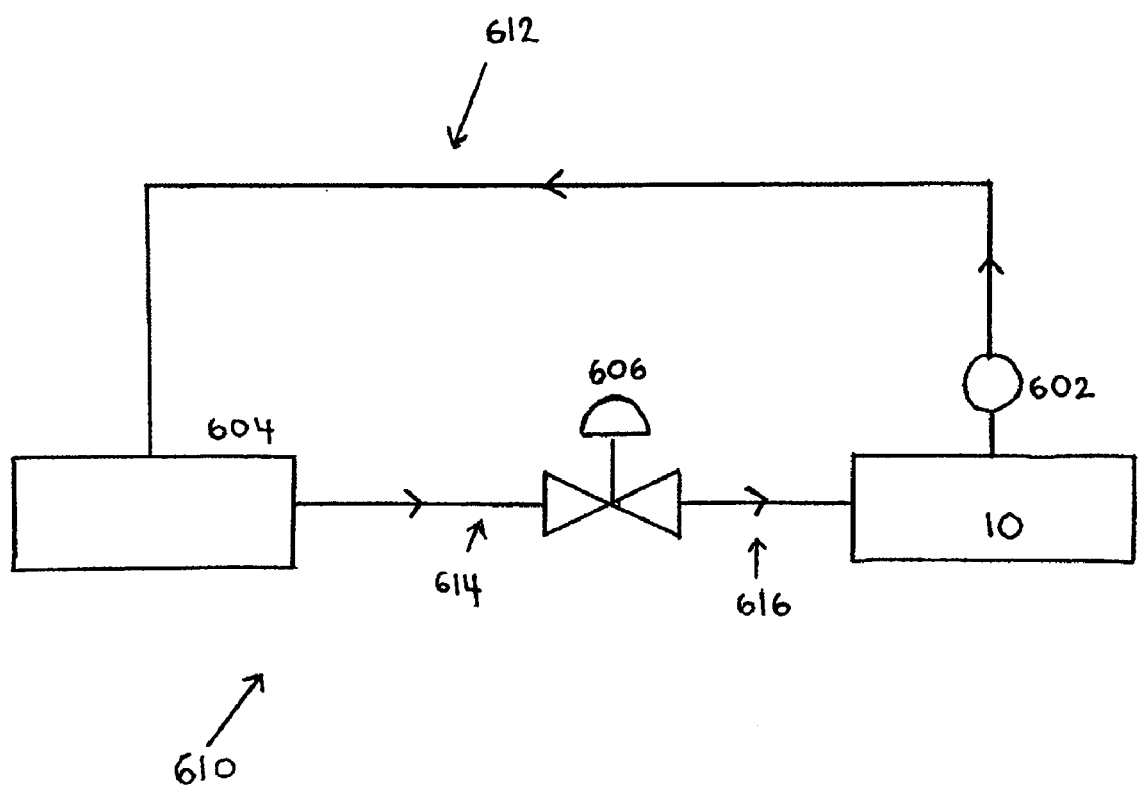
FIG. 53 shows logical diagram of a controller circuit for controlling a parameter related to growth of a cell or tissue in a bioreactor.

FIG. 53 shows a logical diagram of a control circuit used to control a parameter related to growth of cell or tissue culture within the chamber. In a particular embodiment, the parameter is dissolved oxygen.

In this particular embodiment, the bioreactor 10 is provided with a dissolved oxygen detector 602. The dissolved oxygen detector 602 is connected by means of copper wires 612 to a PID (proportional integral derivative) controller 604. The PID controller 604 is further connected, via copper wires 614, to a final control by means in the form of gate valve 606. The gate valve 606 is capable of regulating the flow of oxygen into the bioreactor 10.

In use, the dissolved oxygen detector 602 measures a change in dissolved oxygen concentration and sends a corresponding electrical signal to the PID controller 604. The PID controller calculates the offset between the set value and the signal from the detector 602. The PID controller then generates an appropriate error signal proportional to the offset. The error signal is transmitted to the gate valve 606 by means of the copper wires 614. The gate valve 606 operates according to the error signal and the offset is thereby reduced to nearly zero. For example, when the dissolved oxygen concentration is lower than the set value, a positive error signal (set value— signal of the detector 602) is generated by the PID controller. In response to a positive error signal, the gate valve 606 is opened, thereby pumping more oxygen into the bioreactor until the dissolved oxygen concentration reaches to the set value.

The bioreactor 10 includes a second rotatable member in the form of rotary L-shaped bracket 20. The L-shaped bracket 20 includes a horizontal support arm 15 having a longitudinal axis that is in alignment with, but offset from, the horizontal axis 22. Rotary L-shaped bracket 20 is rotatable about a horizontal axis as shown generally by dashed arrow line 22, in the direction of arrow 24. It should be realized that in other embodiments, the rotary L-shaped bracket 20 may rotate about the horizontal axis 22 in an opposite direction to the direction of arrow 24.

In this embodiment, the horizontal axis 22 is at a right angle relative to the vertical axis 16. It should be appreciated however, that the vertical axis 16 may not be at a right angle relative to the horizontal axis 22 but may extend anywhere within an arc covering the range of 60° to 120° relative to the horizontal axis.

Referring to FIG. 2a, the rotary drive 13 is mounted to the support arm 15 of the rotary L-shaped bracket 20, and provides a support for the rotary plate 14 so that, as will be described further below, the rotary L-shaped bracket 20 rotates the chamber 12 about the horizontal axis 22.

The drive mechanism 26 is mechanically coupled to the rotary L-shaped bracket 20 and the rotary drive 13 to simultaneously rotate the chamber 12 about the horizontal axis 22 and the vertical axis 16 and thereby subject a growing cell or tissue culture within the chamber 12 to two force vectors in order to propagate a three-dimensional cell or tissue culture.

In other embodiments, it should be realized that periodic or sequential rotation of the rotary L-shaped bracket 20 and the rotary drive 13 may occur rather than simultaneous rotation when growing cell or tissue cultures.

The drive mechanism 26 is supported on a base plate 28, which is connected to frame 30. The frame 30 is shaped such that the base plate 28 is at a height from the ground such that it is sufficient to allow the rotary L-shaped bracket 20 to rotate about the horizontal axis 22 without interference.

Referring to FIGS. 1-2,2a,7 and 8, tracks 21a, 21b are provided on the rotary L-shaped bracket 20. The tracks 21a, 21b are shaped such that they allow guides 21c that are provided on the support arm 15 and the bracket 36 to travel thereon. The guides are provided with a locking mechanism 21h that locks the support arm 15 and the bracket 36 in a desired position during use.

Figure 8:
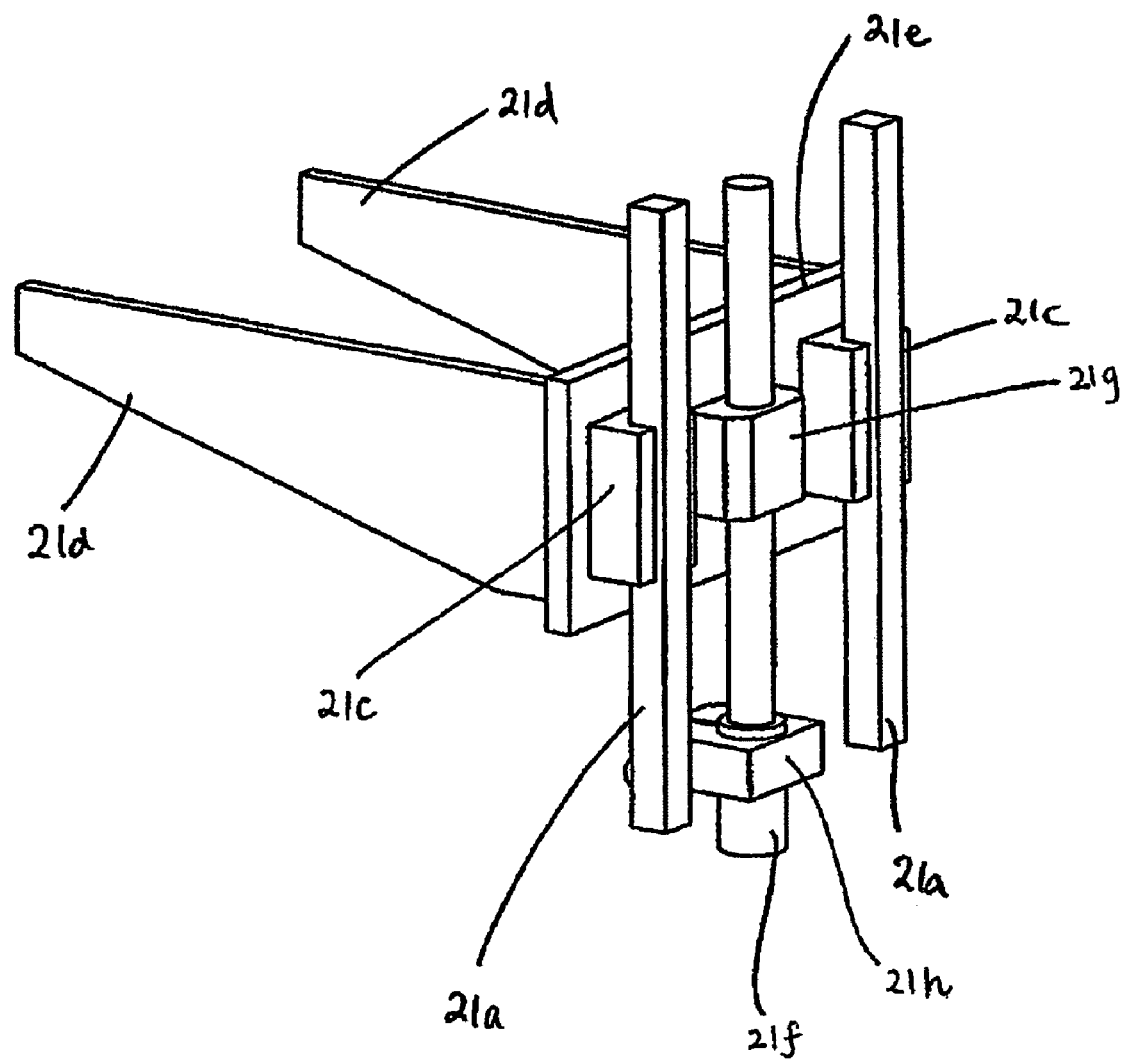
FIG. 8 shows a perspective view of the adjustment of FIG. 7 disassembled from the dual axis bioreactor.

Referring now to FIG. 8, there is shown a view of two tracks 21a and guides 21c when disassembled from the dual axis bioreactor 10. The guides 21c are mounted to a plate 21e that has two extending arms 21d extending from the face of the plate 21e to form a yoke that mounts to the support arm 15.

A lead screw shaft 21f is disposed between the tracks 21A and is connected to the plate 21e by a lead screw nut 21g. It will be appreciated that the support arm 15 and the bracket 36 are moveable along the vertical axis 16 by actuating the lead screw nut 21g along the lead screw shaft 21f to so that the position of the chamber 12 and the connector 32 can be varied with reference to the horizontal axis 22. Accordingly, a user is able to change the centrifugal and centripetal forces acting on the growing cells or tissues within the chamber 12.

Referring again to FIGS. 1-3, the drive mechanism 26 of the bioreactor 10, includes a main drive shaft 78, which extends through two mounting plates 80a,80b attached to base plate 28. The drive shaft 78 extends through the mounting plate 80a and connects to the rotary L-shaped bracket 20 to rotate the arm, in use, about the horizontal axis 22.

The drive mechanism 26 also includes a gear train 82 provided adjacent to mounting plate 80b. The gear train 82 is driven by a rotor 84a that is actuated by servo motors 86a mounted on base plate 28. The servo motors 86a,86b are operated by a controller, as will be described further below. The servo motor 86a drives the drive shaft 78 and hence the rotary L-shaped bracket 20. The drive mechanism also includes the servo motor 86b (refer to FIG. 2a) that is mounted within support arm 15 and has a rotary drive that supports rotary plate 14.

Figure 4:
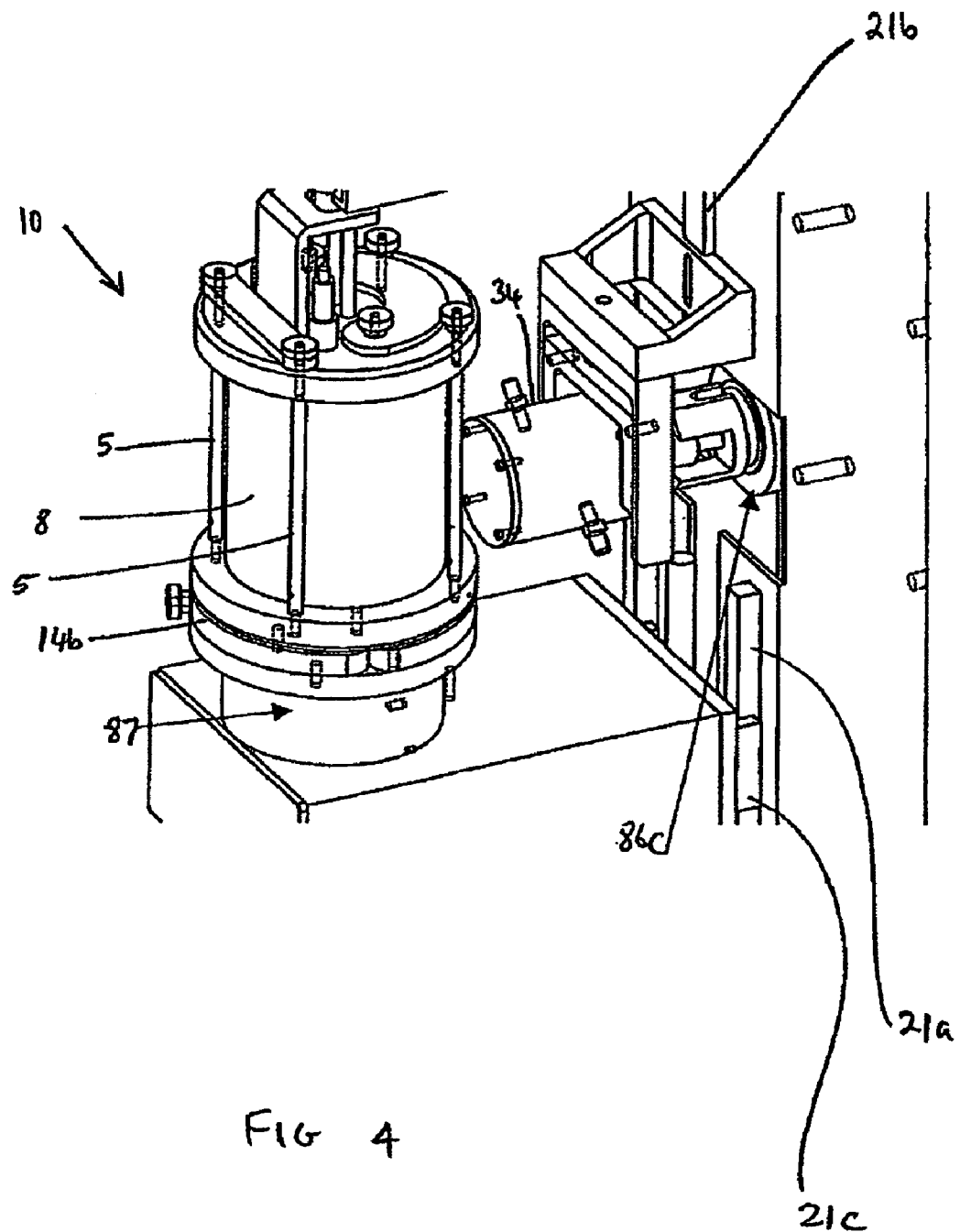
FIG. 4 shows a detailed perspective view of the chamber assembled to the dual axis bioreactor apparatus of FIG. 1.

Referring to FIG. 4, slip-rings are also associated with both servo-motors 86a,86b. The slip-ring associated with the servo-motor 86b is housed within housing 87 and a slip-ring 86c. The slip-rings are provided for command signals to be sent to each of the servo-motors 86a,86b and for data transfer between the servo-motors 86a,86b and the controllers. The slip-ring housed within housing 87 can also be used to provide data transfer from the temperature sensor 7f, dissolved oxygen sensor 7g, pH sensor 7h and force detector 7m mounted to the flange 7. The servo motors 86a,86b are also provided with encoders to monitor the position of the rotors and the encoders send data through the respective slip-rings for control over the bioreactor 10.

The servo-motors 86a and 86b are both brushless servo-motors. The servo-motor 86a is able to operate the rotary L-shaped bracket 20 at a speed in the range between 1 to 80 rpm and at a continuous torque of 5 Nm with a peak of 10 Nm. The servo-motor 86b is able to operate the rotary arm 14 at a speed in the range between 1 to 80 rpm and at a continuous torque of 1 Nm with a peak of 2 Nm.

As can be seen in FIGS. 1,2 and 2a, the bioreactor 10 includes two fluid connectors in the form of pipe connectors 32,34. The pipe connectors 32,34 are "multi-flow" pipe connectors in that they allow passage of fluid material to and from the chamber 12 during use and are provided to prevent entanglement of pipes supplying feed material from a support fermenter to the chamber 12. As will be explained further below, the pipe connectors 32,34 enable the bioreactor 10 to function as a continuous flow bioreactor.

Figure 9:
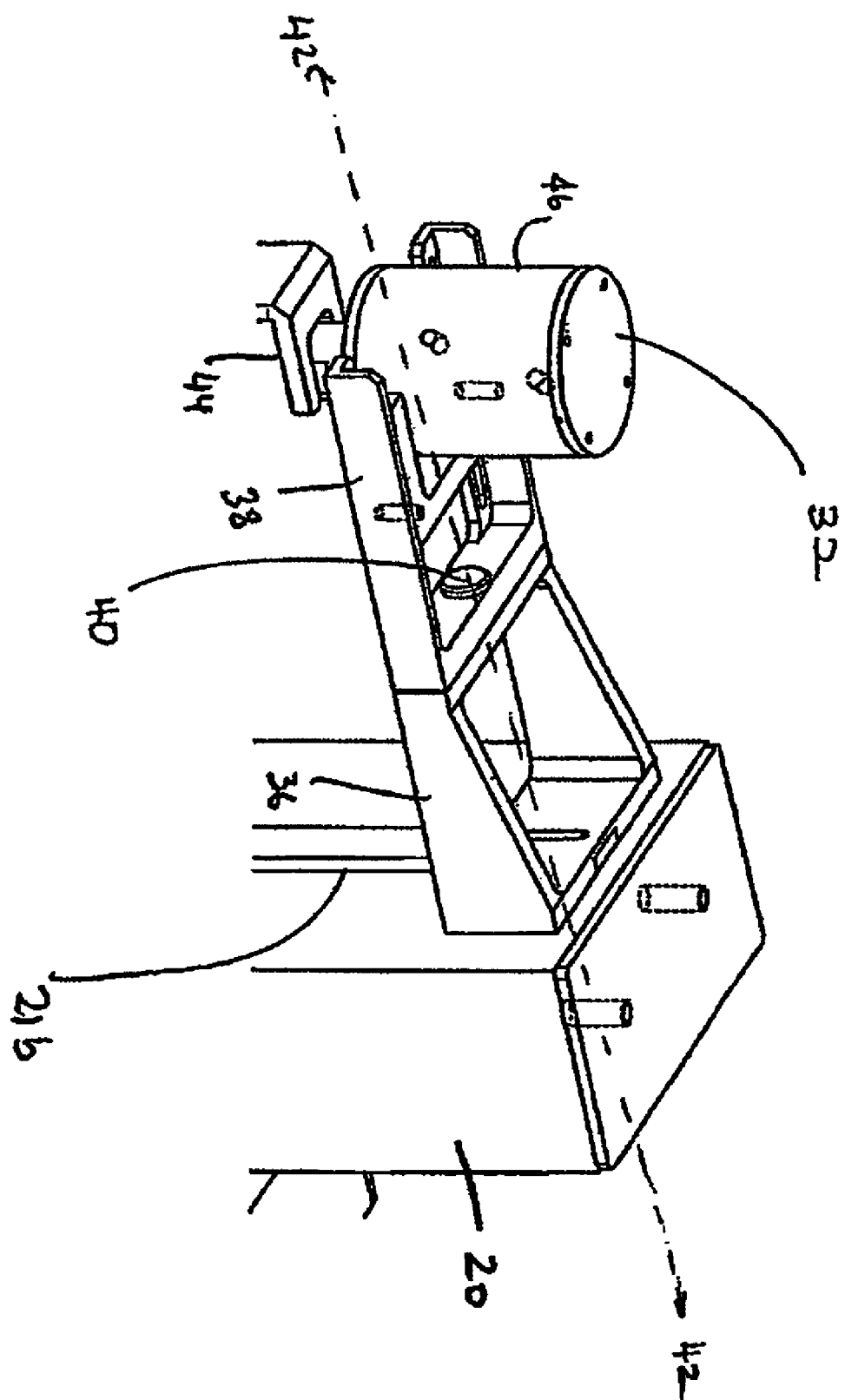
FIG. 9 shows a perspective view of a pipe connector assembled on the dual axis bioreactor shown in FIG. 1.

Referring to FIG. 9, there is shown a detailed perspective view of the pipe connector 32 mounted above the chamber 12 by a yoke 38. The yoke 38 is attached to a bracket 36 by a universal joint 40. The bracket 36 is attached to rotary L-shaped bracket 20. The universal joint 40 allows the connector 32 mounted to the yoke 38 to rotate about a second, horizontal axis 42 that is offset from, but parallel to, the horizontal axis 22. The pipe connector 32 is also mounted to the yoke by a universal joint (not shown) to allow the pipe connector to swivel. The universal joint 40 also provides minimal seal degradation over prolonged use. The pipe connector 32 is attached to the top flange 7 of the chamber 12 by a bracket 44.

The components of the pipe connector 32 will be discussed in detail by referring to FIGS. 10 to 14. It should be understood that the components of the pipe connector 34 are identical to that of pipe connector 32 and the detailed component description of pipe connector 34 is provided merely for convenience.

The pipe connector 32 includes stationary casing in the form of tubular casing 46 having two open ends. The open ends of the casing 46 are clamped between a front flange 48 and a rear flange 50 by a locking nut and bolt arrangement 51.

The pipe connector 32 further includes a rotatable shaft 52 mounted to the casing 46 and extending from the casing 46 via a hole provided in the front flange 48. A front ball bearing 54 is provided adjacent to the inner side of the front flange 48 and a rear ball bearing 55 is provided adjacent to the inner side of the rear flange 50 to allow the shaft 52 to rotate about the shaft axis shown by dashed arrow line 56 in FIG. 12.

Figures 10, 11, 12:
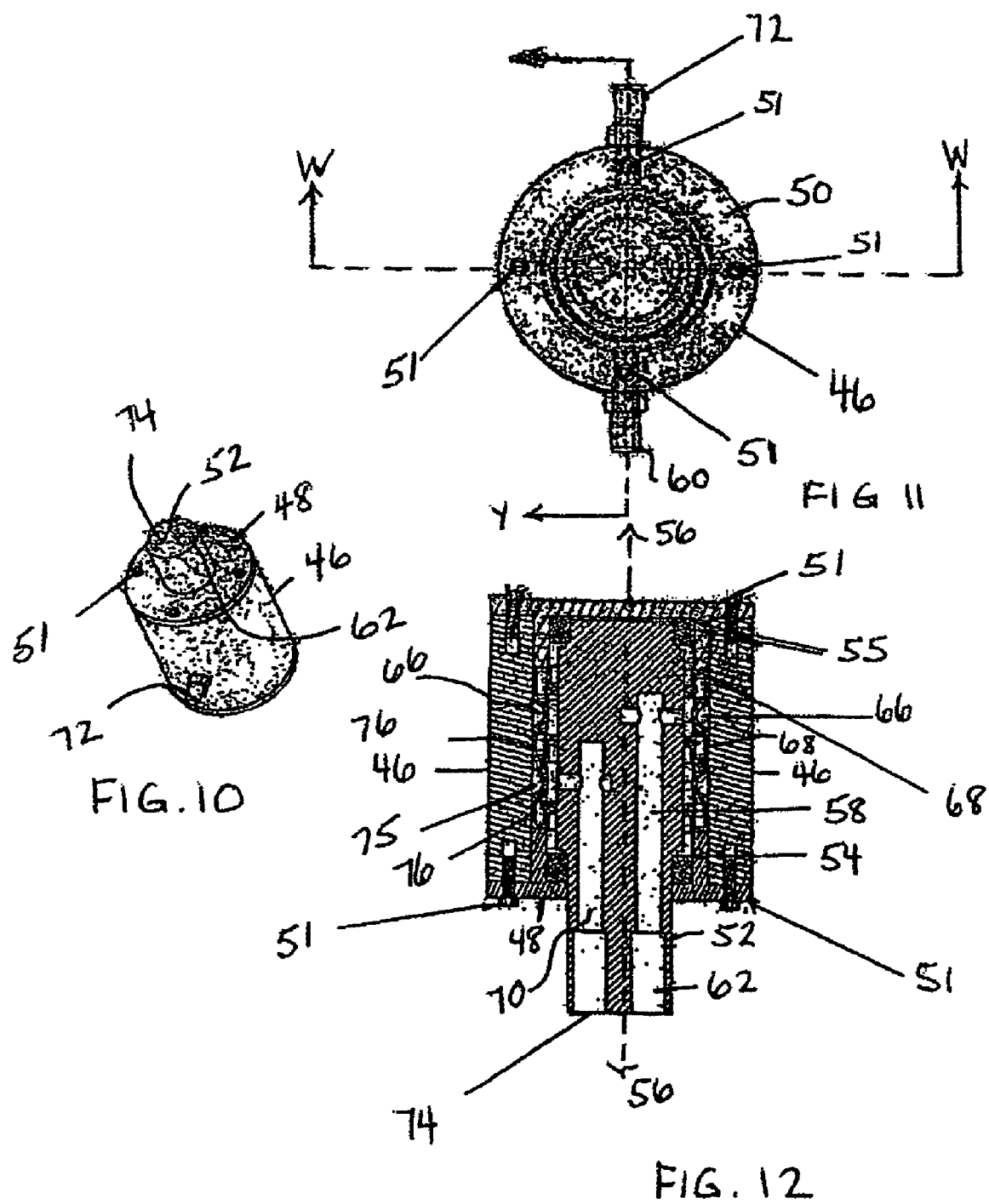
FIG. 10 shows a perspective view of the pipe connector of FIG. 9.
FIG. 11 shows an end view of the pipe connector of FIG. 10.
FIG. 12 shows a section view of the pipe connector taken along the arrow lines W-W shown in FIG. 11.
Figure 13:
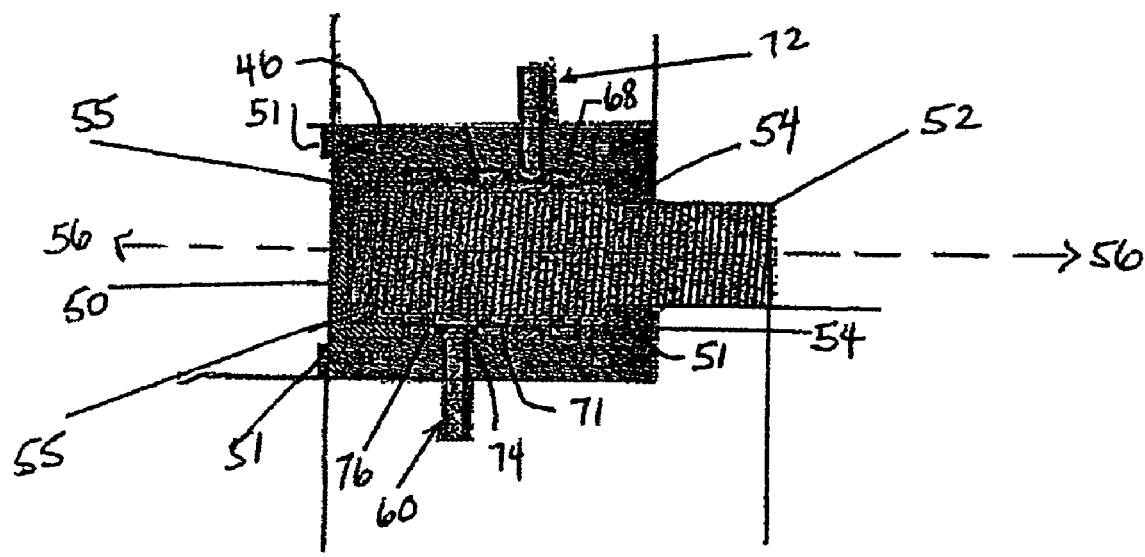
FIG. 13 shows cross-section view of the multi-flow pipe connector taken along the arrow lines Y-Y shown in FIG. 11.
Figure 14:
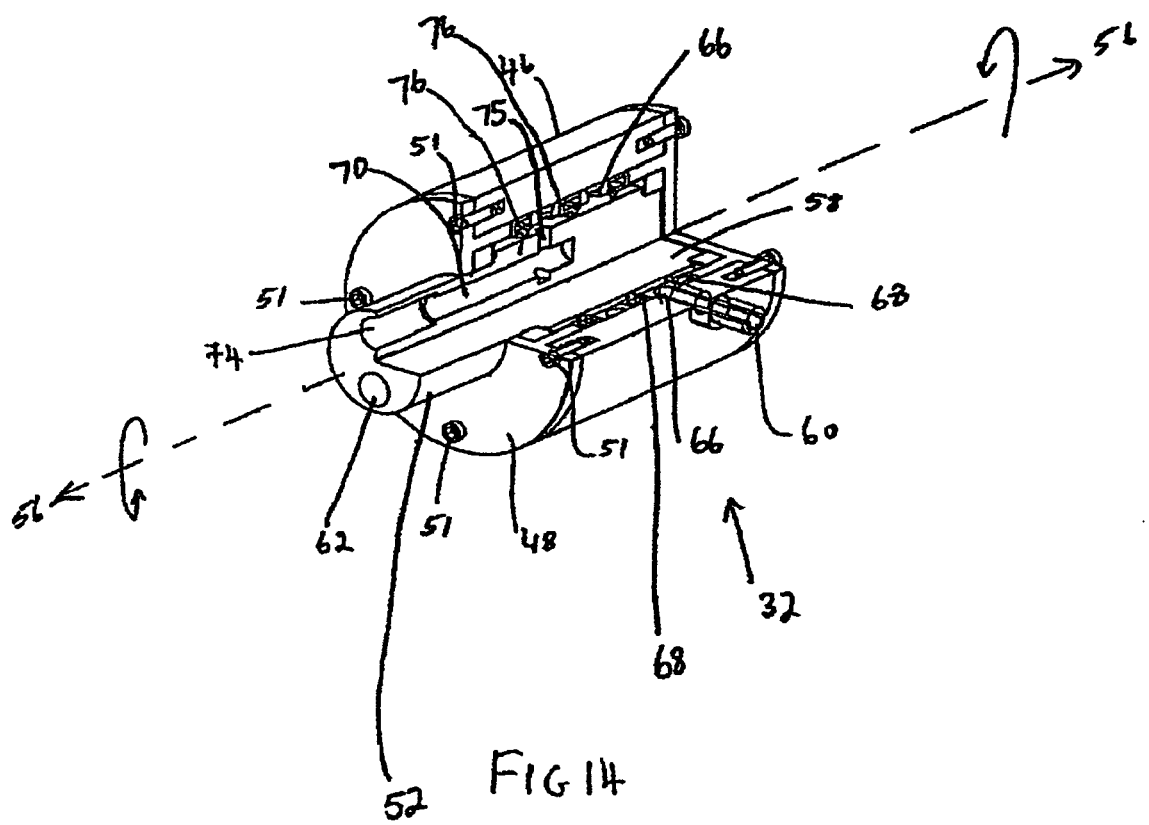
FIG. 14 shows a perspective sectional view of the pipe connector of FIG. 10.

The pipe connector 32 includes a feed material passage in the form of feed conduit 58 extending between inlet nipple 60 (refer to FIG. 13 and FIG. 14) and outlet conduit 62 (refer to FIG. 12 and FIG. 14). The outlet conduit 62 has internal threads to allow for connection with pipe 72a shown in FIG. 2a. The pipe 72a enables the outlet conduit 62 to be in fluid communication with the chamber 12.

As shown in FIGS. 12-14, an inflow cavity 66 extends around the inner wall of the tubular casing 46 and between the shaft 52 and is bound on adjacent sides by a seal in the form of spring-loaded rubber lip oil seals 68.

As the inflow cavity 66 extends around the circumference of the shaft 52, as the shaft 52 rotates about the shaft axis 56, the feed conduit 58 is always in fluid communication with both the inlet nipple 60 and the outlet conduit 62.

The pipe connector 32 includes a product material passage in the form of product conduit 70 extending between outlet nipple 72 (refer to FIG. 13) and inlet conduit 74 (refer to FIG. 12). The inlet conduit 74 has internal threads to allow for connection with a pipe (not shown) that is able to be inserted into a hole provided in the top flange 7 to allow the inlet conduit 74 to be in fluid communication with the chamber 12. In FIG. 12 and FIG. 13, an outflow cavity 75 extends around and between the inner wall of the tubular casing 46 and the shaft 52 and is bound on adjacent sides by another pair of seals in the form of spring-loaded rubber lip oil seals 76. Accordingly, the outflow cavity 75 is fluidly sealed from the inflow cavity 68.

As the outflow cavity 75 extends around the circumference of the shaft 52, as the shaft 52 rotates about the shaft axis 56, the product conduit 70 is always in fluid communication with both the outlet nipple 72 and the inlet conduit 74.

In use, the inlet nipple 60 can be attached to a material feed source, such as a fermenter, to supply feed material to the outlet conduit and ultimately to the chamber 12. Furthermore, the pipe (not shown) connected to the inlet conduit 74 allows product material to be removed from the chamber 12 and transfers it to a product material tank (not shown).

Referring again now to FIGS. 1-3, in this embodiment the shaft axis 56 of pipe connector 32 is co-axial with the vertical axis 16. As the rotary plate rotates about the vertical axis 16, the bracket 44, which is attached to flange 7, engages rotary shaft 52 causing it to turn about the vertical axis 18 in a period that is synchronous with the rotation of the chamber 12 about the vertical axis 16. Accordingly, it will be appreciated that entanglement of the pipes 60a,74a will not occur as a result of this synchronous rotation.

It will be appreciated that the pipe connector 32 allows the bioreactor 10 to function as a continuous flow bioreactor. The ability of the bioreactor 10 to function continuously provides enhanced throughput compared to operating in batch mode. This is particularly advantageous in industrial scale applications where the enhanced throughput enables the realization of efficiencies that may not be achievable in batch operation. Furthermore, the pipe connectors allow continuous re-circulation of media to and from the chamber 12 and a support fermenter as will be described further below.

Referring to FIG. 2a, it can be seen that inlet nipple 60 and outlet nipple 72 of pipe connector 34 are respectively coupled to pipes 60b,72b. Pipes 60b,72b are respectively coupled to like nipples provided on pipe connector 34. This allows like outlet nipples on fluid connector 34 to be connected to inlet and outlet pipe lines in for continuous or re-circulatory flow of material to and from the chamber 12 as the chamber rotates about the horizontal axis 22 and vertical axis 16.

Figure 15:
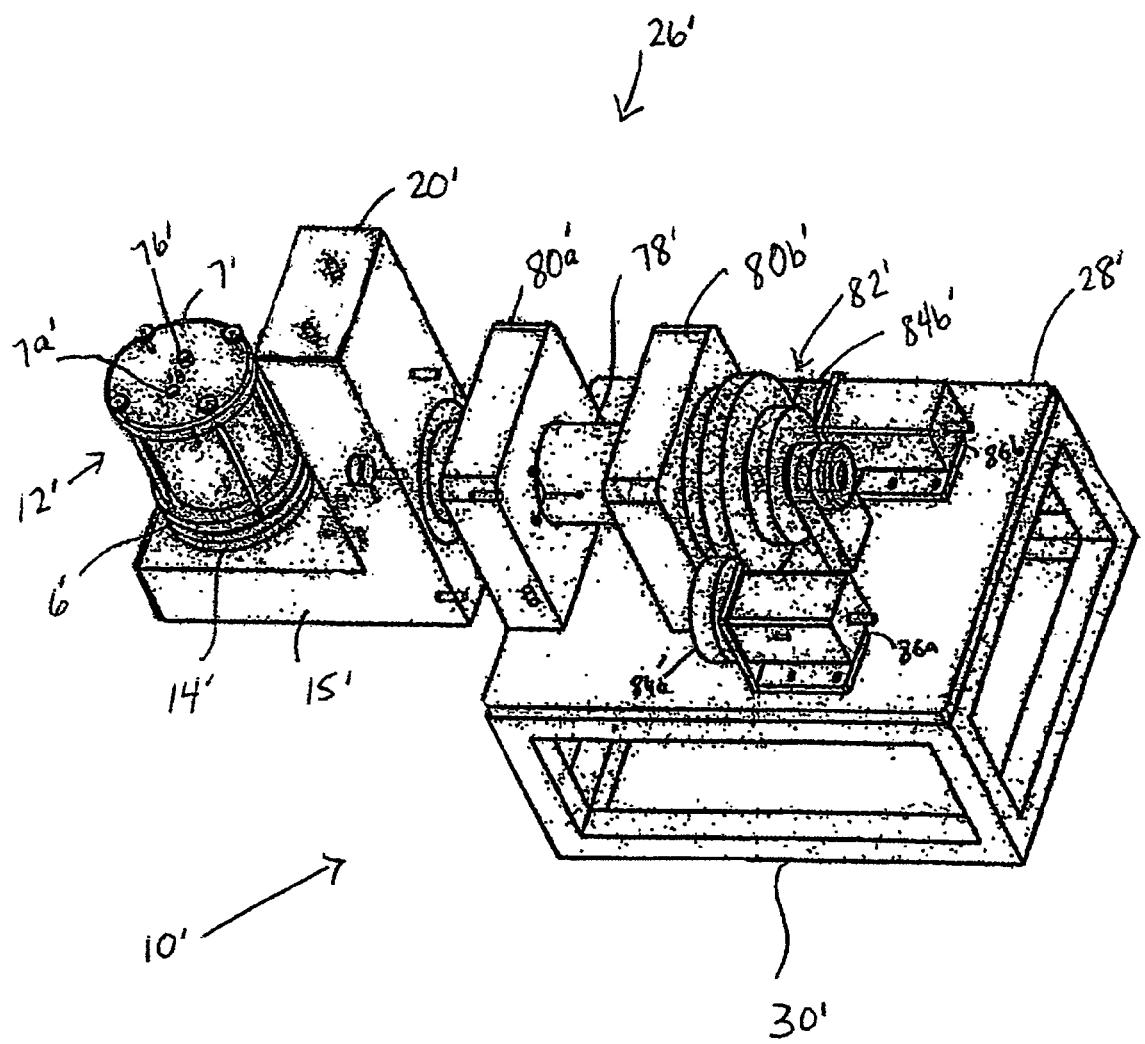
FIG. 15 shows a perspective view of the dual axial drive shafts of a second embodiment of the dual axis bioreactor, with the pipe connectors removed.

FIG. 15 a second preferred embodiment of a dual axis bioreactor 10'. The numbered features of the bioreactor 10' are the same as that of bioreactor 10 but are shown with the prime symbol (') for convenience and will not be described again here. The pipe connectors 32',34' are not shown in the figures for convenience. The drive mechanism 26' is different to the drive mechanism 26 of bioreactor 10, because servo-motor 86b' is not located in support arm 15 but is located on base plate 28'.

FIGS. 16-20 show the drive mechanism 26' of bioreactor 10' in greater detail. The drive mechanism 26' includes a main drive shaft 78', which extends through two mounting plates 80a',80b' attached to base plate 28'. The drive shaft 78' extends through the mounting plate 80a' and connects to the rotary L-shaped bracket 20' to rotate the arm in use. A gear train 82' is provided adjacent to mounting plate 80b' and is driven by rotors 84a',84b' that are respectively actuated in use by the servo motors 86a',86b' mounted on base plate 28'. The servo motors 86a',86b' are operated by a controller 112 (refer to FIG. 23), as will be described further below. The servo motor 86a' drives the drive shaft 78' and hence the rotary L-shaped bracket 20'. The servo motor 86b' drives an inner shaft 90' located within the drive shaft 78' as shown in FIG. 20, which shows an exploded perspective view of the drive shaft 78' and inner shaft 90', to drive the rotary plate 14'.

Referring now to FIGS. 15 to 20, the various components that make up the drive mechanism 26' will be explained in detail. It can be seen from FIG. 19 that the shaft 78' also includes an inner shaft 90', which is located inside the shaft 78' and is coupled to the rotary drive 13' of servo-motor 84b.

Figure 21:
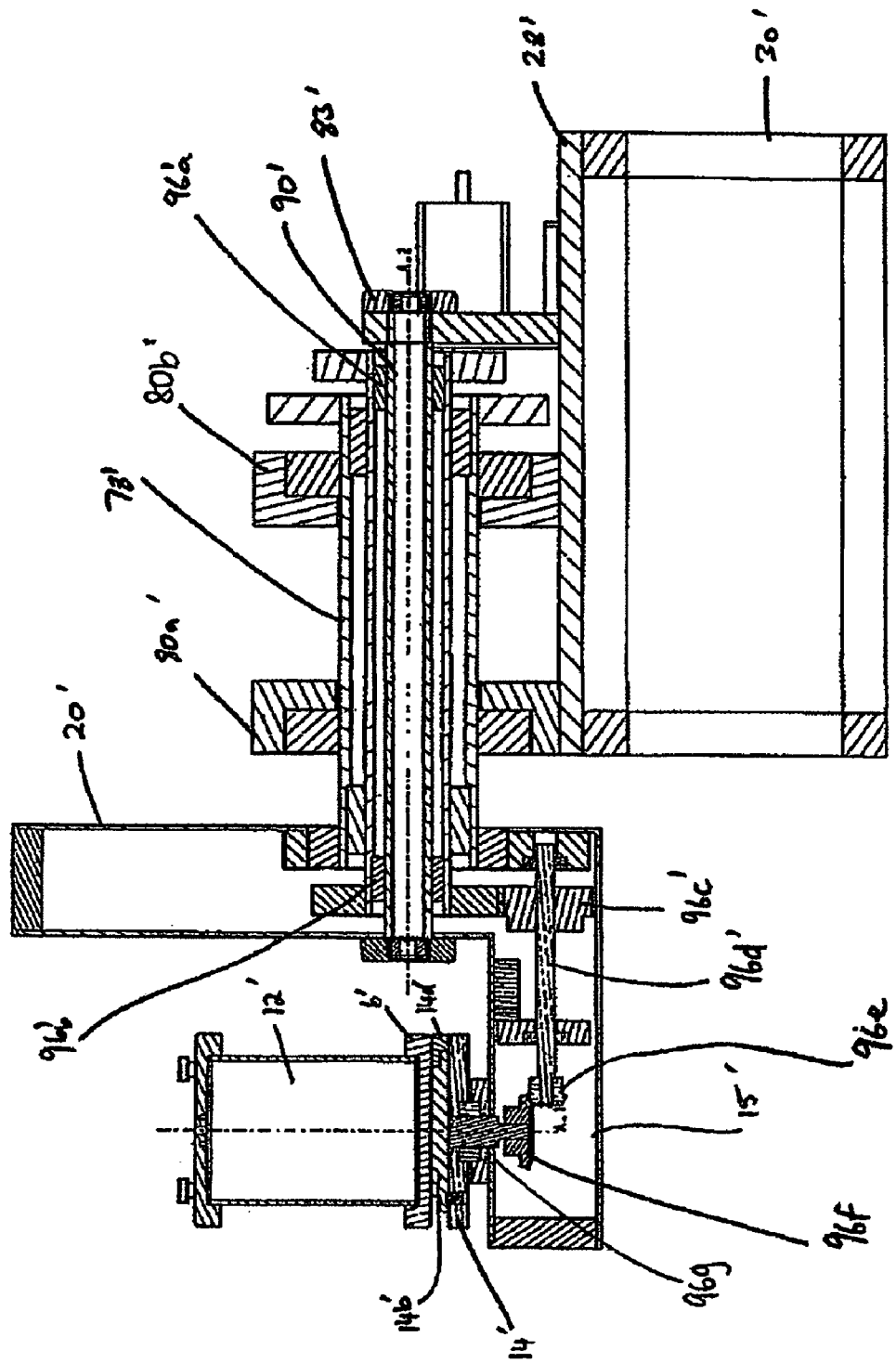
FIG. 21 shows a side cross-sectional view of the dual axial drive shaft of a second embodiment of the dual axis bioreactor of FIG. 15.
Figure 22:
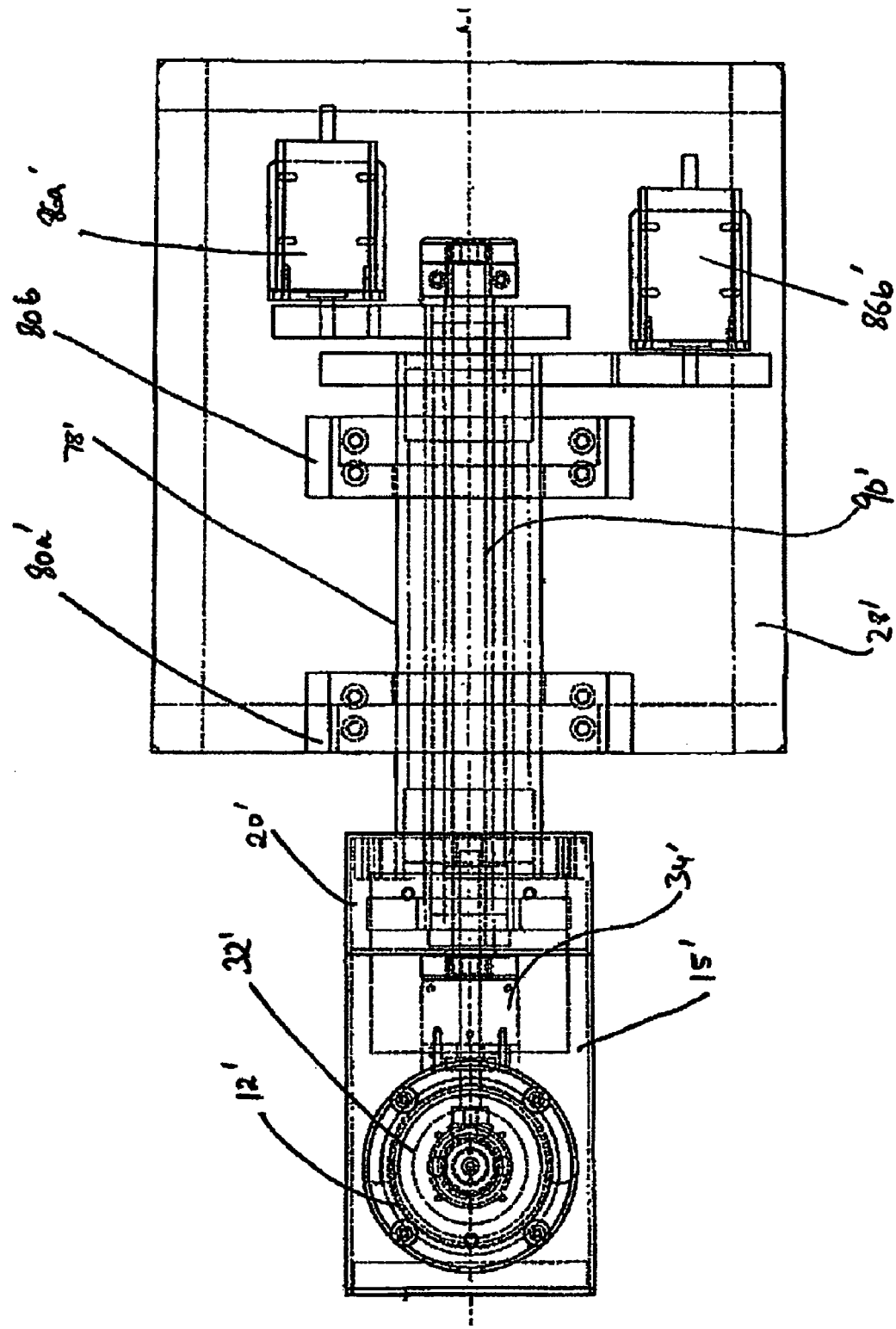
FIG. 22 shows a top view of the dual axial drive shaft of a second embodiment of the dual axis bioreactor of FIG. 15.

An end cap 93' is provided at the end of the shaft. The tubes 62c',72c' extend through the inner shaft and are connected to the connector 34 for transport of feed material to and product material from the chamber. Another end shaft cap 83' is provided adjacent to the gears and mounted to a tube collar 81'. A spur gear 88' is provided on the inner shaft 90' to allow rotary motion of the inner shaft 90' to be transferred to gear 96c' and through shaft 96d', bevel gears 96e,96f for driving rotary plate 14'. A bracket intershaft 79' is also provided to support the inner shaft 90'. A clamp lock 98' is provided on the drive shaft 78 to transmit the rotary motion of drive shaft 78' to the L-shaped bracket 20'. Bearings 96' are provided on the inner shaft 90' and the outer drive shaft 78' to carry loads imparted by the inner shaft 90' as it rotates in use. As shown in FIG. 21, inner shaft 90' has a spur gear 88' for rotating with a matching spur gear 96c' for rotating actuating rod 96d'. At the end of actuating rod 96d' is a bevel gear 96e' which actuates corresponding bevel gear 96f for turning shaft 96g and hence rotating plate 14'.

Figure 23:
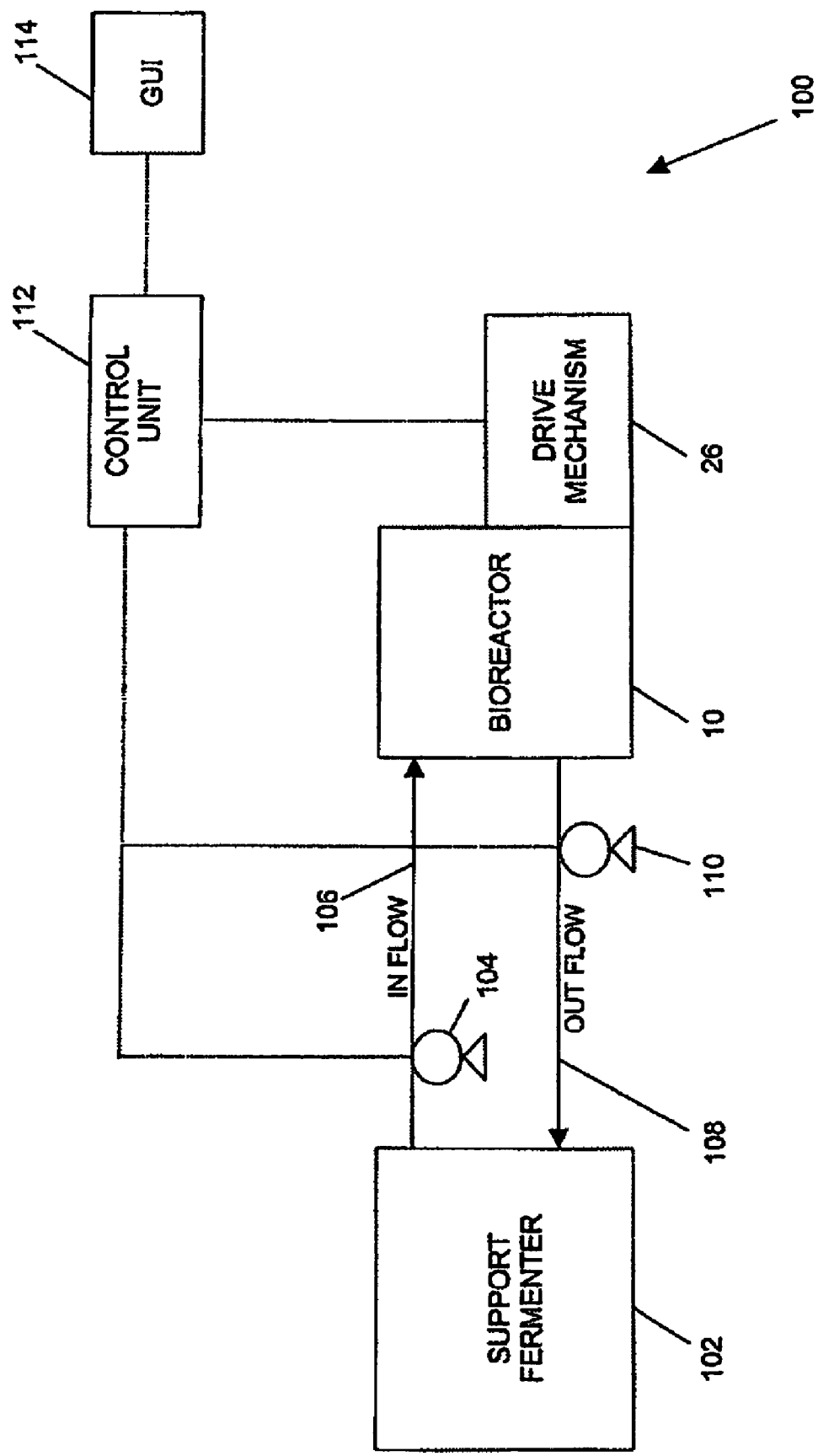
FIG. 23 shows a schematic diagram of a system for growing cell or tissue cultures in vitro using the bioreactor of FIG. 1.

Referring now to FIG. 23, there is shown a schematic diagram of a system 100 for growing three-dimensional cell or tissue cultures in vitro using the bioreactor 10 or 10'. For convenience, only bioreactor 10 will be described.

The system 100 includes a support fermenter 102 into which feed material is initially supplied. A pump 104 is provided on feed line 106, which transports feed material from the support fermenter 102 to one of the pipe connectors 32,34 or both. A pump 110 is provided on product line 108, which is coupled to one of the pipe connectors 32,34 or both. The product line 108 transports product media from the bioreactor 10 to the support fermenter 102.

A controller in the form of control unit 112 is electrically connected to the pumps 104, 110 and the drive mechanism 26 of the bioreactor 10. The controller includes a pump controller which is used to control the flow rate of feed material in feed line 106 and product material in product line 108. The control unit 112 is also electrically coupled to the servo motors 86a, 86b, which respectively drive the inner shaft 90 and drive shaft 78. The control unit 112 is also coupled to temperature sensor 7f, dissolved oxygen sensor 7g, pH sensor 7h and force detector 7m, to thereby allow for a number of process variables to be monitored during use.

In use, the support fermenter 102 is initially filled with a feed material for growing cell or tissue culture. The chamber 12 is placed on the rotary plate 14 and locked thereon by the knurled locking nut and bolt arrangement 4. The pipe connectors 32,34 are then attached to the inflow pipe 106 and the outflow pipe 108 by connecting to the inlet nipples 60 and outlet nipples 72 as described above. The chamber cover 7i is removed and the chamber 12 is seeded with cell or tissues and a three dimensional matrix or a scaffold is attached to the ends of needles 7j,7k.

Prior to use, the bioreactor 10, inflow line 106, product line 108 and pipe connectors 32,34 are first cleansed and sterilized. This may be achieved by a sterilizing solution that is coupled to a valve (not shown) on the inflow line 106 and circulated through an outlet valve (not shown) on the outflow line 108.

During use, the control unit 112 activates the pumps 104 and 110 so that feed media is supplied to the bioreactor 10 and product material is transferred from the bioreactor 10, thereby causing continuous circulation between the support fermenter 102 and the bioreactor 10. At the same time, the control unit 112 activates the servo-motors 86a and 86b to respectively rotate the drive shaft 78 and the inner shaft 90. This causes the chamber 12 to rotate about the vertical axis 16 in the direction of arrow 18 while simultaneously rotating the chamber about the horizontal axis 22 in the direction of arrow 24, as shown in FIG. 1.

As the control unit 112 is coupled to servo-motors 86a,86b, it is able to control the speed of rotation of the chamber about the horizontal axis 22 and the vertical axis 18. The direction of rotation may also be altered from that shown in FIG. 1.

Figure 25:
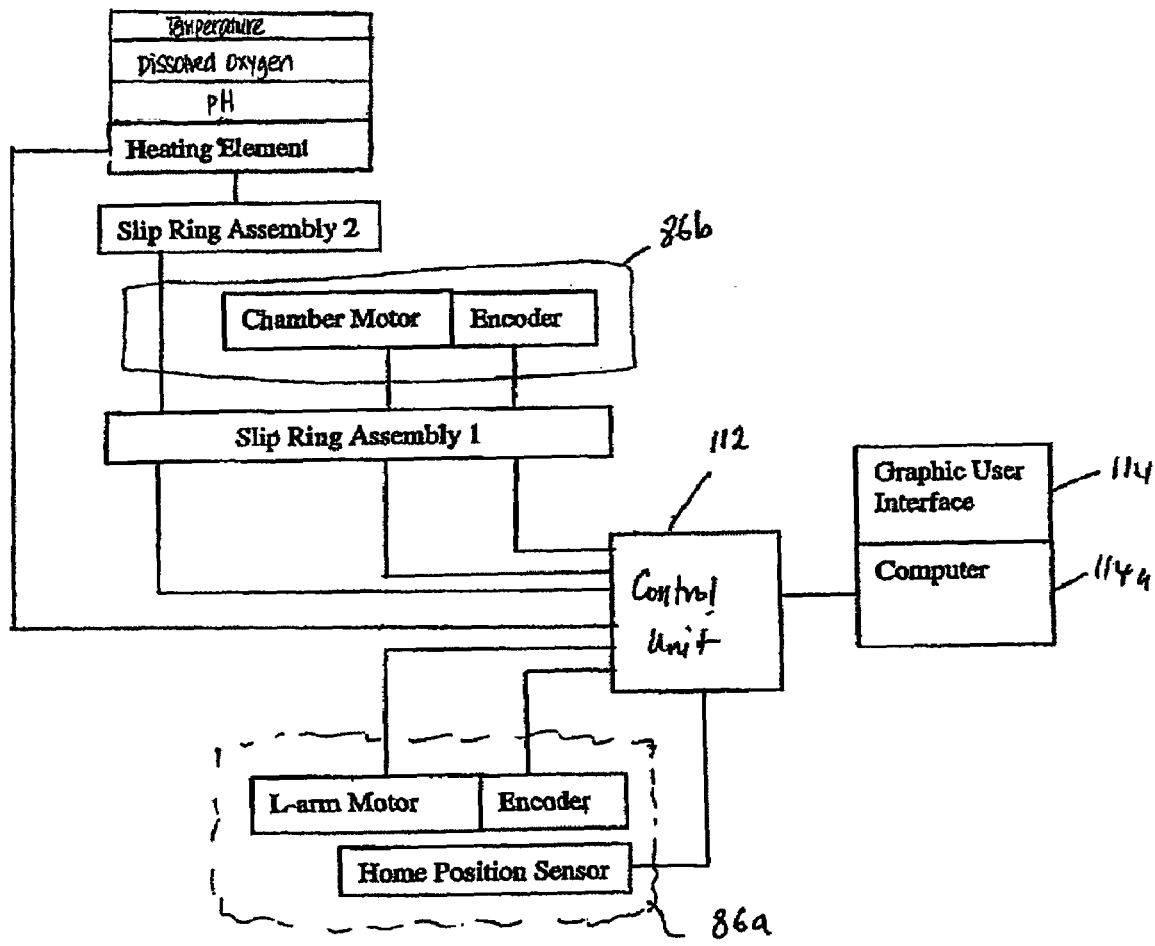
FIG. 25 shows a schematic of a control system for the system of FIG. 23.

A control system diagram for the system 100 is shown schematically in FIG. 25. As can be seen in this diagram, the control unit 112 is provided with two digital encoders for monitoring the speed and position of the servo-motors 86a and 86b. The control unit 112 is also connected to a Graphical User Interface (GUI) 114 connected to a PC 114a, to provide a user interface for a user to control the system 100. The slip ring assemblies allow data exchange and transmission between the servo motors 86a,86b and the control unit 112 as can be seen by the heater element, and the detectors for pH, temperature and dissolved oxygen. The control unit 112 is able to operate the bioreactor 10 in three modes: manual mode, jogging mode and profile mode.

The manual mode of operation allows the user to set the rotational speed and directions of both the vertical axis 16 and the horizontal axis 22 of rotation. The preset values can be changed during operation.

The jogging mode allows the user to oscillate the rotary L-shaped bracket 20 and the chamber 12 by setting speeds and the angles of oscillation. Accordingly, the servo motors (86a,86b) are capable of rotating the chamber 12 about an arc of rotation rather than continuously about both of the axes (16,22). In one embodiment, the arc of rotation is 45°, that is, the chamber 12 rotates about the axes (16,22) in one direction along an arc of 45° before rotating in an opposite direction back along the arc of 45°. The profile mode allows the user to set up to twenty settings of speed, time and direction for the operating variables of the bioreactor 10. A graphical profile of the execution of the settings can be shown graphically on the GUI 114. The bioreactor 10 can also be programmed in this mode to operate the settings in a continuous loop.

An advantage of the bioreactor of the present invention is that stable cell culture conditions can be achieved in the bioreactor system 100 throughout the course of cell culture growth. Experiments have been conducted to affirm this. The table below illustrates the average daily dissolved oxygen reading, pH reading and temperature reading in chamber 12 of bioreactor 10 for a period of 15 days when fluid material was re-circulated between reactor 10 and the support fermenter 102.

TABLE 1

Rotary L-arm bracket (20) speed: 3 to 30 rpm
Rotary plate (14) speed: 3 to 30 rpm

| Day | DO Reading | pH Reading | Temperature Reading (° C.) |
|---|---|---|---|
| 1 | 26.7 | 7.4 | 37 |
| 2 | 26.0 | 7.4 | 37 |
| 3 | 26.0 | 7.4 | 37 |
| 4 | 25.8 | 7.4 | 37 |
| 5 | 25.6 | 7.4 | 37 |
| 6 | 26.0 | 7.4 | 37 |
| 7 | 26.3 | 7.4 | 37 |
| 8 | 26.4 | 7.37 | 37 |
| 9 | 25.7 | 7.37 | 37 |
| 10 | 26.2 | 7.37 | 37 |
| 11 | 25.2 | 7.37 | 37 |
| 12 | 27.3 | 7.4 | 37 |
| 13 | 25.5 | 7.4 | 37 |
| 14 | 25.9 | 7.4 | 37 |
| 15 | 26.7 | 7.4 | 37 |

As can be seen from the above results, constant dissolved oxygen level, pH and temperature are maintained throughout the period of 15 days.

By providing very stable oxygen, pH and temperature conditions, it is possible to mimic the physiological conditions of cells and tissues.

As the L-shaped bracket 20 and the rotary plate 14 are coupled to respective servo-motors 86a,86b, the flow regimes within the bioreactor can be altered. This is achieved by being able to varying the speed of either the L-shaped bracket 20 or the rotary plate 14 so that the chamber 12 rotated at different speeds along either the horizontal axis 22 or vertical axis 16. If the speeds of rotation along either the horizontal axis 22 or vertical axes were fixed with respect to each other, the flow regimes within the chamber 12 would be fixed according to the single speed.

As flow regimes within the chamber 12 can be altered by independently varying the speeds of the L-shaped bracket 20 and the rotary plate 14, it is possible to dynamically optimize the conditions within the chamber 12 according to the type of cells or tissues being grown. Accordingly, the bioreactor 10 can be used for research applications for determining optimal operating parameters for the growth of particular cell or tissue cultures.

The ability to dynamically change the flow regimes within the chamber 12, ensures a homogenous body of nutrients are constantly being supplied to fibroblast cells as they grow on the scaffold. Furthermore, as two force vectors or flow vectors are applied to a growing cell or tissue culture at any point in time, spent nutrients from culture media is constantly being replaced at the sites of the growing cells or tissues with fresh nutrient culture media. This is a particular advantage in three-dimensional cell and tissue cultures as the fresh nutrient culture media is able to penetrate deep within the three-dimensional structure.

Figure 24:
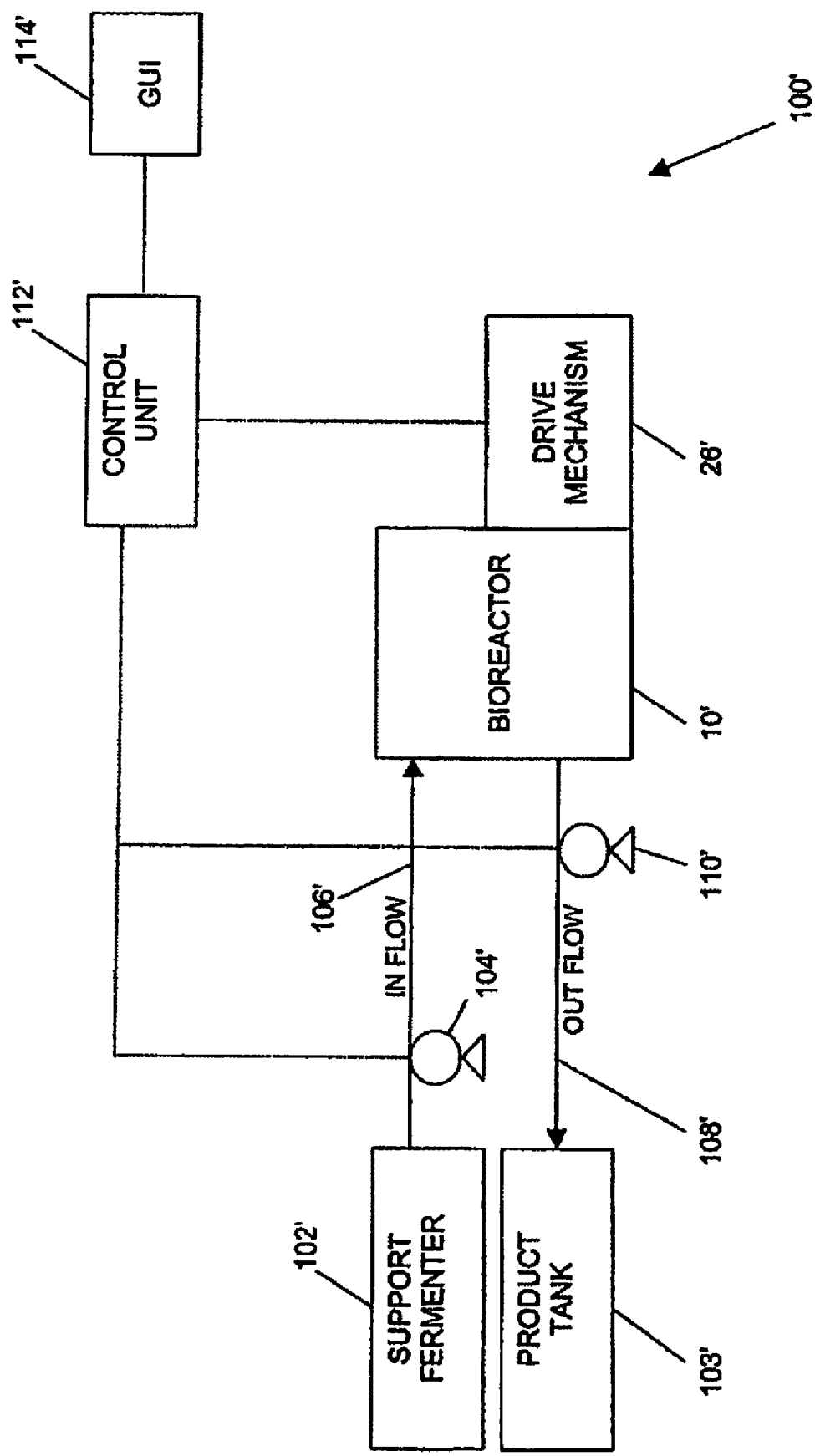
FIG. 24 shows a schematic diagram of an alternative system to the system of FIG. 23 for growing cell or tissue cultures in vitro using the bioreactor of FIG. 1

Referring now to FIG. 24, there is shown a schematic diagram of an alternative system 100' for growing three-dimensional cell or tissue cultures in vitro using the bioreactor 10'. The unit operations of the system 100' are the same as the unit operations of system 100 but are shown with the prime symbol ('). The difference in the system 100' is that the product material from the bioreactor 10' is not re-circulated back to a support fermenter 102' but is removed from the bioreactor 10 via product line 108' to product tank 103'.

Accordingly, system 100' shows a continuous flow bioreactor system for growing three-dimensional cell or tissue cultures in vitro.

Figure 26:
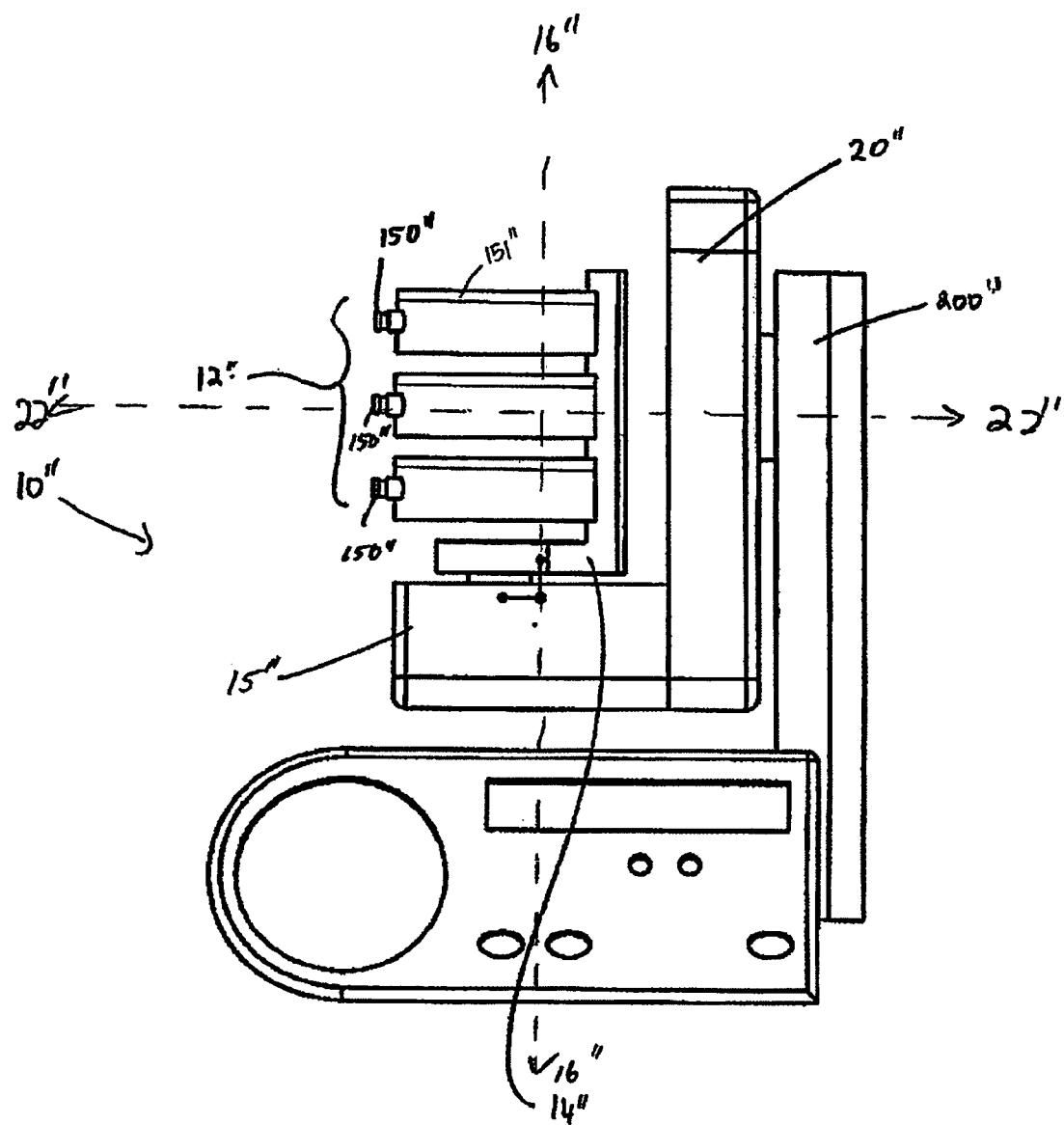
FIG. 26 shows a front view of an alternative dual axis bioreactor apparatus in accordance with another preferred embodiment.
Figure 27:
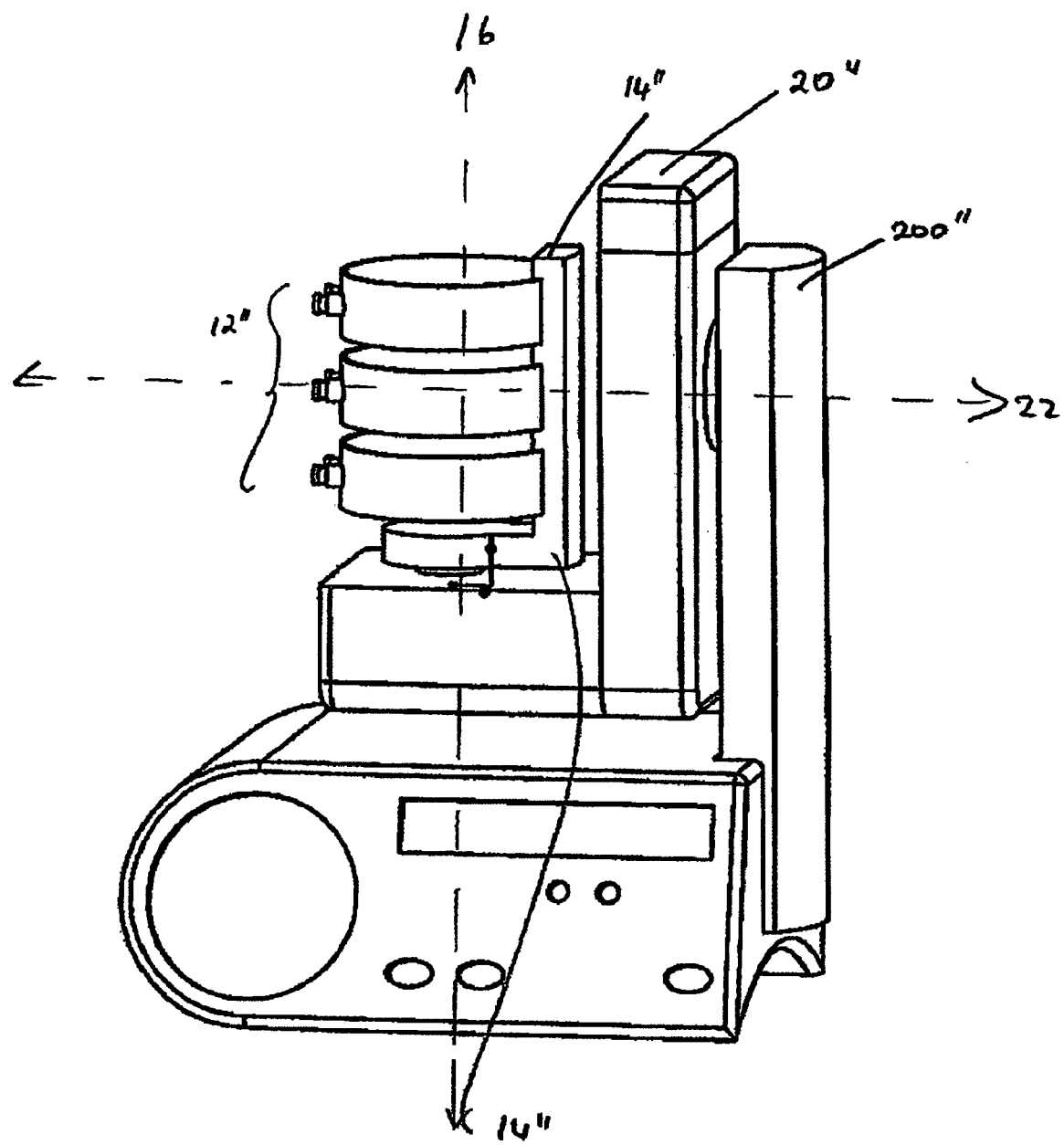
FIG. 27 shows a perspective view of the dual axis bioreactor apparatus of FIG. 26.
Figure 28:
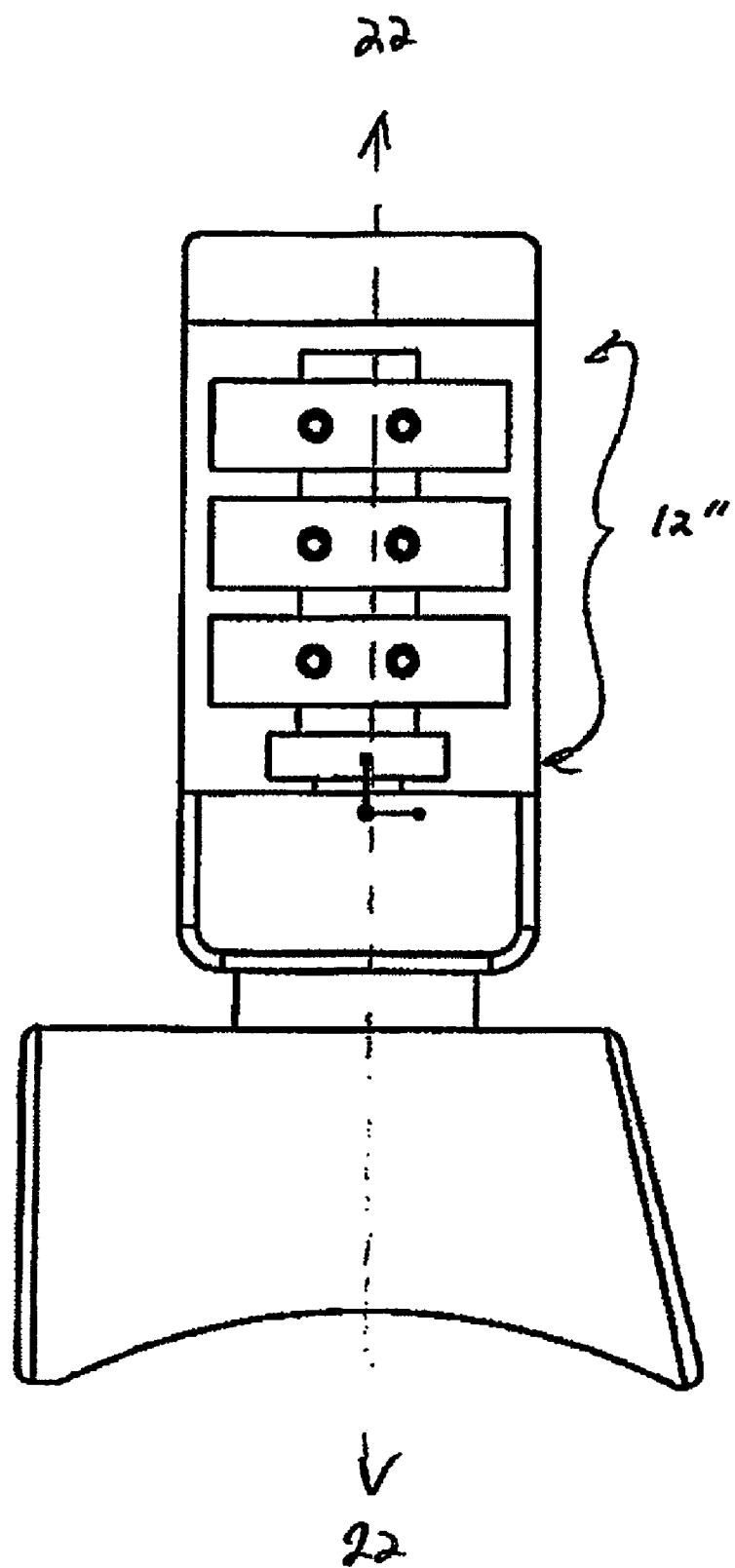
FIG. 28 shows a side view of the dual axis bioreactor apparatus of FIG. 26.

Referring now to FIGS. 26 to 28, there is shown a third alternative embodiment of a dual axis bioreactor 10" for growing cell or tissue cultures. The bioreactor 10" includes a cell or tissue culture modules 12" made of polycarbonate and constructed with a thin silicon membrane on one side for gas exchange within an incubator in which the bioreactor 10" is placed.

The cell or tissue culture modules 12" include a cap (151") which is removed for allowing a user to place nutrient medium into the modules 12" for growing cell or tissue cultures on a scaffold. In this embodiment, the scaffold is fixed to a mount in the form of two surgical needles (not shown) which are fixed to the inside of each module 12". The bioreactor 10" can be placed within a $CO_2$ incubator so that the thin silicon membrane on the side of the capsule allows ingress of $CO_2$ to thereby produce a $HCO_3^-/CO_2$ system, which acts as a buffer to maintain the pH of the culture media.

In this embodiment, the modules 12" are rotated about the vertical axis 16" by L-bracket 14" that is coupled to L-bracket 20" which rotates about horizontal axis 22". The L-bracket 20" is mounted on stationary frame 200". Two servo-motors (not shown) can rotate the L-brackets 14",20" about their respective axes and a drive mechanism and control system (not shown) similar to the drive mechanisms 26,26' and control unit 112 could be used to operate the bioreactor 10" as will be understood by persons skilled in the art.

It should be realized that the bioreactors 10,10', 10" of the present invention can be used to grow any type of cell or tissue and is advantageously can be used to grow three-dimensional cell or tissue culture for the formation of tissues including, but not limited to, skin; bone marrow; liver, pancreas, kidney, adrenal and neurological tissues.

The examples described herein illustrates the various uses of the bioreactor 10.

Embodiment 2

Dual Axis Bioreactor with Spherical Chamber

Figure 39:
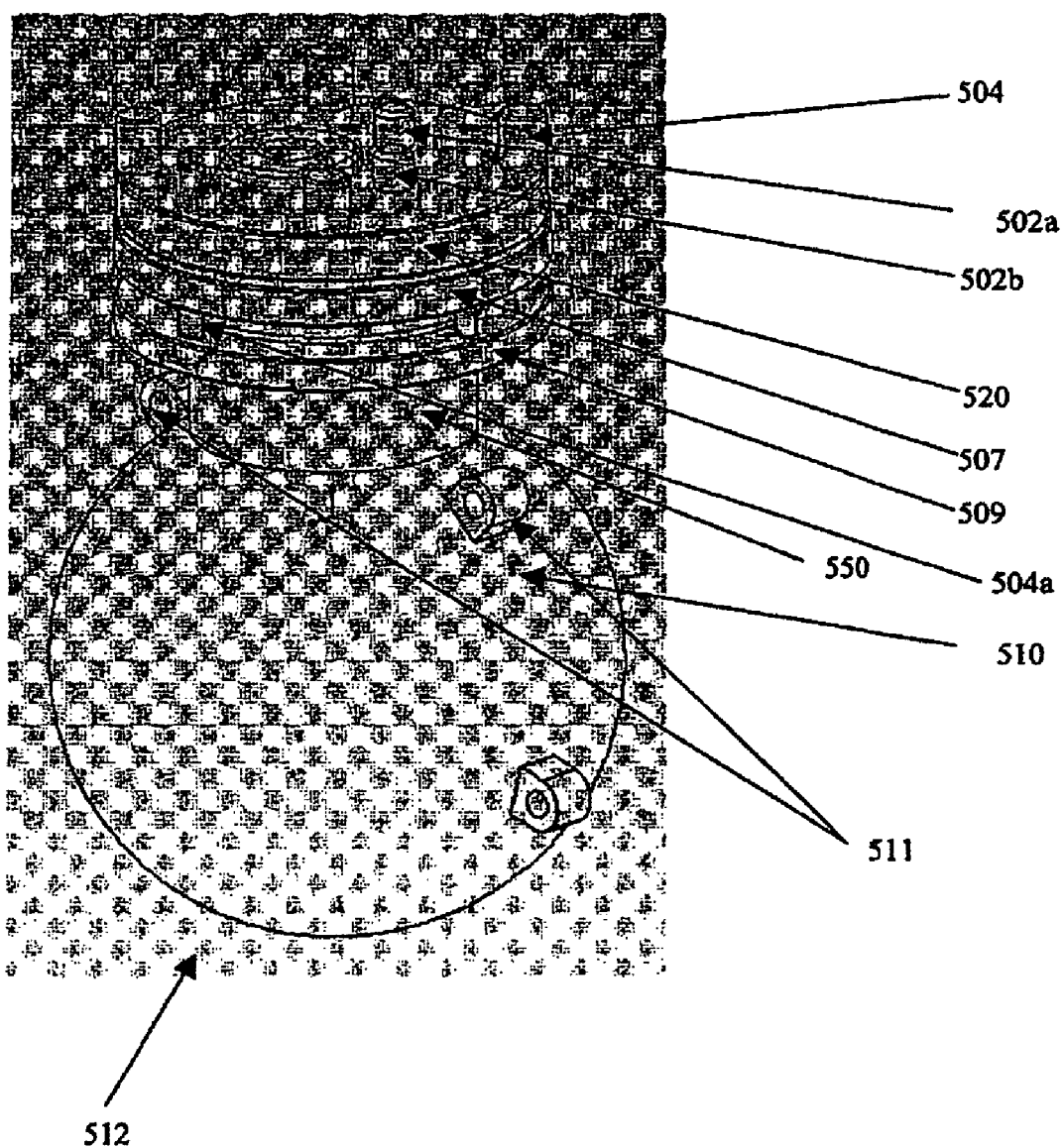
FIG. 39 shows a perspective view of an alternative embodiment of a spherical chamber used in the dual axis bioreactor shown in FIG. 1.

As an alternative to the cylindrical chamber 12, the dual axis bioreactor 10 of embodiment 1 can be replaced with a spherical-shaped chamber 512 shown in FIG. 39. The spherical chamber 512 comprises of a spherical cavity 510. The spherical cavity 510, in use, contains a cell or tissue culture medium, scaffold for cell or tissue culture and cell or tissue of interest. On the outer surface the spherical cavity 510, there are provided hooks (511a, 511b, 511c and 511d) for fixing the cylindrical chamber to the L-shaped bracket 20. The spherical chamber 512 is fixed to the rotary plate 14 by means of cylindrical rods (5a, 5b, 5c and 5d) which respectively extend from the rotary plate to the hooks (511a, 511b, 511c and 511d).

The spherical chamber 512 is also provided with a conduit 550 that extends from the cavity 510 up to a bottom chamber clamp plate 509. The bottom chamber clamp plate 509 is capable of being fixed to a top chamber clamp plate 507 with the help of fasteners 504a.

Figure 40:
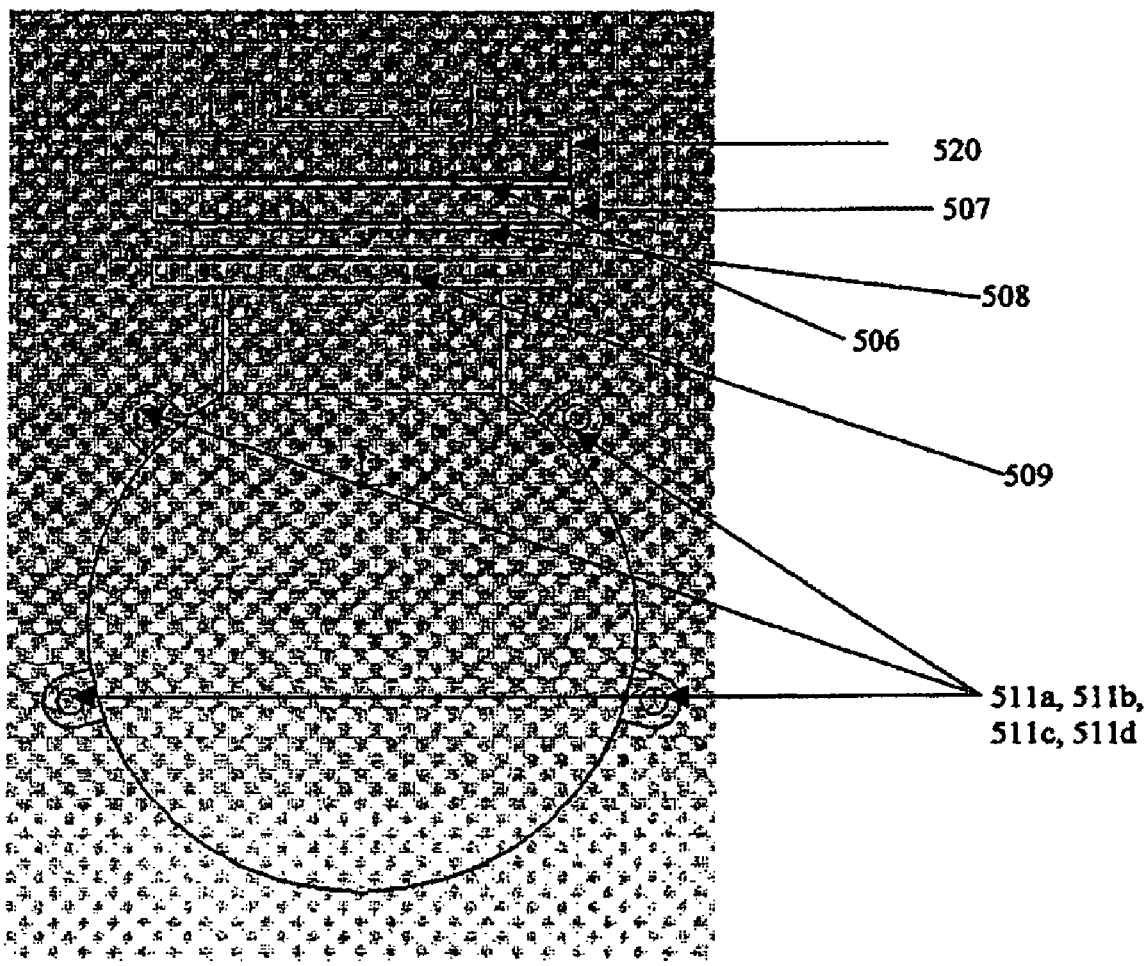
FIG. 40 is a front view of the spherical chamber of FIG. 39.

Referring to FIG. 40, a top chamber clamp plate seal 508 is located between the bottom chamber clamp plate 509 and the bottom chamber clamp plate 507. The top chamber clamp plate 507 and the bottom chamber clamp plate 509 are provided with a central orifice (not shown) capable of locating a T-plug 520 shown in FIGS. 41A and 41B. A T-plug seal 506 is located between the top chamber plate 507 and the T-plug 520. In use, the top clamp plate seal 508 and T-plug seal 506 ensures that no fluid can flow out of the spherical chamber 512 and an airtight environment is maintained.

Figure 41A:
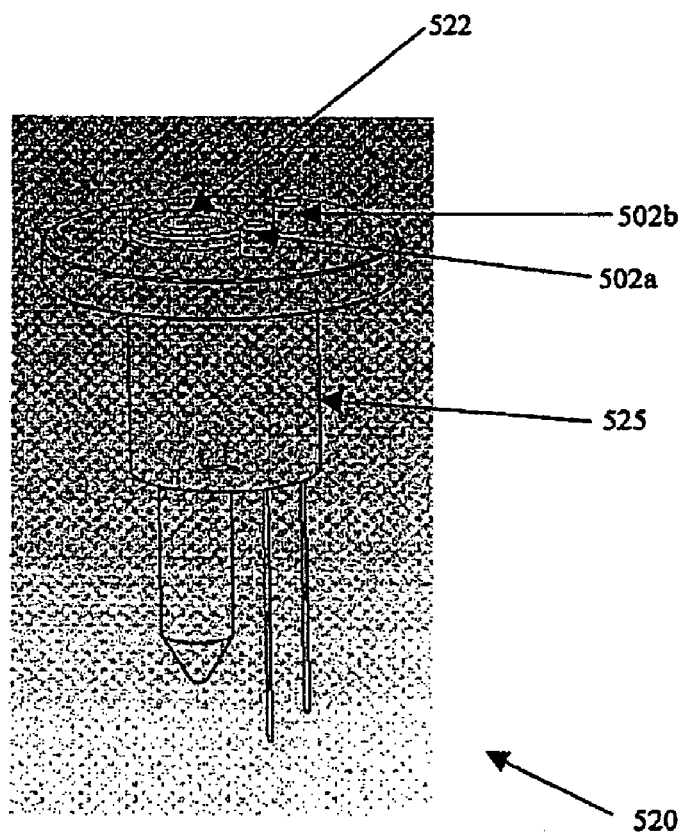
FIG. 41a shows a perspective side view of a T-plug used in the chamber of FIG. 39.
Figure 41B:
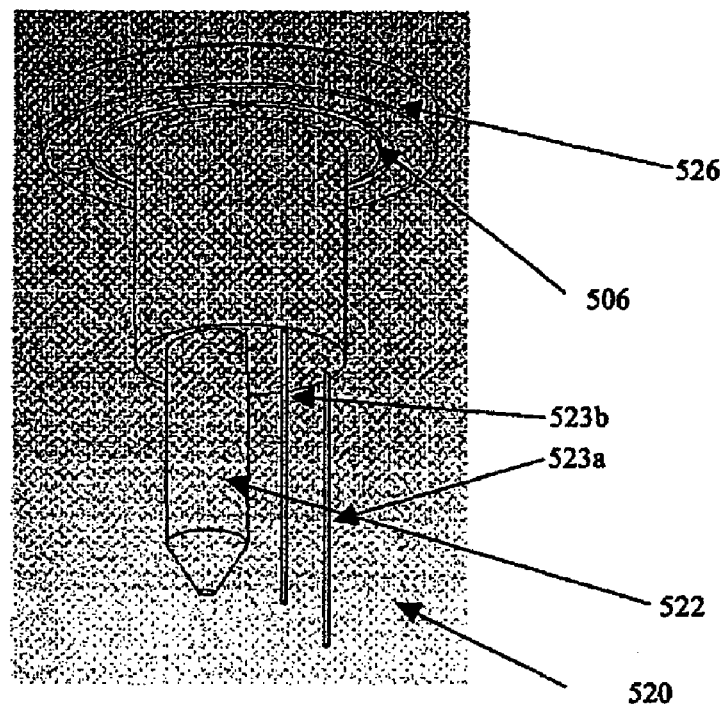
FIG. 41b shows a rear perspective view of the T-plug of FIG. 41A.

FIGS. 41a and 41b respectively show front and rear perspective views of the T-plug 520. The T-plug 520 is capable of being fixed to the top clamp plate 507 by means of a knurled locking bolt arrangement 504.

The T-plug 520 comprises a top plate 526 and a cylindrical body 525. In use, when the T-plug 520 is fixed to the top clamp plate 507, the cylindrical body 525 extends through the orifice of top clamp plate 507 and bottom clamp plate 509 into the spherical chamber 510. The top plate 526 is provided with slots for locating a gas exchange gland 522, an inlet conduit 502a and an outlet conduit 502b. On the bottom side of the top plate 526, there is provided a slot for locating the T-plug seal 506.

The inlet conduit 502a, the outlet conduits 502b and the gas exchange gland 522 extend from the top plate 526 into the chamber 510 through the cylindrical body 525. The inlet and outlet conduits (502a & 502b) extend into the chamber 510 in the form of surgical needles 523a and 523b. In use, the inlet conduits 502a is connected to the tube 7d to feed fluid materials to the chamber 510 and the outlet conduit 502b is connected to the tube 7e to withdraw the fluid material from the chamber 510. In use, the gas exchange gland 522 enables the flow of gas, such as oxygen, carbon dioxide and air, to and from the chamber 510.

In this embodiment, the cylindrical chamber 512 is made up of glass. The top and bottom chamber plates (507,509) are made up of stainless steel. The gas exchange gland 522 is made up of semi permeable silicon tube that is permeable to gases but impermeable to liquids and the surgical needles (523a, 523b, 530) are made up of stainless steel.

Embodiment 3

Omni-Directional Rotary Bioreactor

Figure 35:
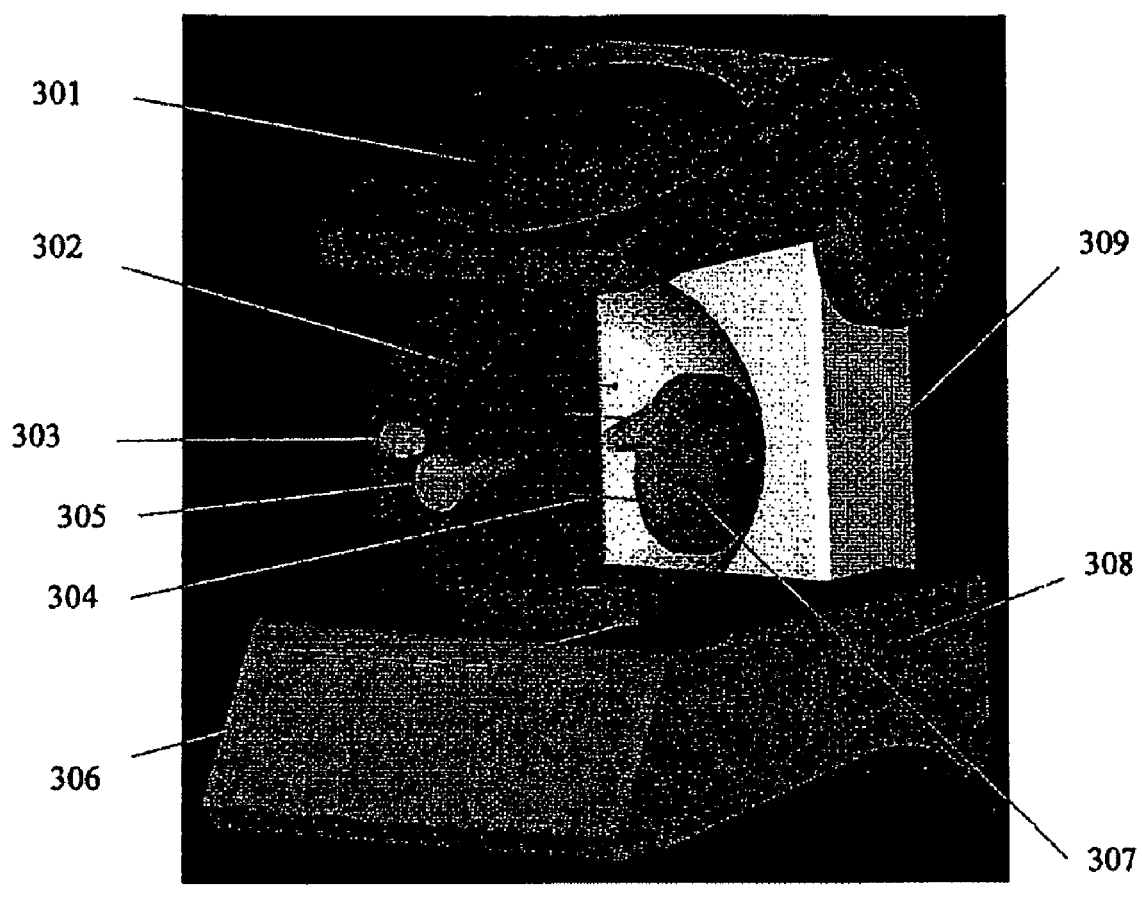
FIG. 35 shows a perspective view of second embodiment of a bioreactor capable of rotating along three axes (here called "omni-directional rotary bioreactor").
Figure 36A:
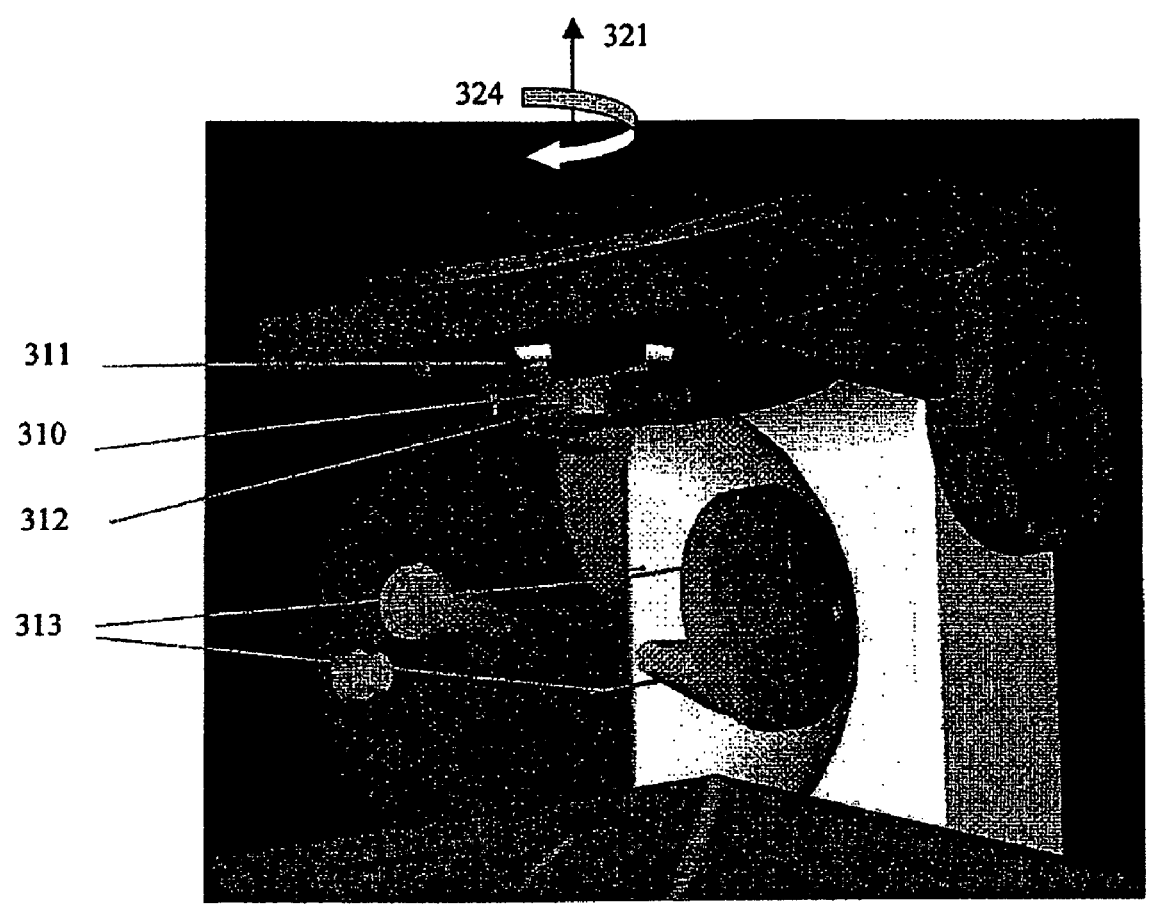
FIG. 36a shows a perspective view of the omni-directional drive for rotation about the third axis.
Figure 36B:
FIG. 36b shows a perspective view of the omni-directional drives for rotation about the first-axis and second-axis.

Referring now to FIG. 35 there is shown a perspective view of another embodiment of a bioreactor for growing cells and tissue cultures, here called an "omni-directional rotary bioreactor 318". The bioreactor 318 includes a chamber 302 for containing a cell or tissue culture and a culture medium for growing cell or tissue cultures in use. The bioreactor 318 also includes a rotary wheel in the form of wheel 314 (shown in FIG. 36b) for rotating the chamber 302 at a first speed about a first axis 319. The bioreactor 318 also includes a second rotary wheel in the form of wheel 315 for rotating the chamber at a second speed about a second axis 320. The bioreactor 318 also includes a third rotary wheel in the form of wheel 311 at a third speed about a third axis 321. The axes 319, 320 normal relative to each other and both axes are normal relative to the third axis 321. As will be described further below, in use, the magnitude of the first speed, second speed and third speed are independently variable of each other to thereby grow a cell or tissue culture within the chamber.

Referring to FIGS. 35, 36a, 36b, 37, the chamber 302 may be provided with a three-dimensional matrix (not shown) when growing three-dimensional cell or tissue cultures as will be described further below. The chamber 302 includes a spherical chamber having one inlet port 310, two outlet ports 312, 317 and one sampling port 303 for insertion and retrieval of fluid or product material within the chamber 302 that is used to grow the cell tissue cultures.

In this embodiment, the chamber 302 is provided with a chamber cover 307 for introducing a three dimensional matrix or a scaffold into the chamber 302. The chamber cover 307 includes a mount for retaining a scaffold in the form of a pair of surgical needles 313, which are used to impale a three-dimensional matrix onto in use. The three-dimensional matrix can be any kind of porous scaffold and is used to provide an attachment structure for the growth of three-dimensional cell cultures and tissues thereon in use.

Referring now again to FIGS. 36a and 36b, the wheels (311, 314, 315) are driven in use by respective servo-motors (not shown).

It should be realized that the wheels (311, 314, 315) may rotate about the respective first, second and third axes (319, 320, 321) in an opposite direction to the direction of respective arrows (322, 323, 324).

It should be appreciated that the third axis 321 may not be at a right angle relative to the axes 319 and 320 but may extend anywhere within an arc covering the range of 60° to 120° relative to the third axis. It should also be appreciated however, that the second axis 320 may not be at a right angle relative to the axes 319 and 321 but may extend anywhere within an arc covering the range of 60° to 120° relative to the second axis.

The wheels (311,314,315) can be driven simultaneously to enable the culture chamber to rotate about all three principal axes of rotations, i.e. about axes (319,320,321) with the desired rotary motion determined by the resultant directional vector of all three wheels (311,314,315). This movement subjects a growing cell or tissue culture within the chamber 302 to a flow regime that is determined by the directional vector in order to propagate a three-dimensional cell or tissue culture.

In the use, it should be realized that periodic or sequential rotation of the chamber via the wheels (311,314,315) may occur simultaneously when growing cell or tissue cultures.

The servo motors driving the wheels (311,314,315) are operated by a controller 412', as will be described further below. The servo motors are also provided with encoders to monitor the position of the rotors and the encoders send data to the control unit 412' for control over the bioreactor 318.

The wheels (311,314,315) may rotate the culture chamber 302 between the ranges of 1 to 50 rpm.

Figure 38:
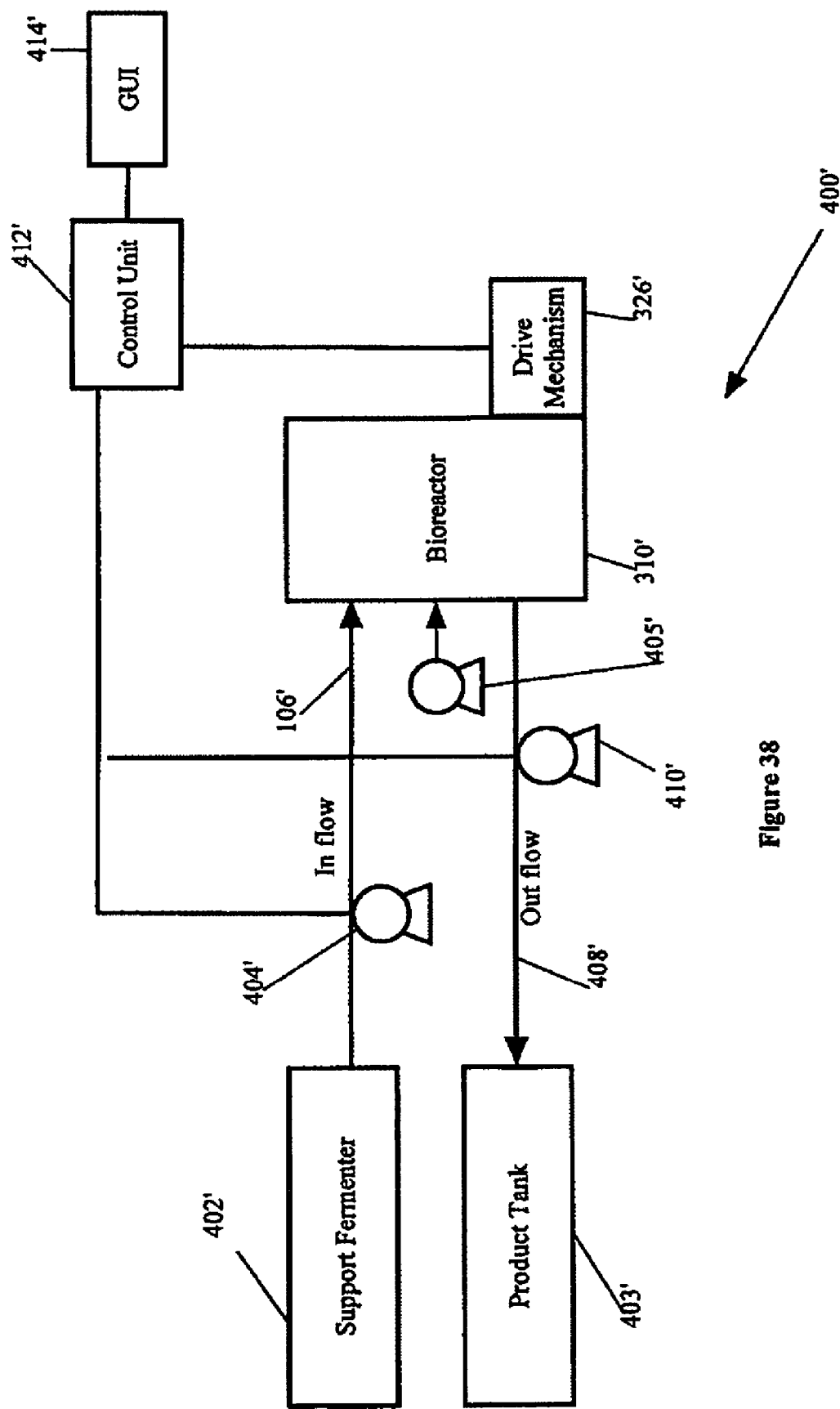
FIG. 38 shows a schematic diagram of a system for growing cell or tissue cultures in vitro using the omni-directional rotary bioreactor of FIG. 35.

Referring now to FIG. 38, there is shown a schematic diagram of a system 400' for growing three-dimensional cell or tissue cultures in vitro using the bioreactor 318.

The system 400' includes a feed material tank 402' into which feed material is initially supplied. A pump 404' is provided on feed line 406', which transports feed material from the feed material tank 402' to a fluidly sealed passage in the fluid connector 310. A pump 410' is provided on product line 408', to transport product media from the bioreactor 318, outlet port 312 or 317, to the product tank 403'.

A controller 412' is electrically connected to the pumps 404', 410' and the drive mechanism 326' of the bioreactor 318. The controller 412' includes a pump controller which is used to control the flow rate of feed material in feed line 406' and product material in product line 408'. The control unit 412' is also electrically coupled to the servo motors which respectively drive the wheels (311,314,315). The controller 412' is also coupled to a position sensor to bring the chamber to a 'home' position for loading or retrieval of the three-dimensional matrix.

The system 400' also includes a compressor 405' that is in fluid communication with the chamber 302 of the bioreactor 318. The compressor 405' is used to increase the fluid pressure within the chamber 302 while the cells or tissue cultures are growing.

In use, the feed material tank 402' is initially filled with a feed material for growing cell or tissue culture. The chamber 302 is placed on rollers located in the chamber base plate 325 and locked in place by lowering the omni-drive housing 301.

Prior to use, the bioreactor 318, inflow line 406', product line 408' are first cleansed and sterilized. This may be achieved by a sterilizing solution that is coupled to a valve (not shown) on the inflow line 406' and circulated through an outlet valve (not shown) on the outflow line 408'.

During use, the controller 412' activates the pump 404' so that feed media is supplied to the bioreactor 318. After filling the chamber with feed media, the control unit 412' activates the servo-motors to rotate the chamber 302 in the preferred direction of rotation.

As the controller 412' is coupled to the servo-motors it is able to control the rotational speed of the chamber 302 and the direction of rotation by setting the speeds of omni-wheel drives 311, 314 and 315.

A control system diagram for the system 400' is shown schematically in FIG. 38. The controller 412' is provided with three digital encoders for monitoring the speed and position of the servo-motors. The control unit 412' is also connected to a Graphical User Interface (GUI) 414' to provide a user interface for a user to control the system 400'. The controller 412' is able to operate the bioreactor 318 in three modes: manual mode, jog mode and profile mode.

The manual mode of operation allows the user to set the rotational speeds and directions of all three omni-wheel drives. The preset values can be changed during operation.

The jog mode allows the user to oscillate the chamber by setting the speeds and the angles of oscillation.

The profile mode allows the user to set up to twenty settings of speed, time and direction for the operating variables of the bioreactor 318. A graphical profile of the execution of the settings can be shown graphically on the GUI 414'. The bioreactor 318 can also be programmed in this mode to operate the settings in a continuous loop.

By providing a chamber that allows gas exchanges to take place through the silicon membrane 305 and operating within a stable $CO_2$ or $O_2$ environment and temperature conditions inside an incubator, it is possible to mimic the physiological conditions that encourages cells and tissues growth.

The flow regimes within the bioreactor can be altered by being able to vary the speeds and directions of rotation of the chamber via the wheels (311,314,315).

As flow regimes within the chamber 302 can be altered independently varying the speeds and directions of the wheels (311,314,315), it is possible to dynamically optimize the conditions within the chamber 302 according to the type of cells or tissues being grown. Accordingly, the bioreactor 318 can be used for research applications for determining optimal operating parameters for the growth of particular cell or tissue cultures.

The ability to dynamically change the flow regimes within the chamber 302 ensures a homogenous body of nutrients are constantly being supplied to fibroblast cells as they grow on the scaffold. Furthermore, as three flow vectors are applied to a growing cell or tissue culture at any point in time, spent nutrients from culture media is constantly being replaced at the sites of the growing cells or tissues with fresh nutrient culture media. This is a particular advantage in three-dimensional cell and tissue cultures as the fresh nutrient culture media is able to penetrate deep within the three-dimensional structure.

It should be realized that the bioreactors 318 of the present invention can be used to grow any type of cell or tissue and is advantageously can be used to grow three-dimensional cell or tissue culture for the formation of tissues including, but not limited to, skin; bone marrow; liver, pancreas, kidney, adrenal and neurological tissues.

EXAMPLE

The following examples illustrate the various uses of the bioreactors.

Example 1.1

Three-Dimensional Skin Culture Preparation

Figure 29:
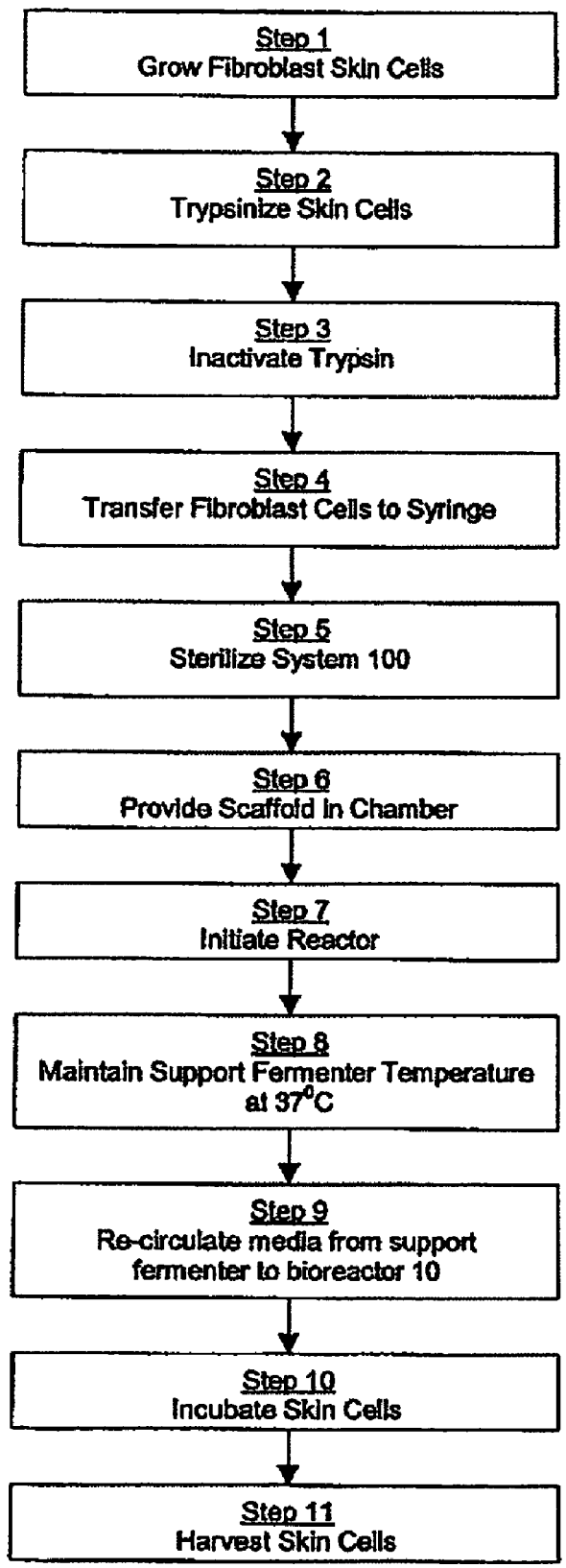
FIG. 29 schematically shows the steps of a method that is used to grow a three-dimensional skin culture in vitro using the system of FIG. 23.

FIG. 29 schematically shows the steps of a method that was used to grow a three-dimensional skin culture in vitro using the system 100 as follows:

Step 1: Human fibroblast skin cells were grown to confluency in a 150 $cm^{-2}$ Falcon tissue culture flask containing 20 ml. of a culture medium consisting of Dulbecco's modified Minimum Essential Medium (MEM) containing 10% fetal calf serum. Dulbecco's modified Minimum Essential Medium is a standard commercially available culture medium obtained from Microbiological Associates, Bethesda, Md., United States of America.

Step 2: The spent culture medium was removed from the flask and the fibroblast cell growth was trypsinized with 2 ml of 0.25% trypsin in phosphate buffered saline for three minutes.

Step 3: The trypsin was inactivated by dilution with a 20 ml portion of the same culture medium.

Step 4: The fibroblast cells were then transferred to a sterile syringe.

Step 5: The chamber 12 of the bioreactor 10, the feed line 106, the product line 108, the pipe connectors 32,34 and the support fermenter were gas sterilized with ethylene oxide, washed with sterile water to remove ethylene oxide residue and then equilibrated by priming with Dulbecco's modified Minimum Essential Medium (MEM) containing 2% fetal calf serum.

Step 6: A nylon polyester fiber scaffold cylinder having a diameter of 80 mm and a height of 180 mm was provided in the chamber 12. The chamber 12 was inoculated with 30 ml of the fibroblast cell suspension in the syringe of step 4 to begin incubation of the fibroblast cells.

Step 7: Using the control unit 112, bioreactor 12 was activated to rotate the chamber 12 about the vertical axis 16 in the direction of arrow 18 at 20 rpm and the horizontal axis 22 in the direction of arrow 24 at 20 rpm.

Step 8: The media within the support fermenter was maintained at a temperature of 37° C. by a water bath surrounding support fermenter.

Step 9: After the first hour of incubation, pumps 104 and 110 re-circulated the media of the chamber 12 from the support fermenter 102 to the chamber 12 to maintain the temperature of the media during incubation.

Step 10: The chamber 12 was allowed to incubate to grow skin cells for 3 days.

Step 11: At the termination of incubation, the skin cells were harvested by removing the scaffold from the chamber 12 and thoroughly washing the chamber 12 in saline.

The scaffold contained three-dimensional skin tissue. The skin fibroblasts had stretched across the mesh openings. The skin cells had cell-cell and cell-matrix interactions that were characteristic of whole tissue in vivo cells. The three-dimensional skin tissue can be cut and used in a variety of applications.

Preparation of Media and Reagents

The following reagents in examples 2 to 6 were prepared as follows:

Preparation of DMEM+F12 Media, Required Volume: 1000 ml
1. Measure out 80% of the required volume or 800 ml of ultrapure water.
2. Add DMEM+F12 media powder to the ultrapure water and stir gently.
3. Add 16.0 ml of 7.5% w/v sodium bicarbonate solution.
4. Adjust pH of the media to 0.1-0.3 units below the desired pH of 6.8.
5. Top up with ultrapure water to the required volume of 1000 ml.
6. Sterilize immediately by membrane filtration using a membrane with porosity of 0.22 μm.
7. Aseptically disperse the media into a sterilized bottle.
8. Aliquot out a small volume into a centrifuge tube and incubate it for a sterility check.
9. Store the remaining media in a fridge at 4° C.
10. Complete the media by adding 10% FCS w/v and 1% Pen/Strep/Amp w/v, after it has pass the sterility check.

Preparation of Collagenase II
1. Dissolve completely 0.1 g of collagenase II powder into 50 ml of serum-free media.
2. Filter the solution through a 0.22 μm filter disc.
3. Disperse the solution into centrifuge tubes and store them at 4° C.

Preparation of Sodium Alginate
1. Dissolve completely 1.5 g of sodium alginate into 100 ml of PBS solution.
2. Autoclave the solution or filter it with 1.8 μm filter disc for at least 3 times.

Preparation of PBS Solution [10× Stock]
1. Dissolve the following components in 1000 ml of ultrapure water:

| | |
|---|---|
| NaCl | 80 g |
| KCl | 2 g |
| $KH_2PO_4$ | 2 g |
| $Na_2HPO_4 \cdot 2H_2O$ | 14.1 g |

2. Sterilization of PBS is done by autoclaving a 1×PBS stock.

Example 1.2

Isolation of Chondrocytes/Cartilage from Pig's Ears

Step 1: Surface sterilization was conducted on the pig's ears in a bio-safety cabinet. Three beakers were filled with iodine, alcohol and PBS respectively. The pig's ears are then soaked in each beaker for 15 minutes.

Step 2: The ears were placed on a sterile plate and the skin and other muscle tissues removed leaving behind only the cartilage.

Step 3: The cartilage was transferred onto a new sterile plate and cut into thin slices. This facilitates digestion at a later stage. A small amount of PBS was added to keep the cartilage wet. The thin slices of cartilage were then aseptically transferred into 50 ml centrifuge tubes.

Step 4: Collagenase II was added into the centrifuge tubes to form a cell suspension. The tubes were placed into a shaking incubator for 16-18 hrs at 37° C. to ensure homogenous digestion. Digested cartilage is indicated by a change in color of the collagenase II from red to yellow with turbidity.

Step 5: A little of the digested cartilage was removed and tested for contamination using an inverted microscope.

Step 6: The cell suspension is then filtered through a sterile nylon filter to remove any undigested cartilage.

Step 7: 20 ml of PBS was added to the filtered cell suspension, and the resulting mixture centrifuged at 2500 rpm for 5 min.

Step 8: The supernatant resulting from the centrifuge was carefully poured away and the residual cartilage (also known as chondrocytes) was washed with PBS to remove the collagenase II.

Step 9: The centrifuge tubes containing the washed cartilage was inverted and centrifuged at 2500 rpm for 3 minutes. Thereafter, the PBS was removed from the centrifuge tubes.

Step 10: 10 ml DMEM media was added to the cartilage, followed by a transfer into a T-25 flask to check for contamination under a microscope.

Step 11: The isolated cartilage tissue was then placed in the bioreactor 10. Conditions therein are at a temperature of 37° C. and 5% volume $CO_2$.

A three-dimensional cartilage tissue was obtained in which cartilage tissue had cell-cell and cell-matrix interactions that were characteristic of in vivo cartilage tissue.

Example 1.3

Thawing and Maintenance of Cells

Step 1: A cryovial of Goat Chondrocyte cells was removed from liquid nitrogen and placed them immediately into a water bath set at 37° C. for less than 1 minute until the last trace of ice vanishes.

Step 2: The cryovial was then removed from the water bath and sprayed with 70% ethanol before placing it in the bio-safety cabinet.

Step 3: The cryovial was then transferred into a centrifuge tube containing 9 ml sterile DMEM media and spun at 1500 rpm for 6 minutes.

Step 4: After centrifugation, the supernatant was removed and the residual cryovial was re-suspended in 2 ml sterile DMEM media. About 15 μl of the suspension is then removed for analysis on the number of viable cells count.

Step 5: More than $1 \times 10^5$ cells/ml were then seeded into a T-75 flask with 20 ml sterile DMEM media, and the cells were incubated in the bioreactor 10 at 37° C., 5% $CO_2$.

Step 6: Cell growth was examined daily and replenished with fresh DMEM every 3 days.

Figure 30:
FIG. 30 shows an SEM micrograph of goat chondrocytes seeded onto a 3D ear shaped scaffold, which was incubated in a static environment in accordance with the prior art.
Figure 31:
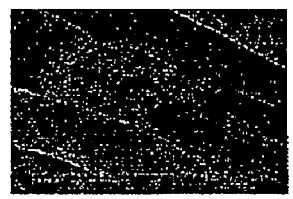
FIG. 31 shows an SEM micrograph of goat chondrocytes seeded onto a 3D ear shaped scaffold, which was incubated in a bioreactor that rotated about a single axis of rotation in accordance with the prior art.
Figure 32:
FIG. 32 shows an SEM micrograph of goat chondrocytes seeded onto a 3D ear shaped scaffold, which was incubated in the bioreactor of FIG. 1 in accordance with the present invention.

FIGS. 30 to 32 shows a SEM micrograph of goat chondrocytes seeded onto a 3D ear shaped scaffold. The cultured chondrocytes of FIG. 30 were incubated in a static environment, the cultured chondrocytes of FIG. 31 were incubated in a bioreactor that was subjected to a single a single axis of rotation and the cultured chondrocytes of FIG. 32 were incubated in the bioreactor 10 which subjected the cells to axes of rotation.

From FIG. 32, it can be seen that the scaffold cultured in the bioreactor 10 of the present invention, contained three-dimensional skin tissue in which the skin fibroblasts had stretched across the mesh openings of the scaffold. The skin cells had cell-cell and cell-scaffold interactions that were characteristic of whole cartilage tissue in vivo cells.

In comparison with FIG. 30, the ear shaped scaffold cultured in the static environment has hardly any skin tissues forming therein.

Further in comparison with FIG. 31, the ear shaped scaffold cultured in a single axis rotating reactor, although has more skin tissue forming as compared to that in FIG. 30, is still not as fully developed as that in FIG. 32.

Figure 33:
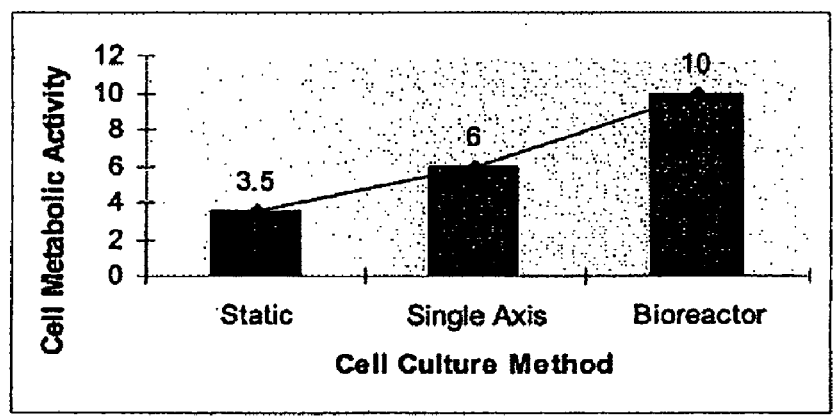
FIG. 33 shows a bar graph of cell metabolic activity of the goat chondrocytes cells grown statically, in a single rotating axis bioreactor and in the bioreactor of FIG. 1.
Figure 34:
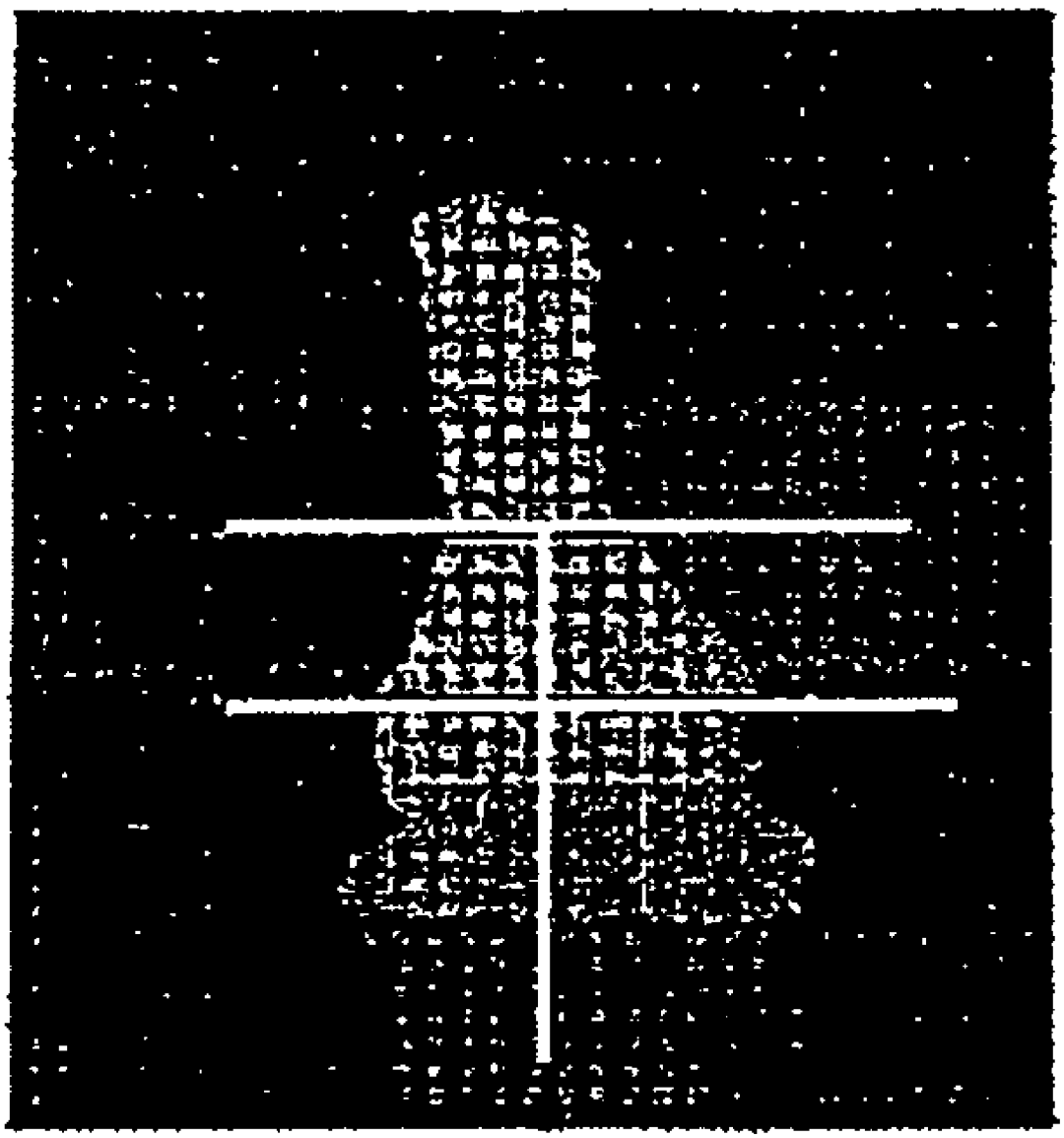
FIG. 34 shows schematic representation of the lines of cutting a scaffold into five pieces, made in an example disclosed herein.

FIG. 33 illustrates cell metabolic activity according to each of the three environments—static environment, single axis rotating reactor and the bioreactor 10. As can be clearly seen, the cell metabolic activity is highest in the bioreactor 10, followed by the single axis rotating reactor and lowest in the static environment. This indicates that the bioreactor 10 cultures tissue having cell-cell and cell-matrix interaction.

Example 1.4

Expansion of Cells

Step 1: Within the biosafety cabinet, spent media in a culture flask was pipetted out.

Step 2: 6 ml of trypsin was pipetted into the culture flask to dislodge the cells and the flask was incubated in the Binder CO2 incubator at 37° C., 5% $CO_2$.

Step 3: Once all cells are detached from the flask, 12 ml of DMEM media was added into the culture flask to stop trypsinisation.

Step 4: The contents in the culture flask were pipetted into a centrifuge tube and sent for centrifugation at 1000 rpm for 10 minutes.

Step 5: After centrifugation, the supernatant was removed and the residual cells were re-suspended in 5-10 ml of complete DMEM (Sterile) media.

Step 6: 15 µl of cell suspension was aliqouted out for cell counting and determining the total cell number.

Step 7: The cells were sub-cultured into many culture flasks with a specified cell density.

Step 8: The culture flasks are then incubated in the Binder CO2 incubator at 37° C., 5% $CO_2$.

Example 1.5

Preparation of a Scaffold and Seeding of the Scaffold

Step 1: In a biosafety hazard hood, scaffolds are placed into a sterile beaker. Ethanol was added to fill the entire beaker and left alone for 12 hrs.

Step 2: The ethanol was removed after 12 hrs and sterile PBS added to fill the entire beaker and left to stand for another 12 hrs.

Step 3: After 12 hrs, the PBS was removed and the scaffolds were dried by leaving them in the biosafety hazard hood for another 12 hrs Step 4: Within the biosafety cabinet, spent media in the culture flask were pipetted out. 6 ml of trypsin was pipetted into the culture flask to dislodge the cells.

Step 5: The flask was incubated at 37° C., 5% $CO_2$ in the bioreactor 10.

Step 6: Once all cells are detached from the flask, add 12 ml of complete DMEM (Sterile) into the culture flask to stop trypsinisation.

Step 7: The contents in the culture flask were pipetted into a centrifuge tube and send for centrifugation at 1000 rpm for 10 minutes.

Step 8: After centrifugation, the supernatant was removed and the residual cells re-suspended in 10 ml of DMEM media.

Step 9: The cell suspension is mixed with twice the amount of sterile sodium alginate solution to obtain a homogenous cell suspension. (4 mls of cell suspension per scaffold)

Step 10: The scaffolds were soak in sterile calcium chloride solution for a minute or so before it is seeded with the cells.

Step 11: While the scaffold is still dripping wet with the calcium chloride solution, 4 mls of the cell suspension with the sodium alginate is drawn and slowly seeded onto the scaffold. Any runoff is immediately sucked up onto the pipette and re-seeded onto the scaffold.

Step 12: After the 4 mls of cell suspension is seeded onto the scaffold, the scaffold is once again soaked in calcium chloride solution for a few seconds to make sure all the sodium alginate is coagulated to form a gel.

Step 13: The whole scaffold with the cells seeded is place in culture container with the media needed and incubated in the bioreactor 10 respectively.

Example 1.6

Different Types of Assays

MTS Assay

Step 1: Drain the medium from the wells containing the scaffolds and add 500 µl of fresh serum free basal medium into the wells.

Step 2: The plates were to be wrapped immediately in aluminium foil to avoid any light exposure.

Step 3: Add 100 µl of MTS reagent into each well.

Step 4: Incubate for 3 hrs in the 5% carbon dioxide bioreactor 10.

Step 5: After incubation, pipette the content of the wells to get a homogenous mixture and add 100 µl of the homogenized suspension into a 96 well culture plate.

Step 6: Read the sample using a plate reader at a wavelength of 490 nm and calculate the mean value to obtain the result.

FDA and PI Viability Assay

Step 1: A Propidium Iodide Stock Solution [10 mg/ml PI in PBS] is prepared by diluting 100 ml stock solution in 1 ml PBS.

Step 2: A Fluorescein Diacetate Stock Solution [5 mg/ml FDA in PBS], is prepared by diluting 40 ml stock solution in 10 ml PBS.

Step 3: The samples were washed with PBS for 2 times.

Step 4: Samples were incubated at 37° C. with FDA working solution for 15 minutes.

Step 5: FDA working solution was removed and rinsed the sample twice with PBS.

Step 6: PI working solution was added into each sample, making sure the solution had covered the entire sample and incubated for 2 minutes at room temperature.

Step 7: Samples were rinsed twice again with PBS and viewed under the Fluorescent Microscope.

Example 2

2.1 Path Line Plots

Using the fluid dynamics simulation software FLUENT™ from Fluent Inc of Lebanon, N.H., United States of America, simulation models were prepared for the cylindrical culture chamber 12 and spherical culture chamber 512. Standard path line plots showing velocity profiles of particles at various locations in the chamber were plotted for both chambers.

FIG. 42 shows a path-line plot the spherical culture chamber 512 in a dual axis bioreactor and FIG. 43 shows a path-line plot for the cylindrical culture chamber 12 in a dual axis bioreactor.

The flow regime generated within the spherical culture chamber, by the dual-axis system, is a non turbulent, low vortex flow regime that reduces cell damage and optimizes the expression of differentiated function and tissue development.

Path-line plots (FIG. 42 and FIG. 43) show that the spherical chamber 512 provides better mass transfer and distribution of nutrients to the three dimensional matrix as compared to the cylindrical culture chamber 12, placed under similar dual-axial motions.

Example 2.2

Three-Dimensional Bone Marrow Cell Culture

A method for culture of bone marrow cells using a dual axis bioreactor 510 comprising the spherical culture chamber 512 is described below.

2.2.1 Equipment Set Up and Sterility Test

Step 1: The spherical culture chamber 512, the T-Plug 520, knurled locking nut and bolt 504, gas exchange gland 522, tubing were washed with warm water and a mild liquid soap. Afterwards, all parts were washed with distilled water and rinsed with ultra-pure water overnight.

Step 2: The whole assembly was autoclaved at 121° C. for 20 minutes.

Step 3: For the sterility test, the chamber was filled with 500 ml yeast extract solution under sterile conditions and the closed system placed in an incubator (Jouan Incorporation, Paris, France) at 37° C., 5% $CO_2$. The sterility test was performed over a period of 4 days.

Step 4: The scaffolds were removed the static culture with forceps and positioned inside the cavity 510 with the help of the needles (530).

Step 5: The top chamber clamp plate 507 and top chamber clamp plate 508 were located in the respective places as shown in FIG. 39 and the chamber 512 was closed by means of knurled lock nut and bolt.

Step 6: The closed chamber 512 was fixed onto the bioreactor 10 and placed inside an incubator (Binder GmbH, Tuttlingen, Germany) at 37° C. and 5% $CO_2$.

Example 2.2.2

Derivation of Primary Rabbit Bone Marrow Cell Cultures

Step 1: New Zealand White rabbits were anaesthetised, shaved in the surrounding of the position of the iliac crest and the area sterilised by means of iodine solution.

Step 2: After a stab incision of the skin with a scalpel, rabbit bone marrow was harvested from the iliac crest with an aspiration needle and collected into heparin-coated syringes to prevent clotting.

Step 3: Primary cultures were initiated by addition of 3 ml rabbit bone marrow to 12 ml DMEM, supplemented with 10% PCS and 1% Streptomycin, into a 75 $cm^2$ cell culture flask.

Step 4: The flasks were placed in an incubator at 37° C. and 5% CO2, and the medium changed every 3-4 days until confluence of the cells was reached, thereby obtaining non-adherent haematopoietic cells.

Example 2.2.3

Establishment, Expansion and Cryopreservation of the Rabbit Bone Marrow-Derived Cell Strain Step 1: Confluent monolayers of bone marrow cells were obtained by the method described in example 2.2.2. The cells were washed with 1×PBSA and detached with 0.25% Trypsin/EDTA solution (Sigma, St. Louis, Mo., USA). The reaction was stopped by addition of 'complete DMEM' and the cells re-suspended. 'Complete DMEM' refers to DMEM (Sigma, St. Louis, Mo., USA) supplemented with FCS (Biological Industries, Israel) and 1% Streptomycin (Biological Industries, Israel).

Step 2: Viable cell counts with 0.4% w/v Trypan blue (Sigma, St. Louis, Mo., USA) were performed using an Improved Neubauer haemocytometer (Improved Neubauer, Weber, UK).

Step 3: The cell suspensions were diluted to half dilution and were seeded into culture flasks containing 'complete DMEM'. The flasks were placed in an incubator (Binder GmbH, Tuttlingen, Germany and Jouan, France) at 37° C. with 5% $CO_2$.

Example 2.2.4

Seeding of Rabbit Bone Marrow-Derived Cells onto Femur-Shaped PCL Scaffolds

Scaffold Sterilization

Step 1: One day prior to cell seeding, 12 femur-shaped PCL scaffolds (described in Example 1) were immersed into a 70% ethanol solution contained a 250 ml jar (Nalge Nunc, Rochester, N.Y., USA) and left Overnight.

Step 2: The scaffolds were then transferred to a new jar with lid containing approximately 150 ml PBSA solution, in order to remove all ethanol. After 2 hours, the PBSA solution was replaced with new PBSA solution and left for another 2 hours.

Step 3: The PBSA solution was decanted and replaced with 50 ml of 2% Fibrinogen solution (Baxter, Vienna, Austria). The closed jar was rolled for 20 minutes to ensure even distribution of the Fibrinogen solution over all scaffold surfaces and left for approximately 1 hour until the scaffolds were seeded with cells.

Harvesting of Rabbit Bone Marrow Cells

Step 4: For the seeding of the 12 scaffolds, 17 T-150 flasks with rabbit bone marrow-derived cells of 75-95% confluence were used.

Step 5: After one wash with 1×PBSA, the cells were enzymatically detached using 0.25% Trypsin solution (Sigma, St. Louis, Mo., USA). 'Complete DMEM' was added to stop the enzymatic reaction. The cells were re-suspended and the contents of multiple flasks were pooled together and alliquoted into 50 ml centrifuge tubes. The cells were centrifuged at 1500 rpm for 10 minutes. Cell pellets were re-suspended in complete DMEM and pooled into one centrifuge tube. Total volume was 6.6 ml. The total cell density was $28.2 \times 10^6$ with 98.6% viability.

Seeding of Rabbit Bone Marrow Cells onto the Scaffolds

Step 6: 3 ml Thrombin solution (Baxter, Vienna, Austria) with a concentration of 4 I.U./ml was prepared and added to the rabbit bone marrows-derived cell suspension to make a final volume of 9.6 ml. 800 µl of this cell-media-thrombin-solution was added to each scaffold, giving a total viable cell number of $2.3 \times 10^6$ per scaffold. The mixture was added very slowly into the shaft of each scaffold to ensure polymerization of the fiber-covering fibrinogen and the thrombin in the cell suspension ("fibrin glue"), in order to minimize any run-off from the scaffold leading to a loss of cells. Any run-off occurring due to very slow polymerization was immediately collected and pipetted back onto the scaffold.

Step 7: After seeding, 4 scaffolds each were placed into 500 ml jars with lid (Nalge Nunc, Rochester, N.Y., USA) and left in the laminar flow hood for 2.5 hours to improve cell attachment and polymerization of the fibrin glue in order prevent washing out cells upon addition of the cell culture media.

Step 8: After 2.5 hours, 'complete DMEM' was added slowly to the side of each jar until the scaffolds were completely covered. The closed jars were placed in an incubator (Binder GmbH, Tuttlingen, Germany) at 37° C. in 5% $CO_2$.

2.2.5 Transfer of Cells/Scaffold Constructs into Dynamic Culture

Step 1: After fourteen days under static culture conditions, four scaffolds were transferred into the culture chamber 512 of the dual axis bioreactor system 10. The transfer was carried out as described in example 2.2.1.

Step 2: The culture chamber 512 was fixed onto the dual axial bioreactor 10 and the bioreactor 10 was placed into an incubator (Binder GmbH, Tuttlingen, Germany) at 37° C. and 5% $CO_2$ and the "Jogging Mode" was chosen on the control panel, with settings as shown in Table 2.

TABLE 2

Parameters and settings of the dual-axis bioreactor 10 comprising spherical culture chamber 512 in Example 2.2.

|  | First Axis 516 | Second Axis 522 |
|---|---|---|
| Clockwise motion | 30° | 120° |
| Counter clockwise motion | 30° | 120° |
| Speed | 5 rpm | 5 rpm |

Step 3: The next four cell seeded-scaffolds were used for culture in the rotating-wall perfusion bioreactor. 500 ml new complete DMEM was used to fill the culture chamber of the rotating wall perfusion bioreactor. The whole system was placed inside an incubator (Jouan, France) at 37° C., 5% CO2 and connected to the control panel outside. A vessel rotation of 2 rpm was chosen and the media flow rate set to 3 ml/min.

Step 4: The last four cell-seeded scaffolds were placed into a jar with lid (Nalge Nunc, Rochester, N.Y., USA) and 500 ml new complete DMEM added. The closed jar was placed into an incubator (Jouan, France) at 37° C., 5% $CO_2$ with the lid slightly loosened to facilitate the gas exchange.

Example 2.3

Three-Dimensional Cell Culture of Human Trabecular Bone Chip Derived Cell Strain 2.3.1 Establishment, Expansion and Cryopreservation of the Human Trabecular Bone Chip-Derived Cell Strain.

Step 1: A human trabecular bone chip-derived cell culture, the cells being primary human cells, was derived by the explant method.

Step 2: The cells were cultured in T-150 flasks containing 'complete DMEM'. When confluent monolayers were obtained, the cells were washed with 1×PBSA and detached with 0.25% Trypsin solution (Sigma, St. Louis, Mo., USA). The reaction was stopped by addition of 'complete DMEM' and the cells were resuspended. Viable cell count was performed using an Improved Neubauer haemocytometer. The cell suspensions were diluted to half dilution and were reseeded into culture flasks containing complete DMEM. The flasks were placed in an incubator (Binder GmbH, Tuttlingen, Germany and Jouan, France) at 37° C. with 5% $CO_2$.

Step 3: In order to have, a backup of cells, sufficient amount of cells were banked as soon as a small surplus of cells became available at the first stages of passage. For banking, cells were washed, trypsmised, resuspended and a Trypan blue count carried out as described in step 2. Afterwards, the cells were centrifuged at 1500 rpm for 6 minutes to obtain cell pellets. The cell pellets were resuspended in 5 ml of 'media for cryopreservation' to obtain a cell concentration of $1 \times 10^6$ cells/ml. 'Media for cryopreservation' refers to complete DMEM further supplemented with 10% DMSO (Sigma, St. Louis, Mo., USA) and FCS (Biological Industries, Israel) to give a final concentration of 20% FCS. The media was filtered through a 0.22 µm ftlter prior to use. After 20 minutes, the cell suspension was aliquoted into cryogenic storage vials and the vials were transferred to −80° C. freezer. On the next day, the vials were transferred into a liquid nitrogen freezer.

2.3.2 Pre-Treatment of the Femur-Shaped PCL Scaffolds by Collagen Lyophilization and Sterilization—

Step 1: To provide a larger surface for cell attachment, increased seeding efficiency through a denser internal collagen network, and improved imitation of the extracellular matrix, 12 femur-shaped PCL scaffolds were lyophilized with collagen. Further, to prevent problems during the scaffold transfer into the spherical chamber 512, holes were punched into the scaffolds creating channel of appropriate size for locating the needles 530.

Step 2: Before lyophilization, the scaffolds were individually sterilized as described in example 2.2.4. Afterwards, the ethanol was removed and the scaffolds dried overnight in the open centrifuge tubes in a Biological Safety Cabinet Class II.

Step 3: For the lyophilization procedure, a 0.05% acetic acid solution was prepared from 100% acetic acid (Merck, Darmstadt, Germany) in deionised water. Rat-tail collagen, obtained via enzymatic digestion with collagenase, was used to prepare a 2.5 mg/ml rat-tail collagen solution in 0.05% acetic acid. The collagen solution was polymerized with sodium bicarbonate (71.2 mg/ml) into the PCL-scaffold at a volume ratio of 100:9. Therefore, for each scaffold 1500 µl of collagen solution and 135 µl of sodium bicarbonate were mixed in a 3 ml vial and added onto the scaffold in a petri-dish. The scaffold was left undisturbed for 15 minutes to improve polymerization. Afterwards, all scaffolds were frozen at −80° C. for 3 hours and subsequently freeze dried over night. Before seeding, the scaffolds were sterilized by 20 minute UV-irradiation.

2.3.3 Seeding of Human Trabecular Bone Chip-Derived Cells onto Collagen Lyophilized PCL Scaffolds Harvesting of Human Trabecular Bone Chip-Derived Cells Step 1: For the seeding of the 13 scaffolds, 14 T-150 flasks with human trabecular bone chip-derived cells of 65-85% confluence were used.

Step 2: After one wash with 1×PBSA, the cells were enzymatically detached with 0.25% Trypsin (Sigma, St. Louis, Mo., USA) and complete DMEM added to stop the enzymatic reaction. The cells were resuspended and the contents of multiple flasks combined in 50 ml centrifuge tubes. The cells were centrifuged at 1500 rpm for 10 minutes. Cell pellets were resuspended in 'complete DMEM' and pooled into one centrifuge tube, giving a final volume of 5 ml. The cell count with 0.4% w/v Trypan blue (Sigma, St. Louis, Mo.) resulted in a total cell number of $12.5 \times 10^6$ with 97.8% viability, giving a total of $12.2 \times 10^6$ viable cells.

Seeding of Human Trabecular Bone Chip-derived Cells onto the Scaffolds

Step 3: 2 ml Thrombin solution (Baxter Inc., Vienna, Austria) with a concentration of 4 I.U./ml was prepared with 102 mM calcium chloride and added to the 5 ml of human trabecular bone chip-derived cell suspension, prepared as described above, resulting in a final volume of 7 ml. 2% Fibrinogen solution (Baxter, Vienna, Austria) and sodium alginate (Sigma, St. Louis, Mo.) solution (2.5% w/v in 1×PBSA) were filled into separate syringes and some drops of each solution distributed over each scaffold. 500 µl of the cell/media/thrombin/calcium chloride solution was added into the stub of each scaffold and any run-off immediately pipetted back onto the scaffold. Each scaffold was put back into a centrifuge tube, the tube rolled for 5 minutes to ensure even distribution and incubated at 37° C. for approximately 30 minutes, giving time for the polymerization of the fibrinogen-thrombin and sodium alginate-calcium chloride solutions.

Step 4: Due to the fast degradation of the fibrin glue, the whole cell-scaffold construct was further coated with a sodium alginate layer by addition of 2 ml of sodium alginate solution (2.5% w/v) and 400 µl of 102 mM calcium chloride. The solution was directly added into each centrifuge tube and the tube was rolled until polymerization was visible (approximately 5-10 minutes). Each tube with a scaffold was incubated for 30 minutes at 37° C. before the scaffolds were carefully placed into 500 ml jars with lid (Nalge Nunc, Rochester, N.Y., USA), containing 200 ml 'complete DMEM'. The closed jars were placed in an incubator (Binder GmbH, Tuttlingen, Germany) at 37° C. and 5% $CO_2$, with the lid slightly loosened in order to ensure a gas exchange.

2.3.4 Transfer of Cell/Scaffold Constructs into Dynamic Culture

Step 1: After eleven days in static culture, four scaffolds were transferred into the bioreactor 10. The transfer was carried out as described in example 2.2.1.

Step 2: The culture chamber 512 was fixed onto the bioreactor 10 and it was placed inside an incubator (Binder GmbH, Tuttlingen, Germany) at 37° C. and 5% CO2.

The rotations about the primary and secondary axis were as shown in table 3.

TABLE 3

Parameters and settings of the dual-axis bioreactor 510 comprising spherical culture chamber 512 in example 2.3.

|  | Primary Axis (L-bracket) | Secondary Axis (culture chamber) |
| --- | --- | --- |
| Clockwise motion | 40° | 360° |
| Counter clockwise motion | 40° | 360° |
| Speed | 2 rpm | 2 rpm |

Step 3: The next four cell seeded scaffolds were used for culture in the rotating-wall perfusion bioreactor. 500 ml new complete DMEM was used to fill the culture chamber of the rotating wall perfusion bioreactor. The whole system was placed inside an incubator (Jouan, France) at 37° C., 5% CO2 and connected to the control panel outside. A vessel rotation of 2 rpm was chosen and the media flow rate set to 3 ml/min.

Static Culture

Step 4: The last four cell-seeded scaffolds were placed into a jar with lid (Nalge Nunc, Rochester, N.Y., USA) and 500 ml new complete DMEM added. The closed jar was placed into an incubator (Jouan, France) at 37° C., 5% $CO_2$ with the lid slightly loosened to facilitate the gas exchange.

2.4 Osteogenic Induction

For osteogenic induction, in examples 2.2, two days after the cell/scaffold construct transfer into the culture chamber 512, 50 ml of the medium in the culture chambers was replaced with 50 ml 10× osteogenic medium. 200 ml of a 10-fold medium was prepared by supplementing 90 ml of complete DMEM with 110 ml of FCS (Biological Industries, Israel), 100 mg L-ascorbic acid 2-phosphate (Sigma, St. Louis, Mo., USA), 4.3 g p-glycerophosphate (Sigma, St. Louis, Mo., USA), and 0.078 mg dexametbasone (Sigma, St. Louis, Mo., USA). This resulted in working concentrations of 15% CS, 50 µg/ml L-ascorbic acid 2-phosphate, 10 mM beta-glycerophosphate, and $1 \times 10^{-7}$ M dexamethasone in the culture chamber.

The same procedure was carried out for example 2.3, but osteogenic induction was performed seven days after the construct transfered into the culture chamber 512 to allow for enhanced cell proliferation in the dynamic culture systems prior to differentiation.

In the example 2.3, a control of osteogenic differentiation of the human cells in tissue culture flasks was included and initiated with 1× osteogenic media.

2.5 Removal and Preparation of Media Samples and Scaffolds for Analysis

During both examples 2.2 and 2.3, media samples were taken at different time points from all culture systems and immediately frozen at −80° C. until analysis. The samples were analyzed by specific enzyme-linked immunosorbent assays (ELISAs) for procollagen type 1, bone-specific alkaline phosphatase and osteocalcin as osteogenic markers, as well as by calorimetric assays for D-glucose, L-lactic acid and L-glutamine for the generation of a metabolic profile, analysing the supply of nutrients and the accumulation of acidic waste products, as all culture systems were run as batch-process.

Furthermore, scaffolds were removed from all culture systems at different time points. In the example 2.3, no scaffolds were analyzed during the period of dynamic cell culture to prevent contamination. Each scaffold was cut with scissors into 5 pieces (FIG. 44), however, due to the irregular shape it was not possible to ensure that all pieces had the same size. For the analysis by Confocal Laser Microscopy, one smaller piece each, of the shaft and from the inside of the condyle were cut front the bigger pieces; the five bigger pieces were analyzed for cell proliferation by alamarBlue™ assay and prepared for Scanning Electron Microscopy (SEM) afterwards.

2.6 Microscopical Analysis 2.6.1 Phase Contrast Light Microscopy

Cell cultures were examined on a routine basis for adhesion, proliferation, possible contaminations and exhaustion of the medium by means of an Olympus CK40 inverted microscope (Olympus America Inc, New York, United States of America) with phase-contrast and by eye. Further, cell morphology, the presence and/or establishment of a predominant cell type, as well as morphological changes due to passaging and cryopreservation were studied and documented with an Olympus Camedia C-4040 digital camera, installed onto the inverted microscope.

2.6.2 Scanning Electron Microscopy

Samples to be analyzed were immersed in 25% Glulardialdehyde for 30 minutes. The specimens were washed twice with PBSA solution and dehydrated in graded ethanol series of 50%, 75%, 90%, and 100% for 15 to 20 minutes for each grade. The samples were left for drying in an open centrifuge tube at 4° C. until analysis, but for a minimum of 1 day. The samples were viewed under a JEQL JSM-5300LV scanning electron microscope at 25 kV.

Figure 45A:
FIG. 45a shows a scanning electron microscopic image of a cell seeded scaffold cultured in static culture system after 32 days from the start of culture i.e. after 21 days in dynamic culture.
Figure 45B:
FIG. 45b shows a scanning electron microscopic image of a cell seeded scaffold cultured in a rotating wall perfusion bioreactor after 32 days from the start of culture i.e. after 21 days in dynamic culture.
Figure 45C:
FIG. 45c shows a scanning electron microscopic image of a cell seeded scaffold cultured in the dual-axis bioreactor of FIG. 1 after 32 days from the start of culture i.e. after 21 days in dynamic culture.

FIG. 45 a-c show scanning electron microscopic images of the cell seeded scaffolds cultured in the three culture systems viz. the static culture system, the rotating wall perfusion bioreactor and the dual axis bioreactor, after 32 days from start of the culture. The images refer to the cultures of example 2.3.

Referring to FIG. 45a and FIG. 45b, the cell seeded scaffold cultured in the static culture system and the cell seeded scaffold cultured in the dual axis bioreactor show high amounts of cells embedded in extra-cellular matrix. However, in the cell seeded scaffold cultured in the rotating wall perfusion bioreactor hardly any cells or extra-cellular matrix can be seen (FIG. 46c).

2.6.3 Confocal Laser Microscopy

Specimens were prepared for confocal laser microscopy by a cell viability assay, combining the fluorescent dyes fluorescein diacetate (FDA) and propidium iodide (PI). The nonpolar FDA is hydrolyzed by esterase enzymes in the cytoplasm of viable cells and polar, fluorescent fluorescein is accumulated in the cytoplasm, Due to its polarity, fluorescein is trapped within viable cells and the entire cytoplasm emits green fluorescence. On the other hand, PI is excluded by the plasma membrane of viable cells due to its cationic nature. As a characteristic feature during the initial phase of apoptosis is the preservation of the structural integrity and most of the plasma membrane function, PI penetrates only cells with damaged membranes, i.e. necrotic and late apoptotic cells, and forms a red complex with nuclear DNA [Schantz J T, Hutmacher D W, Chim H, Ng K W, Lim T C, Teoh S H, *Induction of ectopic bone formation by using human periosteal cells in combination with a novel scaffold technology*, Cell Transplant. 2002; 11(2):125-38.]

The sample preparation was carried out in dark. Samples were washed twice in sterile PBSA solution and incubated at 37° C. with 10 μg/ml of FDA (Sigma, St. Louis, Mo., USA) in PBSA for 15 minutes. After rinsing twice with PBSA solution, 100 μg/ml of PI (Sigma, St. Louis, Mo., USA) in PBSA was added and incubation carried out at room temperature for 2 minutes. Samples were rinsed again with PBSA and viewed under a Confocal Laser Microscope (Olympus FLUOVIEW 500).

FIG. 44a to FIG. 44f show confocal laser microscopic images of shaft sections and core of condyl sections of cell seeded scaffolds cultured in the three culture systems viz. the static culture system, the rotating wall perfusion bioreactor and the dual axis bioreactor, after 32 days from start of the culture. The images refer to the cultures of example 2.3.

Figure 44A:
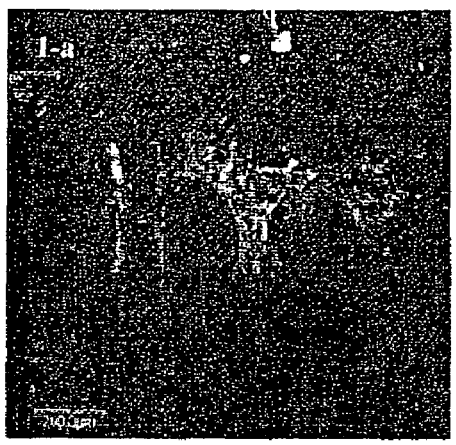
FIG. 44a shows a confocal laser microscopic image of the shaft section of a cell seeded scaffold cultured in a static culture system after 32 days from the start of culture.
Figure 44B:
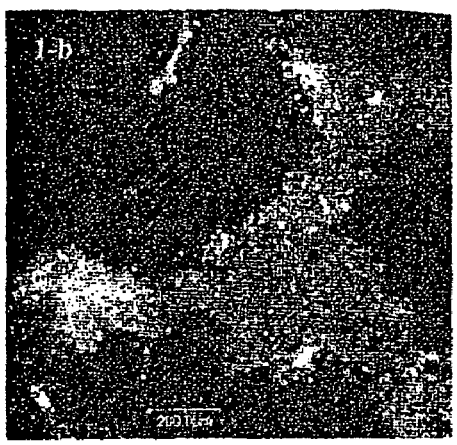
FIG. 44b shows a confocal laser microscopic image of core of the condyl section of a cell seeded scaffold cultured in a static culture system after 32 days from the start of culture.

Confocal laser microscopy analysis showed high cell numbers in the static culture, as well as in the dual-axis bioreactor. Referring to FIG. 44a and FIG. 44b, in all scaffolds of the static control, a high amount of live cells can be clearly seen in the shaft section (about 80%). The core part of the condyle section show a high number of cells organized in clusters and spread on the scaffold, but with a very high portion, of approximately 95% dead cells.

Figure 44C:
FIG. 44c shows a confocal laser microscopic image of the shaft section of a cell seeded scaffold cultured in a rotating wall perfusion bioreactor after 32 days from the start of culture i.e. after 21 days in dynamic culture.
Figure 44D:
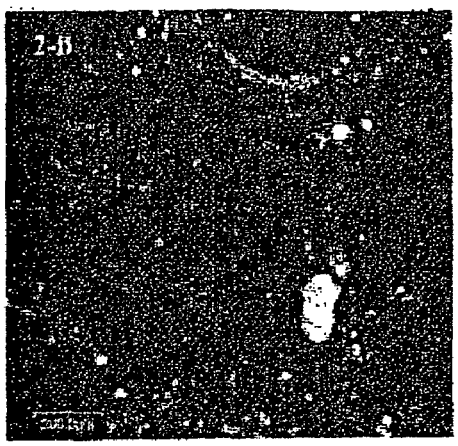
FIG. 44d shows a confocal laser microscopic image of core of the condyl section of a cell seeded scaffold cultured in a rotating wall perfusion bioreactor after 32 days from the start of culture i.e. after 21 days in dynamic culture.

Referring to FIG. 44c and FIG. 44d, on all three scaffolds of the RWV perfusion bioreactor, there hardly any cells can be seen. The small number of single, distributed cells can be seen in the shaft section and the core part of the condyle section.

Figure 44E:
FIG. 44e shows a confocal laser microscopic image of the shaft section of a cell seeded scaffold cultured in the dual-axis bioreactor of FIG. 1 after 32 days from the start of culture i.e. after 21 days in dynamic culture.
Figure 44F:
FIG. 44f shows a confocal laser microscopic image of core of the condyl section of a cell seeded scaffold cultured in the dual-axis bioreactor of FIG. 1 after 32 days from the start of culture i.e. after 21 days in dynamic culture.

Referring to FIG. 44e and FIG. 44f, the dual axis bioreactor 10 showed the highest amount of cells with around 80% viability in the shaft section of the scaffold. Also about 70% live cells can be seen at the core part of the condyle.

2.7 Imnimohistochemistry 2.7.1 alamarBlue™—Metabolic Activity Assay

Cell metabolization and proliferation was analyzed using the alamarBlue™ cell proliferation assay (Biosource, Calif., United States of America). The assay incorporates a fluometric/colorimetric growth indicator based on detection of metabolic activity. Specifically, the system incorporates an oxidation-reduction indicator that both fluoresces and changes colour in response to chemical reduction of growth medium resulting from cell growth.

For quantification purposes, cell standards were set up in duplicate (set A and B) in 24-well plates one day prior to analysis, at concentrations of 122,000-250,000 cells/ml in volumes of 2 ml complete DMEMb per well. The plates were placed in an incubator (Jouan, France) at 37° C., 5% $CO_2$.

On the day of the assay, specimens to be analyzed were placed individually in 24-well plates and the medium from set A of the cell standards removed. The subsequent procedure was carried out in dark. A 10% alamarBlue™ solution was prepared in basal DMEM (Sigma, St. Louis, Mo., USA), without serum. All wells (with cell standards and specimens) were rinsed with 2 ml/well PBSA first and then 2 ml/well 10% alamarBlue™ solution added. Two controls (2 ml/well) were included in duplicate viz. basal DMEM-only (control I) and 10% alamarBlue™ solution-only (control II). The plates were incubated (Jouan, France) in the dark at 37° C., 5% $CO_2$ for approximately 5 hours. After the incubation time, the wells were thoroughly mixed by means of a micropipette and three 100 μl samples from each well transferred into a 96-well micro-titer plate for calorimetric analysis. The absorbance was measured at 570 nm and 630 nm using a microplate reader (Dynatech MR 7000).

The percentage of reagent reduction was calculated as follows:

a) The absorbance of the control I was subtracted from the absorbance of control II at the lower wavelength (value called $AO_{LW}$), as well as at the higher wavelength (value called $AO_{HW}$).

b) A correction factor Ro was calculated on the basis of AOLW and AOHW, using the formula:

$$R_O = AO_{LW}/AO_{HW}$$

c) The absorbance ($A_{uncorrected}$) of each sample at both wavelengths was corrected by deducing the absorbance of control I at the respective wavelength; values corrected this way were called $A_{LW}$ and $A_{HW}$.

d) The percent of reduced alamarBlue™ was calculated as follows:

$$\% \text{ Reduced.} = A_{LW} - (A_{HW} \times R_o) \times 100$$

For the recovery of actual cell numbers used for the cell standard curve, a cell count was performed from set B of the cell standards. Each well was washed with 2 ml PBSA, 100 μl 0.25% Trypsin/EDTA (Sigma, St. Louis, Mo., USA) added and the plate incubated at 37° C., 5% $CO_2$ until cell detachment occurred. 400 µl/well complete DMEM was added and the suspension thoroughly mixed to ensure to get a single cell suspension, A viable cell count was performed with 0.4% w/v Trypan blue (Sigma, St. Louis, Mo., USA) and an Improved Neubauer haemocytometer.

Furthermore, it should be noted that the relationship between cell density and the percentage of reduced alamar-Blue™ is not linear and interpolation of the standard curve to determine the cell number is therefore not possible [Schantz J T and Ng K W., *A Manual for primary human cell culture*. World Scientific. Singapore 2004]

Figure 46A:
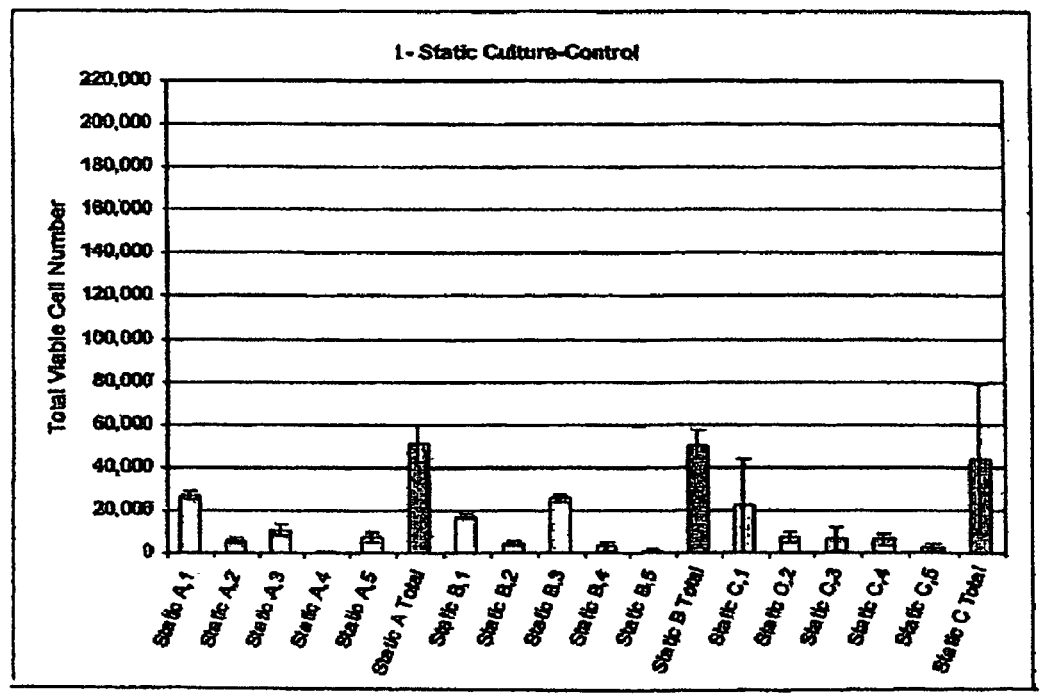
FIG. 46a shows a bar graph demonstrating total viable cells present in different sections of a cell seeded scaffold cultured in a static culture system after 32 days from the start of culture.
Figure 46B:
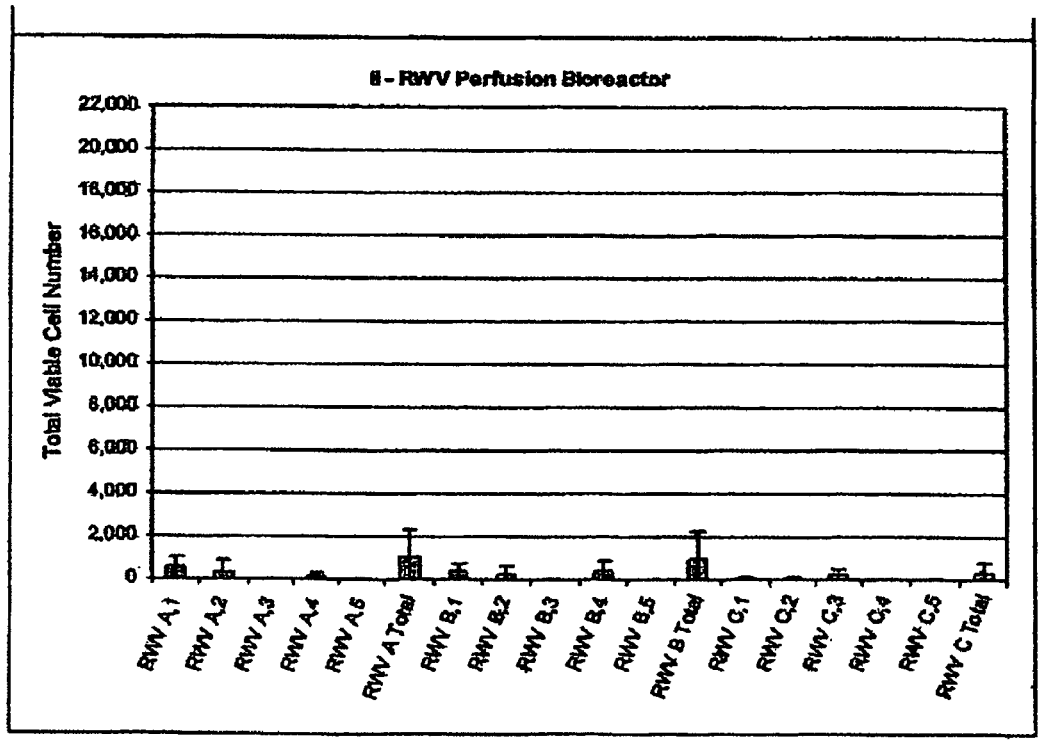
FIG. 46b shows a bar graph demonstrating total viable cells present in different sections of a cell seeded scaffold cultured in a rotating wall perfusion bioreactor after 32 days from the start of the culture.
Figure 46C:
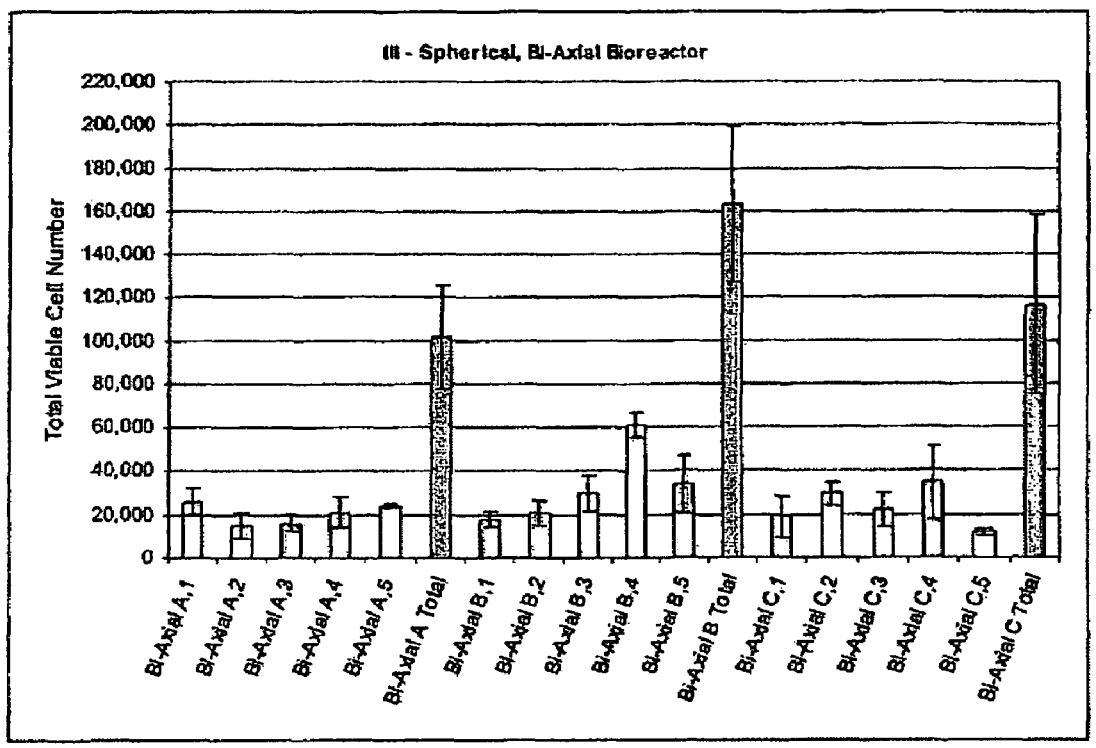
FIG. 46c shows a bar graph demonstrating total viable cells present in different sections of a cell seeded scaffold cultured in the dual-axis bioreactor after 32 days from the start of the culture.

FIG. 46a-c show bar graphs demonstrating total viable cells present in different sections of the cell seeded scaffolds cultured in the three culture systems after 32 days from the start of the culture. The data relates to example 2.3.

Referring to FIG. 46a-c, the analysis of viable cell numbers via alamarBlue™ assay, showed that the cell seeded scaffolds cultured in the dual-axial bioreactor have highest viable cell densities and the viable cells distributed evenly throughout the whole scaffold. The number of viable cells on the scaffolds cultured in the static culture system was lower than that of the dual axial bioreactor and it showed high levels of dead cells. On the scaffolds cultured in the rotating wall perfusion bioreactor, hardly any cells found.

2.7.2 Procollagen Type I Assay

For the detection of collagen type I in the supernatant of the culture systems, an enzyme immunoassay (Mefra™ CICP EIA kit) was purchased from Quidei (Marburg, Germany), which is originally used for the detection of C-terminal propeptide of type I collagen (CICP) in serum. Collagen is synthesized as pro-collagen, a larger precursor molecule. Pro-collagen consist of mature collagen with extension peptides at both amino and carboxy termini. These extension peptides, or propeptides, are cleaved from the collagen molecule by specific proteases prior to incorporation of collagen into a growing collagen Fibril and the release of these peptides into the circulation provides a stoichiometric representation of the production of collagen.

The CICP assay is a sandwich ELISA utilizing a monoclonal anti-CICP antibody coated on the plate, a rabbit anti-CICP antiserum, a goat anti-rabbit alkaline phosphatase conjugate, and a pNPP substrate. The minimum analytical detection limit of the assay is 0.2 ng/ml CICP.

The assay was performed as instructed by the manufacturer, with the exception that the samples were not diluted prior to analysis. Every standard, control and sample was included in duplicate in the tests. In brief, 100 µl Standard, Control or sample was added to each well of the coated plate and incubation carried out at 20° C. for 2 hours. Afterwards, the plate was emptied by inverting and washed by adding at least 300 µl per well of 1× Wash Buffer for a total of three washes. The plate was blotted dry on paper towels, 100 µl Rabbit anti-CICP added to each well and incubation carried out at 20° C. for 45-50 minutes. After another washing step, carried out as described before, 100 µl of Enzyme Conjugate was added to each well and incubation carried Out at 20° C. for 45-50 minutes, followed by a third washing step. 100 µl Substrate Solution was added per well, incubated for 30-35 minutes at 20° C. and the reaction stopped by addition of 50 µl Stop Solution per well. The optical density was read at 405 nm with an ELISA plate reader. A quantification software (SigmaPlot 9.0) with a 4-parariieter calibration curve fitting equation ($y=(A-D)/(1+(x/C)^B)+D$) was used for the standard curve and the basis for the determination of the concentrations of the samples.

Figure 50:
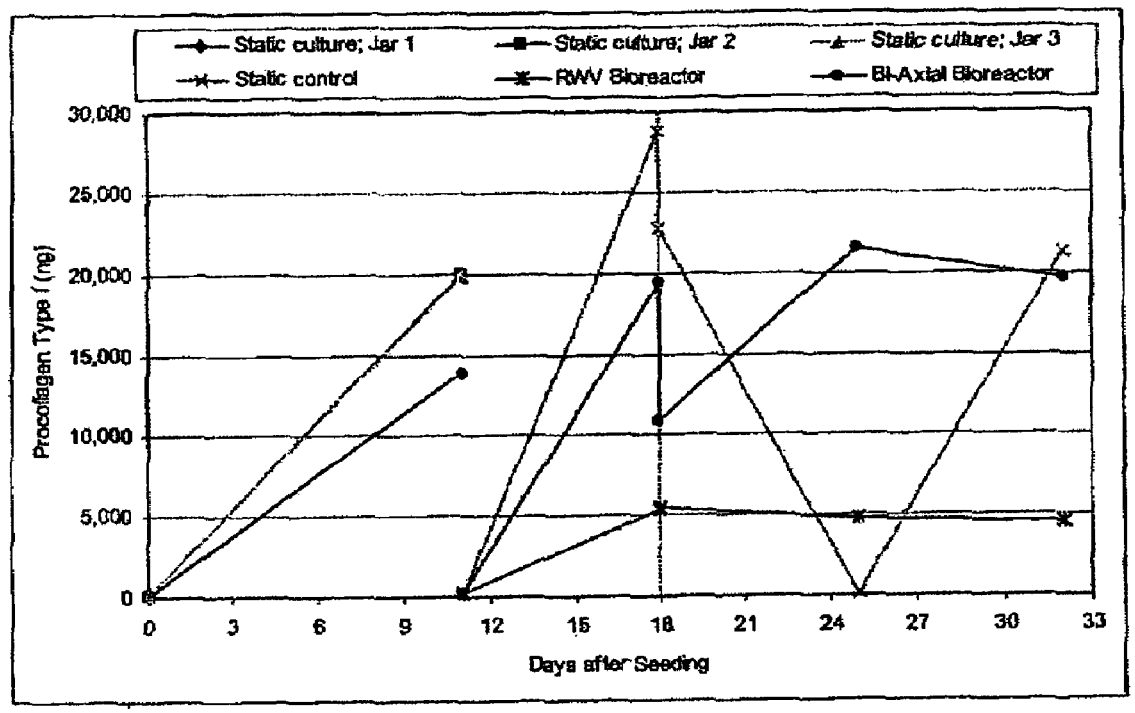
FIG. 50 shows a profile of Procollagen type I (CICP) synthesis over the culture period of 32 days in the three culture systems viz. the static culture system, the rotating wall perfusion bioreactor and the dual axis bioreactor.

FIG. 50 shows a profile of Procollagen type I (CICP) synthesis over the culture period of 32 days in the three culture systems viz. the static culture system, the rotating wall perfusion bioreactor and the dual axis bioreactor. It can be clearly seen from FIG. 50 that the cell seeded scaffold cultured in the static culture system show highest rate of CICP synthesis followed by the dual axis bioreactor. The cell seeded scaffold cultured in the rotating wall perfusion bioreactor show slowest rate of CICP synthesis.

2.7.3 Osteocalcin Assay

For the detection of intact osteocalcin in the supernatant of the culture systems, an enzyme immunoassay (Metra™ Osteocalcin EIA kit) was purchased from Quidet (Marburg, Germany), which is originally used for the detection of osteocalcin in serum. Osteocalcin (OC) has a molecular weight of 5800 and is a vitamin K dependent protein. The OC assay is a competitive ELISA utilizing osteocalcin coated strips, a mouse anti-osteocalcin antibody, an anti-mouse IgG-alkaline phosphatase conjugate and a pNPP substrate. The minimum detection limit of the assay is 0.45 ng/ml osteocalcin.

The assay was performed as specified by the manufacturer. Every standard, control and sample was included in duplicate in the tests, lit brief, 25 µl Standard, Control or sample was added to each well of the coated plate, followed by 125 µl anti-Osteoealcin solution, per well and incubation carried out at 20° C. for two hours. Afterwards, the plate was emptied by inverting and washed by adding at least 300 µl per well of 1× Wash Buffer for a total of three washes. The plate was blotted dry on paper towels, 150 µl Enzyme Conjugate added to each well and incubation carried out at 20° C. for 60 minutes. After another washing step, performed as described before, 150 µl of Substrate Solution was added to each well, incubation carried out at 20° C. for 30-40 minutes, and the reaction stopped by addition of 50 µl Stop Solution per well. The optical density was read at 405 nm with an ELISA plate reader. A quantitation software (SigmaPlot 9.0) with a parameter calibration curve fitting equation ($y=(A-D)/(1+(x/C)^B)+D$) was used for the standard curve and the basis for the determination of the concentrations of the samples.

Figure 51:
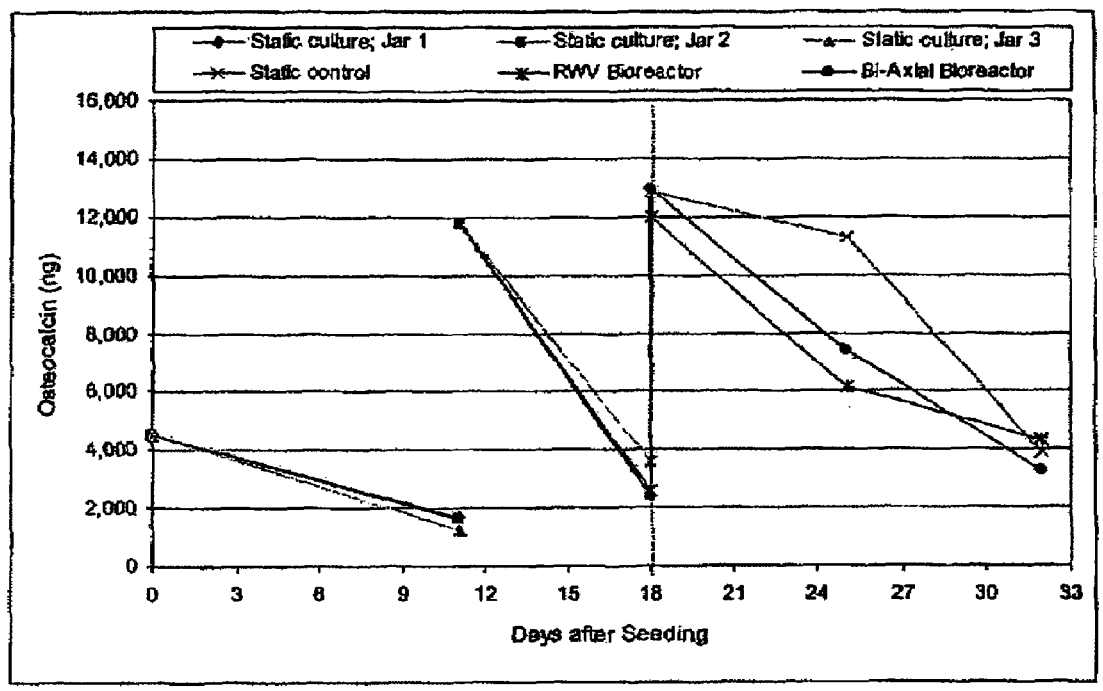
FIG. 51 shows a profile of osteocalcin synthesis over the culture period of 32 days in the three culture systems viz. the static culture system, the rotating wall perfusion bioreactor and the dual axis bioreactor.

FIG. 51 shows a profile of osteocalcin synthesis over the culture period of 32 days in the three culture systems viz. the static culture system, the rotating wall perfusion bioreactor and the dual axis bioreactor.

It is clearly evident from FIG. 51 that no synthesis of osteocalcin occur in any of the three systems. After osteogenic induction, the rotating wall perfusion bioreactor show fastest consumption of osteocalcin followed by the dual axis bioreactor. The static culture system shows lowest rate of ostocalcin consumption.

2.7.4 Bone-Specific Alkaline Phosphatase Assay

For the detection of bone-specific alkaline phosphatase (BAP) in the supernatant of the culture systems, an enzyme immunoassay (Metra™ BAP E1A kit) was purchased from Quidel (Marburg, Germany), which is originally used for the detection of BAP in human serum. The skeletal, or bone-specific, isoform of alkaline phosphatase is a tetrameric glycoprotein found on the surface of psteoblasts.

The BAP assay is an ELISA utilizing a monoclonal anti-BAP antibody coated on the plate and the enzymatic activity of the captured BAP in the sample is detected by means of a pNPP substrate. The minimum detection limit of the assay is 0.7 U/l bone-specific alkaline phosphatase. The assay was performed as instructed by the manufacturer; every standard, control and sample was included in duplicate in the tests. In brief, 125 µl Assay Buffer was added to each well, followed by 20 µl per well of Standard, Control or sample and the plate swirled gently to ensure mixing of sample and buffer. After an incubation period of 3 hours at 20° C., the plate was emptied by inverting and washed by adding at least 300 µl per well of 1× Wash Buffer for a total of three washes. The plate was blotted dry on paper towels, 150 µl Substrate Solution added to each well and incubation carried out at 20° C. for 30 minutes. The reaction was stopped by addition of 100 µl Stop Solution per well and the optical density read at 405 nm with an ELISA plate reader A quantification software (SigmaPlot 9.0) with a quadratic calibration curve fitting equation ($y = A + Bx + Cx^2$) was used for the standard curve and the basis for the determination of the concentrations of the samples.

Figure 52:
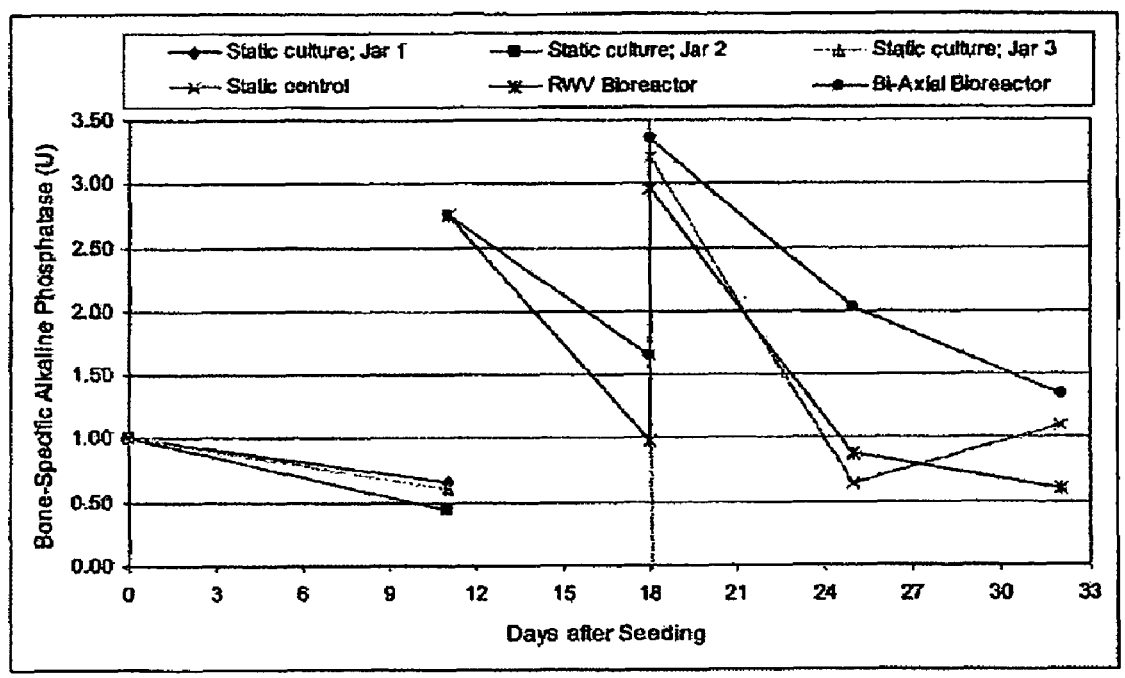
FIG. 52 shows a profile of bone alkaline phosphatase synthesis over the culture period of 32 days in the three culture systems viz. the static culture system, the rotating wall perfusion bioreactor and the dual axis bioreactor.

FIG. 52 shows a profile of bone alkaline phosphatase synthesis over the culture period of 32 days in the three culture systems viz. the static culture system, the rotating wall perfusion bioreactor and the dual axis bioreactor.

Bone alkaline phosphatase (BAP) shows a profile similar to that of osteocalcin. It can be seen from FIG. 52 that synthesis of BAP does not occur in any of the three systems. After osteogenic induction, the static culture system consumes BAP at the fastest rate while the dual axis bioreactor system consumes BAP at the lowest rate.

2.8 Metabolic Profile 2.8.1 D-Glucose Assay

The consumption of D-glucose by the cells seeded onto the scaffolds was quantified by means of an appropriate test kit, purchased from BOEHRINGER MANNHEIM/R-BIOPHARM (Darmstadt, Germany).

The assay was based on the following principle:

D-Glucose is phosphorylated to D-grucose-6-phosphate (G-6-P) in the presence of the enzyme hexokinase (HK) and adenosine-5'-triphosphate (ATP) with the simultaneous formation of adenosine-5'-diphosphate (ADP). In the presence of the enzyme glucose-6-phosphate dehydrogenase (G6P-DH), G-6-P is oxidized by nicotinamide-adenine dinucleotide phosphate (NADP) to D-glueonate-6-phosphate with the formation of reduced nicptinamide-adenine dinucleotide phosphate (NADPH). The amount of NADPH formed in this reaction is stoichiometric to the amount of D-glucose. The increase in NADPH is determined by means of its light absorbance at 340 nm.

The assay was performed according to the manufacturer's instructions. Prior to analysis, the samples were prepared in a water bath at 80° C. for 15 minute to stop enzymatic reactions, centrifuged and the supernatant used for the assay. In order to get a sufficient absorbance difference for the assay, the samples were diluted in water to yield a D-glucose concentration between 0.08 and 0.5 g/l.

The assay was carried out by direct addition of 1 ml solution 1 (containing buffer, NADP, ATP and magnesium sulfate), 0.1 ml sample solution (expect for the blank) and 1.9 ml redistilled water (2 ml for the blank) into reusable cuvettes. The solution was mixed and the absorbance ($A_1$) read at 340 nm against water, after approximately 3 minutes. Afterwards, the reaction was started by addition of 20 µl solution 2 (containing hexofcinase and glueose-6-phosphate dehydrogenase). The solution was mixed and the absorbance ($A_2$) read again at 340 nm against water, after approximately 15 minutes.

The concentration of D-glucose In each sample was calculated as prescribed by the manufacturer:

a) The absorbance difference ($A_2-A_1$): for both, blank and sample was determined and the absorbance difference of the blank subtracted from the absorbance difference of the sample:

$$\Delta A = (A_2-A_1)_{sample} - (A_2-A_1)_{blank}$$

b) According to the general equation for calculating the concentration:

$$C = \frac{V \times MW}{E \times d \times v \times 1000} \times \Delta A \times F [g/l]$$

$V$ = final volume [ml]

$v$ = sample volume [ml]

MW = molecular weight of assayed substance [g/mol]

$d$ = light path [cm]

$E$ = extinction coefficient of NADPH (at 340 nm = 6.3 $[1 \times mmol^{-1} \times cm^{-1}]$)

$F$-dilution factor

It followed for D-glucose:

$$C = \frac{5.441}{6.3} \times \Delta A \times F \left[ g_{D\text{-}glucose}/l \right]$$

Figure 47:
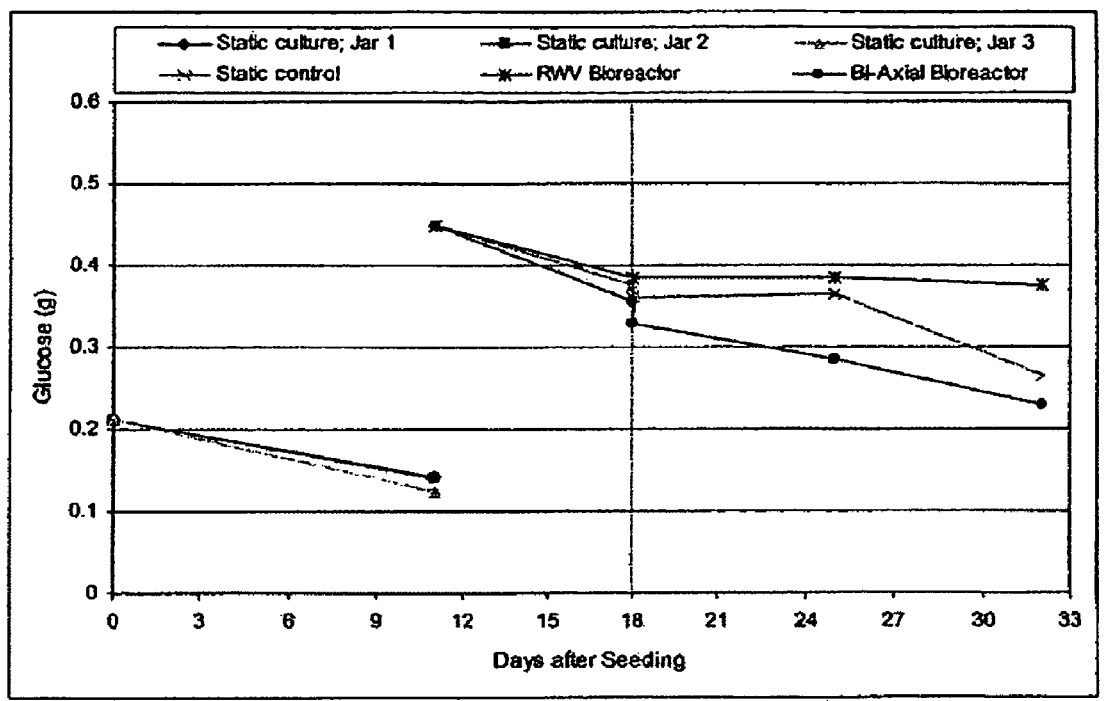
FIG. 47 shows a profile of total available mass of glucose in the culture media over the culture period of 32 days for the three culture systems viz. the static culture system, the rotating wall perfusion bioreactor and the dual axis bioreactor.

FIG. 47 shows a profile of total available mass of glucose in the culture media over the culture period of 32 days for the three culture systems viz. the static culture system, the rotating wall perfusion bioreactor and the dual axis bioreactor.

It can be seen from FIG. 47 that during the initial static culture period, the available mass in all jars (4 scaffolds and 200 ml media each) showed an equal decrease. After the transfer of 4 scaffolds each into the three culture systems (500 ml media each), the dual axis bioreactor showed the highest rate of glucose breakdown, followed by the static culture system. The glucose concentration in the RWV perfusion bioreactor is nearly constant, suggesting that nearly no cellular metabolism and growth is taking place in this culture system.

2.8.2 L-Lactic Acid Assay

The production of L-Lactic acid by the cells seeded onto the scaffolds, was quantified by means of an appropriate test kit, purchased from BOEHRINGER MANNHEIM/R-BIOPHARM (Darmstadt, Germany).

The assay is based on the following principle:

L-Lactic acid is oxidized to pyruvate by nicotinamide-adenine dinucleotide (NAD) in the presence of L-lactate dehydrogenase (L-LDH). The equilibrium of this reaction lies on the side of L-lactic acid. By trapping pyruvate in a subsequent reaction catalyzed by the enzyme glutamate-pyfuvate transaminase (GPT) in the presence of L-glutamate, the equilibrium can be displaced in favour of pyruvate and NADH. The amount of NADH formed in this reaction is stoichiometric to the amount of L-lactic acid. The increase in NADH is determined by means of its light absorbance at 340 nm.

The assay was performed according to the manufacturer's Instructions, with the change that only half of the volumes of every solution were used. Prior to analysis, the samples were prepared in a water bath at 80° C. for 15 min to stop enzymatic reactions, centrifuged and the supernatant used for the assay.

In order to get a sufficient absorbance difference, the sample solution was appropriately diluted in water to yield an L-lactic acid concentration between 0.03 and 0.2 g/l.

The assay was carried out by direct addition of 500 ml solution 1 (containing buffer and Lirglutamic acid), 100 ml solution 2 (containing NAD), 10 µl suspension 3 (containing glutamate-pyruvate transaminase), 50 µl sample solution (expect for the blank) and 450 µl redistilled water (500 µl for the blank) into reusable cuvettes. The solution was mixed and the absorbance (A1) read at 340 nm against water, after approximately 5 minutes. Afterwards, the reaction was; started by addition of 10 µl solution 4 (containing L-lactate dehydrogenase). The solution was mixed and the absorbance (A2) read again at 340 nm against water, after approximately 30 minutes.

The concentration of L-lactic acid in each sample was Calculated as prescribed by the manufacturer:

a) The absorbance difference ($A_2-A_1$) for both, blank and sample was determined and the absorbance difference of the blank subtracted from the absorbance difference of the sample:

$$\Delta A = (A_2-A_1)_{sample} - (A_2-A_1)_{blank}$$

b) According to the general equation for calculating the concentration:

$$C = \frac{V \times MW}{E \times d \times v \times 1000} \times \Delta A \times F [g/l]$$

$V$ = final volume [ml]

$v$ = sample volume [ml]

MW = molecular weight of assayed substance [g/mol]

$d$ = light path [cm]

$E$ = extinction coefficient of NADPH (at 340 nm = 6.3 [$1 \times mmol^{-1} \times cm^{-1}$])

$F$ = dilution factor

It followed for L-lactic acid:

$$C = \frac{2.018}{6.3} \times \Delta A \times F \; [g_{L-lactic\;acid}/l]$$

Figure 48:
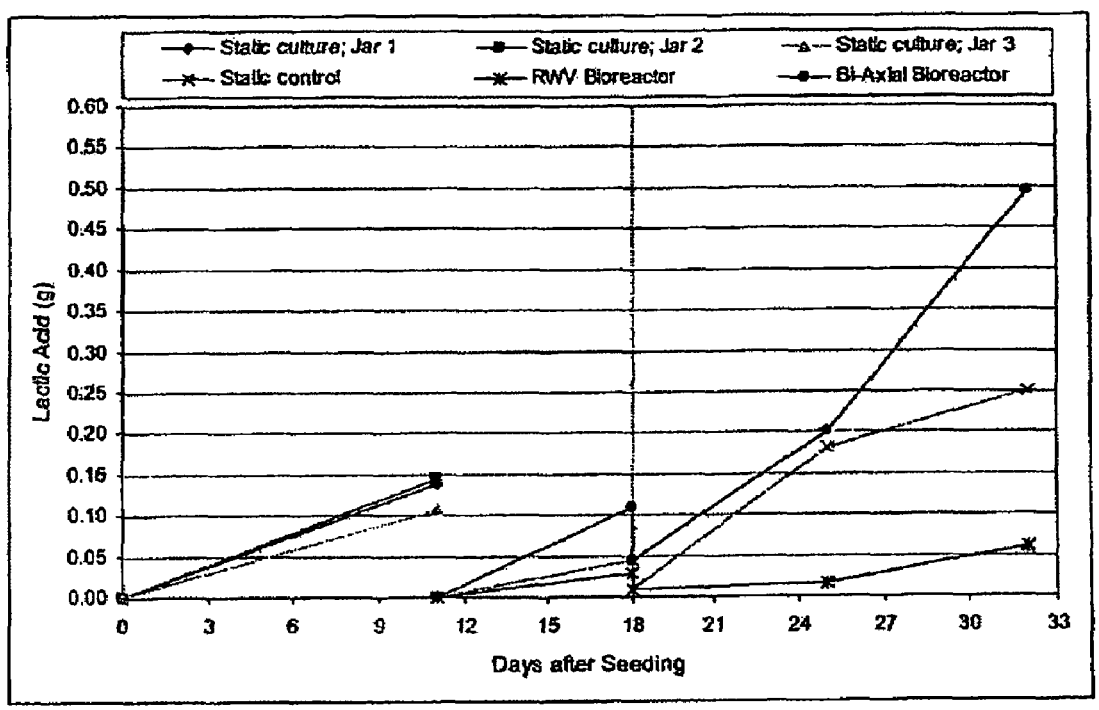
FIG. 48 shows a profile of lactic acid content in the culture media over the culture period of 32 days for the three culture systems viz. the static culture system, the rotating wall perfusion bioreactor and the dual axis bioreactor.

FIG. 48 shows a profile of lactic acid content in the culture media over the culture period of 32 days for the three culture systems viz. the static culture system, the rotating wall perfusion bioreactor and the dual axis bioreactor.

It is seen from FIG. 48 that the lactic acid content in the media of all jars increases during the initial static period, but at a slightly different rates suggesting that the oxygen supply is not uniform in the three vessels. In dynamic cultures, the media of rotating wall perfusion bioreactor showed insignificant increase of the lactic acid concentration over the complete culture period suggesting that a small number of viable cells are present in the system. The other two culture systems viz. the static culture system and the dual axis bioreactor show a nearly similar lactate content profile.

2.8.3 Glutamine Assay

The consumption of glutamine by the cells seeded onto the scaffolds was quantified by means of an appropriate test kit specially designed for use in cell culture and purchased from Sigma (St. Louis, Mo., USA).

The assay is based on the reductive deamination of L-glutamine by a proprietary enzyme. Quantitation is accomplished by linking a dye directly to the reductive reaction. The reaction is specific for L-glutamine and does not cross-react with other amino acids or ammonia.

The assay was performed according to the manufacturer's instructions. First, a glutamine standard curve including concentrations from 0 mM to 6 mM was prepared, in provided dilution buffer. Afterwards, internal standards (one internal standard for each medium to be assayed) were prepared in Eppendorf tubes by addition of 50 µl reaction buffer, 300 µl sample, 10 µl undiluted standard solution and 490 µl dilution buffer ('spiked samples'). 'Un-spiked samples' were prepared in Eppendorf tubes by addition of 50 µl reaction buffer, 300 µl sample (or standard curve dilution) and 500 µl dilution buffer. The reaction was started by addition of 150 µl enzyme solution and all tubes were incubated for one hour in a 37° C. water bath. After the incubation period, 100 µl colour reagent was added to each tube, mixed thoroughly and left at room temperature for 5 minutes. Afterwards, the content of each tube was transferred to a 1 ml cuvette and the absorbance read at 550 nm using a spectrophotometer.

The concentration of L-glutamine in each sample was calculated as described by the manufacturer:

a) A linear regression analysis of the standard curve was performed and the slope of the regression line was used to calculate the uncorrected L-glutamine concentration of the samples.

b) The recovery of the internal standard was used to correct the data obtained in the assay for deviations caused by the interaction of media components with the test.

The following formula was used to calculate the recovery value:

$$\text{Recovery value} = D = \frac{(A-B)}{C}$$

$A$ = [L-glutamine] in the spiked sample $B$ = [L-glutamine] in the unspiked sample $C$ = [L-glutamine] added as internal standard (i.e. 2 mM when 10 µl of standard was used)

$D$ = Recovery value c) The concentration of L-glutamine in each samples was corrected for any inhibition/enhancement using the recovery value, according to the following formula $$[\text{L-glutamine}]_{corrected} = \frac{E}{D}$$

$E$ = [L-glutamine] uncorrected in an unspiked sample.

Figure 49:
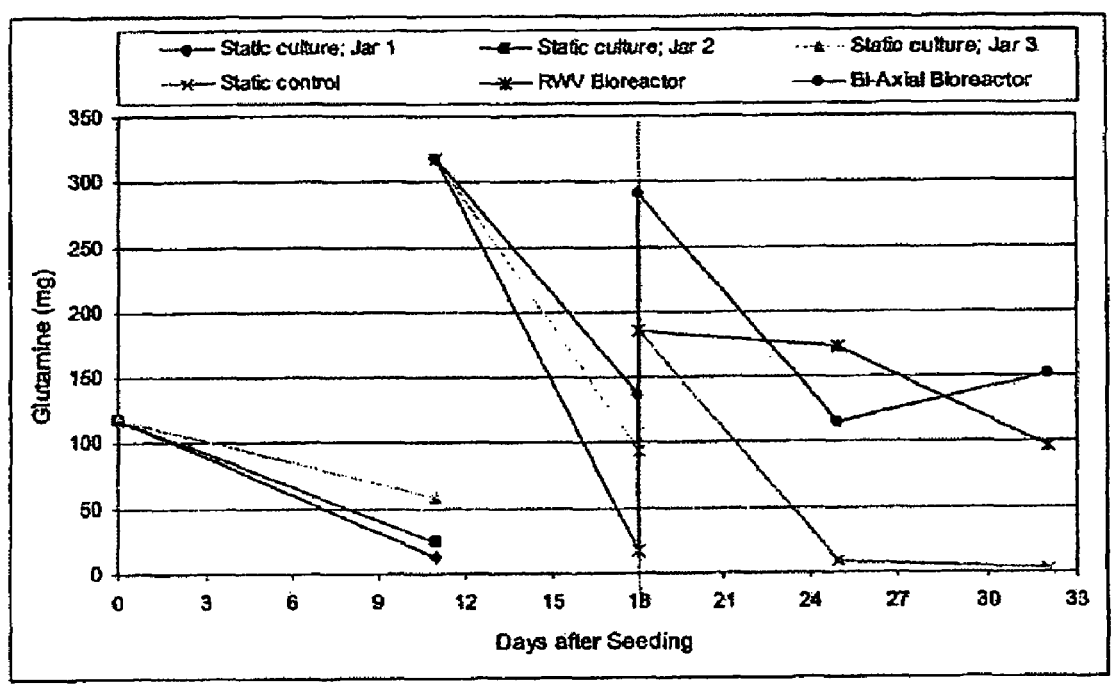
FIG. 49 shows a profile of total available mass of glutamine in the culture media over the culture period of 32 days for the three culture systems viz. the static culture system, the rotating wall perfusion bioreactor and the dual axis bioreactor.

FIG. 49 shows a profile of total available mass of glutamine in the culture media over the culture period of 32 days for the three culture systems viz. the static culture system, the rotating wall perfusion bioreactor and the dual axis bioreactor.

From FIG. 49 it can be observed that after transfer of the cell seeded scaffold the concentration of glutamine in all three culture systems showed a sudden decrease. The rotating wall perfusion bioreactor showed the fastest decrease. The rate of glutamine depletion in the dual-axis bioreactor was the lowest suggesting a more efficient metabolism in the dual-axis bioreactor.

2.9 Implantation of Cultured Constructs into a Nude Rat Model

In the example 2.3, one cell/scaffold construct of each culture system was implanted into two nude rats under sterile conditions in a laminar flow hood, one day after removal of all scaffolds from the different systems (day 32). Housing and feeding of the rats was done according to standard animal care protocols.

The constructs were prepared by removing any sharp edges and cutting each scaffold longitudinally in half with a scalpel; one half was used for implantation. The rats were anesthetized, placed in a prone position on the table and the backs prepared with 70% alcohol. An approximately 5-cm long incision, slightly left of the spines was made, a subcutaneous pocket created into which the implants were inserted and the wound closed by sutures. Two scaffolds were implanted into rat A, the static culture-construct on the right side and the rotating-wall perfusion bioreactor-construct on the left side; the spherical biaxial bioreactor-construct was implanted into the right side of rat B.

Example 3.1

Three-Dimensional Cell Culture Preparation Using the Dual Axis Bioreactor with Spherical Chamber The procedures outlined below shows the steps to grow a three-dimensional culture in vitro using the system 400' as follows:

Step 1: Human fibroblast cells is grown to confluency in a 150 $cm^{-2}$ Falcon tissue culture flask containing 20 ml. of a culture medium consisting of Dulbecco's modified Minimum Essential Medium (MEM) containing 10% fetal calf serum. Dulbecco's modified Minimum Essential Medium is a standard commercially available culture medium obtained from Microbiological Associates, Bethesda, Md., United States of America.

Step 2: The spent culture medium is removed from the flask and the fibroblast cell growth was trypsinized with 2 ml of 0.25% trypsin in phosphate buffered saline for three minutes.

Step 3: The trypsin is inactivated by dilution with a 20 ml portion of the same culture medium.

Step 4: The fibroblast cells is then transferred to a sterile syringe.

Step 5: The chamber 512 of the bioreactor 10, the feed line 106, the product line 108 are sterilized and then equilibrated by priming with Dulbecco's modified Minimum Essential Medium (MEM) containing 2% fetal calf serum.

Step 6: A three-dimensional matrix or scaffold is secured onto the mount provided in the chamber 512. The scaffold is inoculated with 30 ml of the fibroblast cell suspension in the syringe of step 4 to begin incubation of the fibroblast cells. Media is pumped into the chamber via inlet 502*a*.

Step 7: The bioreactor 10 is then placed inside a $CO_2$ incubator. Using the control unit 412', bioreactor 10 is activated to rotate the chamber 512 about the two principal axes (16,22) respectively in the directions of arrows (18,24).

Step 8: The media within the chamber is maintained at a temperature of 37° C. within the $CO_2$ incubator.

Step 9: The chamber 512 was allowed to incubate to grow cells for 3 days.

Step 10: At the termination of incubation, the scaffold is removed from the chamber 512.

Preparation of Media and Reagents

The reagents in examples 2.2 to 2.6 are prepared as described in Example 1.

Example 3.2

Isolation of Chondrocytes/Cartilage from Pig's Ears

Step 1: Surface sterilization was conducted on the pig's ears in a bio-safety cabinet. Three beakers were filled with iodine, alcohol and PBS respectively. The pig's ears are then soaked in each beaker for 15 minutes.

Step 2: The ears were placed on a sterile plate and the skin and other muscle tissues removed leaving behind only the cartilage.

Step 3: The cartilage was transferred onto a new sterile plate and cut into thin slices. This facilitates digestion at a later stage. A small amount of PBS was added to keep the cartilage wet. The thin slices of cartilage were then aseptically transferred into 50 ml centrifuge tubes.

Step 4: Collagenase II was added into the centrifuge tubes to form a cell suspension. The tubes were placed into a shaking incubator for 16-18 hrs at 37° C. to ensure homogenous digestion. Digested cartilage is indicated by a change in color of the collagenase II from red to yellow with turbidity.

Step 5: A little of the digested cartilage was removed and tested for contamination using an inverted microscope.

Step 6: The cell suspension is then filtered through a sterile nylon filter to remove any undigested cartilage.

Step 7: 20 ml of PBS was added to the filtered cell suspension, and the resulting mixture centrifuged at 2500 rpm for 5 min.

Step 8: The supernatant resulting from the centrifuge was carefully poured away and the residual cartilage (also known as chondrocytes) was washed with PBS to remove the collagenase II.

Step 9: The centrifuge tubes containing the washed cartilage was inverted and centrifuged at 2500 rpm for 3 minutes. Thereafter, the PBS was removed from the centrifuge tubes.

Step 10: 10 ml DMEM media was added to the cartilage, followed by a transfer into a T-25 flask to check for contamination under a microscope.

Step 11: The isolated cartilage tissue can then be placed in the bioreactor 318. Conditions therein are at a temperature of 37° C. and 5% volume $CO_2$.

A three-dimensional cartilage tissue was obtained in which cartilage tissue had cell-cell and cell-matrix interactions that were characteristic of in vivo cartilage tissue.

Example 3.3

Thawing and Maintenance of Cells

Step 1: A cryovial of Goat Chondrocyte cells was removed from liquid nitrogen and placed them immediately into a water bath set at 37° C. for less than 1 minute until the last trace of ice vanishes.

Step 2: The cryovial was then removed from the water bath and sprayed with 70% ethanol before placing it in the bio-safety cabinet.

Step 3: The cryovial was then transferred into a centrifuge tube containing 9 ml sterile DMEM media and spun at 1500 rpm for 6 minutes.

Step 4: After centrifugation, the supernatant was removed and the residual cryovial was re-suspended in 2 ml sterile DMEM media. About 15 µl of the suspension is then removed for analysis on the number of viable cells count.

Step 5: More than 1×10$^5$ cells/ml were then seeded into a T-75 flask with 20 ml sterile DMEM media, and the cells were incubated.

Step 6: Cell growth was examined daily and replenished with fresh DMEM every 3 days.

Example 3.4

Expansion of Cells

Step 1: Within the biosafety cabinet, spent media in a culture flask was pipetted out.

Step 2: 6 ml of trypsin was pipetted into the culture flask to dislodge the cells and the flask was incubated.

Step 3: Once all cells are detached from the flask, 12 ml of DMEM media was added into the culture flask to stop trypsinisation.

Step 4: The contents in the culture flask were pipetted into a centrifuge tube and sent for centrifugation at 1000 rpm for 10 minutes.

Step 5: After centrifugation, the supernatant was removed and the residual cells were re-suspended in 5-10 ml of complete DMEM (Sterile) media.

Step 6: 15 µl of cell suspension was aliqouted out for cell counting and determining the total cell number.

Step 6: The cells were sub-cultured into many culture flasks with a specified cell density.

Step 7: The culture flasks are then incubated.

Example 3.5

Preparation of a Scaffold and Seeding of the Scaffold

Step 1: In a bio-safety hazard hood, scaffolds are placed into a sterile beaker. Ethanol was added to fill the entire beaker and left alone for 12 hrs.

Step 2: The ethanol was removed after 12 hrs and sterile PBS added to fill the entire beaker and left to stand for another 12 hrs.

Step 3: After 12 hrs, the PBS was removed and the scaffolds were dried by leaving them in the biosafety hazard hood for another 12 hrs Step 4: Within the biosafety cabinet, spent media in the culture flask were pipetted out. 6 ml of trypsin was pipetted into the culture flask to dislodge the cells.

Step 5: The flask was incubated at 37° C., 5% CO$_2$ in the bioreactor 10.

Step 6: Once all cells are detached from the flask, add 12 ml of complete DMEM (Sterile) into the culture flask to stop trypsinisation.

Step 7: The contents in the culture flask were pipetted into a centrifuge tube and send for centrifugation at 1000 rpm for 10 minutes.

Step 8: After centrifugation, the supernatant was removed and the residual cells re-suspended in 10 ml of DMEM media.

Step 9: The cell suspension is mixed with twice the amount of sterile sodium alginate solution to obtain a homogenous cell suspension. (4 mls of cell suspension per scaffold)

Step 10: The scaffolds were soak in sterile calcium chloride solution for a minute or so before it is seeded with the cells.

Step 11: While the scaffold is still dripping wet with the calcium chloride solution, 4 mls of the cell suspension with the sodium alginate is drawn and slowly seeded onto the scaffold. Any runoff is immediately sucked up onto the pipette and re-seeded onto the scaffold.

Step 12: After the 4 mls of cell suspension is seeded onto the scaffold, the scaffold is once again soaked in calcium chloride solution for a few seconds to make sure all the sodium alginate is coagulated to form a gel.

Step 13: The whole scaffold with the cells seeded is placed in culture container 302 with the media needed and incubated.

Example 3.6

Different Types of Assays

MTS Assay

Step 1: Drain the medium from the wells containing the scaffolds and add 500 µl of fresh serum free basal medium into the wells.

Step 2: The plates were to be wrapped immediately in aluminium foil to avoid any light exposure.

Step 3: Add 100 µl of MTS reagent into each well.

Step 4: Incubate for 3 hrs in the 5% carbon dioxide.

Step 5: After incubation, pipette the content of the wells to get a homogenous mixture and add 100 µl of the homogenized suspension into a 96 well culture plate. Step 6: Read the sample using a plate reader at a wavelength of 490 nm and calculate the mean value to obtain the result.

FDA and PI Viability Assay

Step 1: A Propidium Iodide Stock Solution [10 mg/ml PI in PBS] is prepared by diluting 100 ml stock solution in 1 ml PBS.

Step 2: A Fluorescein Diacetate Stock Solution [5 mg/ml FDA in PBS], is prepared by diluting 40 ml stock solution in 10 ml PBS.

Step 3: The samples were washed with PBS for 2 times.

Step 4: Samples were incubated at 37° C. with FDA working solution for 15 minutes.

Step 5: FDA working solution was removed and rinsed the sample twice with PBS.

Step 6: PI working solution was added into each sample, making sure the solution had covered the entire sample and incubated for 2 minutes at room temperature.

Step 7: Samples were rinsed twice again with PBS and viewed under the Fluorescent Microscope.

INDUSTRIAL APPLICATIONS

It will be appreciated that the cell and tissues grown/incubated by the bioreactor, system and method disclosed above can be used to prepare three-dimensional tissues and two-dimensional tissues, neo-tissue, a suspension of cells, scaffold constructs, and neo-tissue constructs.

The bioreactor, system and method disclosed herein provide physical signaling in two force vectors to grow three-dimensional cell or tissue cultures that mimic the function and structure of the parent tissue. The three-dimensional cell or tissue cultures of the present invention show superior characteristics over tissues grown by a single force vector.

Without being bound by theory, it is though that by applying two force vectors during incubation, the culture medium penetrates into the pores of any three dimensional matrices on which the cell or tissue cultures are grown. This enhanced penetration and induces a more penetrating flow pattern through the three-dimensional matrix, allowing the medium to reach fibroblast cells in the center of the matrix.

The pipe connectors of the present invention provide the advantage of allowing the medium to be re-circulated between the bioreactor and a support fermenter or some other unit operation in an industrial process without entanglement of any attached pipes as the reactor rotates. This allows the bioreactor to operate continuously, thereby achieving greater efficiencies that could not be achieved with a batch operated bioreactor.

Another advantage of the pipe connectors is that they allow the flow of multiple streams into and out of the reactor.

The bioreactors disclosed herein provide a device for growing cells that have cell-cell and cell-matrix interactions that are characteristic of whole tissue in vivo cells grown in three-dimensions.

The three-dimensional culture tissues produced by the bioreactor, system and method of the invention can be used in a variety of applications, including, not limited to, transplantation or implantation of either the cultured cells obtained from the matrix, or the cultured matrix itself in vivo. For transplantation or implantation in vivo, either the cells obtained from the culture or the entire three-dimensional culture could be implanted, depending upon the type of tissue involved. For example, three-dimensional bone marrow cultures can be maintained in vitro for long periods; the cells isolated from these cultures can be used in transplantation or the entire culture may be implanted. By contrast, in skin cultures, the entire three-dimensional culture can be grafted in vivo for treating burn victims, skin ulcerations and wounds.

Three-dimensional tissue culture implants may, according to the invention, be used to replace or augment existing tissue, to introduce new or altered tissue, to modify artificial prostheses, or to join together biological tissues or structures. Examples include: three-dimensional bone marrow culture implants for replacing bone marrow; three-dimensional liver tissue implants used to augment liver function; hip prostheses coated with three-dimensional cultures of cartilage; and dental prostheses joined to a three-dimensional culture of oral mucosa.

The bioreactors disclosed herein can be used to reproducibly create uniform tissues with suitable biochemical and mechanical properties. The bioreactor could be used for research applications, where one or a small number of cells or tissue constructs are made by an individual researcher, or on an industrial scale to meet market demand.

It will be appreciated that the bioreactors disclosed herein ensure a constant removal of metabolic waste products and provides the growing tissue with a constant supply of fresh nutrients.

The bioreactors disclosed herein grows cells and tissues that do not loose their differentiation status and are therefore functionally similar. Furthermore, the cells can be multiplied in a more natural way by culturing them in a bioreactor system which closely mimics the conditions of a naturally occurring physiological system.

The ability to dynamically control the speed at which the chamber of the bioreactor rotates about both horizontal and vertical axes allows physiologic tissue remodeling whereby the optimal parameters of incubation can be determined. It also provides a constant and regulatory supply of nutrition to the growing cells or tissues and a system for removal of metabolic byproducts. The bioreactor also maintains an organotypic environment to maintain cellular differentiation and optimal function.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A bioreactor comprising:
 a chamber for containing cells or tissue cultures within a culture medium;
 a detector capable of detecting a change in one or more metabolites associated with growth of the cell or tissue cultures within the chamber;
 a chamber drive capable of rotating the chamber at a first speed about a first axis and a second speed about a second axis, the second axis being disposed at an angle relative to the first axis, wherein in use, the magnitude of the first speed and the second speed are independently variable of each other; and
 an adjustment mechanism capable of adjusting the angle between the second axis and the first axis.

2. A bioreactor as claimed in claim 1, wherein said one or more metabolites is selected from the group consisting of: dissolved oxygen, dissolved carbon dioxide, glucose, lactate, glutamine, amino acids, lipids, carbohydrates, pyruvate, soluble proteins, cytokines and free radicals.

3. A bioreactor as claimed in claim 1, comprising a sensor capable of detecting at least one of pH, temperature and forces applied to the chamber as it rotates about the first and second axes.

4. A bioreactor as claimed in claim 1, wherein the angle between the first and second axes is in the range selected from the group consisting of: 60° to 120°; 70° to 110°; 80° to 100°; 85° to 95°; and 88° to 92°.

5. A bioreactor as claimed in claim 1, wherein the chamber drive is capable of rotating the chamber at a third speed about a third axis, the third axis being disposed at a second angle relative to the first axis.

6. A bioreactor as claimed in claim 5, wherein the magnitude of the third speed is independently variable of the first and second speeds.

7. A bioreactor as claimed in claim 5, wherein the angle between the first and third axes is in the range selected from the group consisting of: 60° to 120°; 70° to 110°; 80° to 100°; 85° to 95°; and 88° to 92°.

8. A bioreactor as claimed in claim 1, comprising:
 a fluidly sealed inlet passage extending into the chamber for passage of feed material into the chamber; and
 a fluidly sealed outlet passage extending into the chamber for passage of feed material out of the chamber.

9. A bioreactor as claimed in claim 1, comprising a controller for controlling one or more variables selected from the group consisting of: temperature, dissolved oxygen, glucose, pH, lactate, glutamine, amino acids, lipids, carbohydrates, pyruvate and combinations thereof.

10. A bioreactor as claimed in claim 5, wherein the chamber is substantially spherical or substantially elliptical in shape.

11. A bioreactor as claimed in claim 10, wherein the chamber drive comprises one or more servo motors capable of rotating the spherical or elliptical shaped chamber about at least one of the first axis, the second axis and the third axis.

12. A bioreactor as claimed in claim 1, wherein in use, the chamber drive is capable of rotating the chamber about an arc of rotation.

13. A bioreactor as claimed in claim 12, wherein the arc of rotation of the chamber is selected from the group consisting of: 20° to 180°, 30° to 150°, 45° to 120°, and 45° to 90°.

14. A bioreactor as claimed in claim 1, wherein in use, the chamber drive is capable of rotating the chamber continuously about at least one of the first axis and the second axis.

15. A bioreactor as claimed in claim 1, further comprising a compressor in fluid communication with said chamber, wherein in use, said compressor modulates the pressure within the chamber in use.

16. A method for growing cell or tissue cultures in vitro comprising the steps of:
   (a) providing a chamber having a cell or tissue culture within a culture medium;
   (b) rotating the chamber about a first axis at a first speed;
   (c) rotating the chamber about a second axis at a second speed, the second axis being disposed at an angle relative to the first axis, and wherein the magnitude of the first speed and the second speed are independently variable of each other; and
   (d) adjusting the angle between the first axis and the second axis.

17. A method as claimed in claim 16, further comprising the step of:
   (e) detecting a change in one or more metabolites associated with growth of the cell or tissue culture within the chamber.

18. A method as claimed in claim 17, said detecting step (e) comprises the step of:
   (e1) detecting said one or more metabolites from the group consisting of: dissolved oxygen, dissolved carbon dioxide, glucose, lactate, glutamine, amino acids, lipids, carbohydrates, pyruvate, soluble proteins, cytokines and free radicals.

19. A method as claimed in claim 16, further comprising the step of:
   (f) maintaining the chamber at a pressure higher than ambient pressure during cell or tissue growth.

20. A method as claimed in claim 16, further comprising the step of:
   (g) maintaining the pressure within chamber selected from the group consisting of: 0 KPa to 3000 KPa, 50 KPa to 1500 KPa, 50 KPa to 1000 KPa, and 50 KPa to 500 KPa.

21. A method as claimed in claim 16, wherein said rotating step (c) further comprises the step of:
   (c1) rotating the chamber about an arc of rotation selected from the group consisting of: 20° to 180°, 30° to 150°, 45° to 120°, and 45° to 90°.

22. A method as claimed in claim 16, wherein said rotating step (c) further comprises the step of:
   (c2) rotating the chamber continuously about at least one of the first axis and the second axis.

23. A bioreactor comprising:
   a substantially spherical or substantially elliptical shaped chamber capable of containing cell or tissue culture within a culture medium;
   a chamber support to support the chamber and comprising rollers to allow the chamber to rotate about at least a first axis and a second axis, the second axis being disposed at an angle relative to the first axis;
   a chamber drive capable of rotating the chamber at a first speed about the first axis and a second speed about the second axis, wherein in use, the magnitude of the first speed and the second speed are independently variable of each other; and
   an adjustment mechanism capable of adjusting the angle between the second axis and first axis.

24. A bioreactor as claimed in claim 23, wherein the chamber drive is capable of rotating the chamber at a third speed about a third axis, the third axis being disposed at a second angle relative to the first axis, and wherein in use, the magnitude of the third speed is independently variable of the first and second speeds.

25. The bioreactor as claimed in claim 1, wherein the adjustment mechanism is capable of varying the position of the chamber with respect to one of said axis.

\* \* \* \* \*

UNITED STATES PATENT AND TRADEMARK OFFICE
CERTIFICATE OF CORRECTION

PATENT NO. : 7,604,987 B2 Page 1 of 1
APPLICATION NO. : 11/124618
DATED : October 20, 2009
INVENTOR(S) : Hutmacher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1086 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

PATENT NO.      : 7,604,987 B2  
APPLICATION NO. : 11/124618  
DATED           : October 20, 2009  
INVENTOR(S)     : Hutmacher et al.

Page 1 of 1

It is certified that error appears in the above-identified patent and that said Letters Patent is hereby corrected as shown below:

On the title page item (73) Assignee should read: --National University of Singapore, Singapore (SG); Singapore Polytechnic, Singapore (SG)--;

Col. 48, Line 35, "said axis." should read --said axes--.

Signed and Sealed this
Fourth Day of January, 2011

David J. Kappos
*Director of the United States Patent and Trademark Office*